United States Patent
Horne et al.

(10) Patent No.: US 8,109,274 B2
(45) Date of Patent: Feb. 7, 2012

(54) METHODS AND ELECTRODE APPARATUS TO ACHIEVE A CLOSURE OF A LAYERED TISSUE DEFECT

(75) Inventors: Kenneth Horne, San Francisco, CA (US); Jose Alejandro, Sunnyvale, CA (US); Erik Engelson, Menlo Park, CA (US); Dominique Filloux, Redwood City, CA (US); Dan Francis, Mountain View, CA (US); Lucia Kim, San Jose, CA (US); Uday N. Kumar, San Francisco, CA (US); Doug Sutton, Pacifica, CA (US); Miriam H. Taimisto, San Jose, CA (US); Andy Uchida, Mountain View, CA (US)

(73) Assignee: Terumo Kabushiki Kaisha, Tokyo (JP)

( * ) Notice: Subject to any disclaimer, the term of this patent is extended or adjusted under 35 U.S.C. 154(b) by 1645 days.

(21) Appl. No.: 11/403,052

(22) Filed: Apr. 11, 2006

(65) Prior Publication Data
US 2006/0271040 A1 Nov. 30, 2006

Related U.S. Application Data

(60) Provisional application No. 60/670,535, filed on Apr. 11, 2005.

(51) Int. Cl.
*A61B 19/00* (2006.01)
(52) U.S. Cl. .......... 128/898; 606/49; 607/101; 607/119
(58) Field of Classification Search .......... 606/8, 13–15, 606/40, 49–52; 607/96–102, 116, 119; 128/898
See application file for complete search history.

(56) References Cited

U.S. PATENT DOCUMENTS

| 2,275,167 A | 3/1942 | Bierman |
| 2,580,628 A | 1/1952 | Welsh |

(Continued)

FOREIGN PATENT DOCUMENTS

EP 135840 A2 4/1985
(Continued)

OTHER PUBLICATIONS

Anzola et al., "Potential Source of Cerebral Embolism in Migraine with Aura," *Neurology* (1999) 52(8): 1622.
(Continued)

*Primary Examiner* — Ahmed Farah
(74) *Attorney, Agent, or Firm* — Oblon, Spivak, McClelland, Maier & Neustadt, L.L.P.

(57) ABSTRACT

Methods for treating anatomic tissue defects such as a patent foramen ovale generally involve positioning a distal end of a catheter device at the site of the defect, exposing a housing and energy transmission member from the distal end of the catheter, engaging the housing with tissues at the site of the defect, applying suction or other approximating tool to the tissue via the housing to bring the tissue together, and applying energy to the tissue with the energy transmission member or to deliver a clip or fixation device to substantially close the defect. Apparatus generally include a catheter body, a housing extending from a distal end of the catheter body for engaging tissue at the site of the defect, and further adapted to house a fusing or fixation device such as an energy transmission member adjacent a distal end of the housing, or a clip or fixation delivery element.

9 Claims, 55 Drawing Sheets

U.S. PATENT DOCUMENTS

| | | |
|---|---|---|
| 2,888,928 A | 6/1959 | Seiger |
| 3,490,442 A | 1/1970 | Streu |
| 3,862,627 A | 1/1975 | Hans, Sr. |
| 3,874,388 A | 4/1975 | King et al. |
| 3,906,955 A | 9/1975 | Roberts |
| 4,307,720 A | 12/1981 | Weber, Jr. |
| 4,326,529 A | 4/1982 | Doss et al. |
| 4,473,077 A | 9/1984 | Noiles et al. |
| 4,485,817 A | 12/1984 | Swiggett |
| 4,532,924 A | 8/1985 | Auth et al. |
| 4,556,065 A | 12/1985 | Hoffmann |
| 4,562,838 A | 1/1986 | Walker |
| 4,590,934 A | 5/1986 | Malis et al. |
| 4,682,596 A | 7/1987 | Bales et al. |
| 4,788,975 A | 12/1988 | Shturman et al. |
| 4,798,594 A | 1/1989 | Hillstead |
| 4,832,048 A | 5/1989 | Cohen |
| 4,884,567 A | 12/1989 | Elliot et al. |
| 4,895,565 A | 1/1990 | Hillstead |
| 4,911,159 A | 3/1990 | Johnson et al. |
| 4,919,129 A | 4/1990 | Weber, Jr. et al. |
| 4,929,246 A | 5/1990 | Sinofsky |
| 4,976,711 A | 12/1990 | Parins et al. |
| 4,986,889 A | 1/1991 | Charamathieu et al. |
| 5,041,095 A | 8/1991 | Littrell |
| 5,042,707 A | 8/1991 | Taheri |
| 5,055,100 A | 10/1991 | Olsen |
| 5,056,517 A | 10/1991 | Fenici |
| 5,057,107 A | 10/1991 | Parins et al. |
| 5,071,417 A | 12/1991 | Sinofsky |
| 5,071,418 A | 12/1991 | Rosenbaum |
| 5,078,717 A | 1/1992 | Parins et al. |
| 5,099,827 A | 3/1992 | Melzer et al. |
| RE33,925 E | 5/1992 | Bales et al. |
| 5,125,928 A | 6/1992 | Parins et al. |
| 5,156,608 A | 10/1992 | Troidl et al. |
| 5,156,613 A | 10/1992 | Sawyer |
| 5,171,311 A | 12/1992 | Rydell |
| 5,195,959 A | 3/1993 | Smith |
| 5,196,007 A | 3/1993 | Ellman et al. |
| 5,197,963 A | 3/1993 | Parins |
| 5,207,670 A | 5/1993 | Sinofsky |
| 5,209,756 A | 5/1993 | Seedhom et al. |
| 5,290,278 A | 3/1994 | Anderson |
| 5,292,362 A | 3/1994 | Bass et al. |
| 5,295,955 A | 3/1994 | Rosen et al. |
| 5,300,065 A | 4/1994 | Anderson |
| 5,336,221 A | 8/1994 | Anderson |
| 5,336,252 A | 8/1994 | Cohen |
| 5,342,413 A | 8/1994 | Hirschberg et al. |
| 5,345,935 A | 9/1994 | Hirsch |
| 5,370,675 A | 12/1994 | Edwards et al. |
| 5,380,304 A | 1/1995 | Parker |
| 5,383,917 A | 1/1995 | Desai et al. |
| 5,405,322 A | 4/1995 | Lennox et al. |
| 5,409,479 A | 4/1995 | Dew et al. |
| 5,409,481 A | 4/1995 | Poppas et al. |
| 5,500,012 A | 3/1996 | Brucker et al. |
| 5,505,730 A | 4/1996 | Edwards |
| 5,507,744 A | 4/1996 | Tay et al. |
| 5,540,677 A | 7/1996 | Sinofsky |
| 5,569,239 A | 10/1996 | Sinofsky |
| 5,571,216 A | 11/1996 | Anderson |
| 5,575,772 A | 11/1996 | Lennox |
| 5,584,872 A | 12/1996 | Lafontaine et al. |
| 5,611,794 A | 3/1997 | Sauer et al. |
| 5,620,481 A | 4/1997 | Desai et al. |
| 5,626,607 A | 5/1997 | Malecki et al. |
| 5,662,643 A | 9/1997 | Kung et al. |
| 5,665,109 A | 9/1997 | Yoon |
| 5,669,934 A | 9/1997 | Sawyer |
| 5,693,078 A | 12/1997 | Desai et al. |
| 5,709,224 A | 1/1998 | Behl |
| 5,713,891 A | 2/1998 | Poppas |
| 5,725,522 A * | 3/1998 | Sinofsky ................ 606/8 |
| 5,730,742 A | 3/1998 | Wojciechowicz |
| 5,749,895 A | 5/1998 | Sawyer et al. |
| 5,782,899 A | 7/1998 | Imran |
| 5,814,065 A | 9/1998 | Diaz |
| 5,824,015 A | 10/1998 | Sawyer |
| 5,827,265 A | 10/1998 | Glinsky et al. |
| 5,846,196 A | 12/1998 | Siekmeyer et al. |
| 5,855,312 A | 1/1999 | Toledano |
| 5,871,443 A | 2/1999 | Edwards et al. |
| 5,919,200 A | 7/1999 | Stambaugh et al. |
| 5,925,078 A | 7/1999 | Anderson |
| 5,928,266 A | 7/1999 | Kontos |
| 5,931,165 A | 8/1999 | Reich et al. |
| 5,944,738 A | 8/1999 | Amplatz et al. |
| 5,972,023 A | 10/1999 | Tanner et al. |
| 5,972,024 A | 10/1999 | Northrup, III et al. |
| 6,004,316 A | 12/1999 | Laufer |
| 6,012,457 A | 1/2000 | Lesh |
| 6,036,699 A | 3/2000 | Andreas et al. |
| 6,050,994 A | 4/2000 | Sherman |
| 6,056,760 A | 5/2000 | Koike et al. |
| 6,063,081 A | 5/2000 | Mulier |
| 6,063,085 A | 5/2000 | Tay |
| 6,083,223 A | 7/2000 | Baker |
| 6,086,570 A | 7/2000 | Aboul-Hosn et al. |
| 6,086,586 A | 7/2000 | Hooven |
| 6,087,552 A | 7/2000 | Gregory |
| 6,092,528 A | 7/2000 | Edwards |
| 6,132,429 A | 10/2000 | Baker |
| 6,149,660 A | 11/2000 | Laufer et al. |
| 6,156,032 A | 12/2000 | Lennox |
| 6,168,594 B1 | 1/2001 | Lafontaine |
| 6,211,335 B1 | 4/2001 | Owen et al. |
| 6,221,068 B1 | 4/2001 | Fried et al. |
| 6,236,875 B1 | 5/2001 | Bucholz |
| 6,257,241 B1 | 7/2001 | Wampler |
| 6,290,674 B1 | 9/2001 | Roue et al. |
| 6,302,898 B1 | 10/2001 | Edwards et al. |
| 6,323,037 B1 | 11/2001 | Lauto et al. |
| 6,325,798 B1 | 12/2001 | Edwards et al. |
| 6,355,030 B1 | 3/2002 | Aldrich et al. |
| 6,358,246 B1 | 3/2002 | Behl et al. |
| 6,375,668 B1 | 4/2002 | Gifford et al. |
| 6,383,198 B1 | 5/2002 | Hamilton |
| 6,391,048 B1 | 5/2002 | Ginn et al. |
| 6,391,049 B1 | 5/2002 | McNally et al. |
| 6,398,779 B1 | 6/2002 | Buysee et al. |
| 6,398,782 B1 | 6/2002 | Pecor et al. |
| 6,398,797 B2 | 6/2002 | Bombard et al. |
| 6,401,720 B1 | 6/2002 | Stevens et al. |
| 6,409,720 B1 | 6/2002 | Hissong et al. |
| 6,413,254 B1 | 7/2002 | Hissong et al. |
| 6,419,669 B1 | 7/2002 | Frazier et al. |
| 6,423,057 B1 | 7/2002 | He et al. |
| 6,436,088 B2 | 8/2002 | Frazier et al. |
| 6,451,013 B1 | 9/2002 | Bays et al. |
| 6,456,865 B2 | 9/2002 | Samson |
| 6,458,100 B2 | 10/2002 | Roue et al. |
| 6,475,213 B1 | 11/2002 | Whayne et al. |
| 6,482,224 B1 | 11/2002 | Michler et al. |
| 6,514,250 B1 | 2/2003 | Jahns et al. |
| 6,558,314 B1 | 5/2003 | Adelman et al. |
| 6,558,382 B2 | 5/2003 | Jahns et al. |
| 6,562,037 B2 | 5/2003 | Paton et al. |
| 6,583,117 B2 | 6/2003 | Owen et al. |
| 6,584,360 B2 | 6/2003 | Francischelli et al. |
| 6,589,237 B2 | 7/2003 | Woloszko |
| 6,606,523 B1 | 8/2003 | Jenkins |
| 6,641,604 B1 | 11/2003 | Adelman |
| 6,645,202 B1 | 11/2003 | Pless et al. |
| 6,645,225 B1 | 11/2003 | Atkinson |
| 6,648,897 B2 | 11/2003 | Hamilton |
| 6,652,518 B2 | 11/2003 | Wellman et al. |
| 6,669,693 B2 | 12/2003 | Friedman |
| 6,676,685 B2 | 1/2004 | Pedros et al. |
| 6,682,546 B2 | 1/2004 | Amplatz |
| 6,692,450 B1 | 2/2004 | Coleman |
| 6,702,835 B2 | 3/2004 | Ginn |
| 6,712,804 B2 | 3/2004 | Roue et al. |
| 6,712,836 B1 | 3/2004 | Berg et al. |
| 6,716,211 B2 | 4/2004 | Mulier et al. |
| 6,726,718 B1 | 4/2004 | Carlyle et al. |

| | | |
|---|---|---|
| 6,730,108 B2 | 5/2004 | Van Tassel et al. |
| 6,733,498 B2 | 5/2004 | Paton et al. |
| 6,736,810 B2 | 5/2004 | Hoey et al. |
| 6,755,790 B2 | 6/2004 | Stewart et al. |
| 6,770,072 B1 | 8/2004 | Truckai et al. |
| 6,776,784 B2 | 8/2004 | Ginn |
| 6,790,218 B2 | 9/2004 | Jayaraman |
| 6,846,319 B2 | 1/2005 | Ginn et al. |
| 6,887,238 B2 | 5/2005 | Jahns |
| 6,893,431 B2 | 5/2005 | Naimark et al. |
| 6,893,442 B2 | 5/2005 | Whayne |
| 6,918,908 B2 | 7/2005 | Bonner et al. |
| 6,926,716 B2 | 8/2005 | Baker et al. |
| 6,929,644 B2 | 8/2005 | Truckai et al. |
| 6,932,812 B2 | 8/2005 | Crowley et al. |
| 6,939,348 B2 * | 9/2005 | Malecki et al. ............... 606/41 |
| 6,946,134 B1 | 9/2005 | Rosen et al. |
| 6,960,205 B2 | 11/2005 | Jahns et al. |
| 6,972,421 B2 * | 12/2005 | Melnychuk et al. ....... 250/504 R |
| 7,025,756 B2 | 4/2006 | Frazier et al. |
| 7,094,215 B2 | 8/2006 | Davison et al. |
| 7,165,552 B2 | 1/2007 | Deem et al. |
| 7,238,182 B2 | 7/2007 | Swoyer et al. |
| 7,318,823 B2 * | 1/2008 | Sharps et al. ................. 606/32 |
| 7,367,975 B2 | 5/2008 | Malecki et al. |
| 2001/0020166 A1 | 9/2001 | Daly et al. |
| 2001/0037129 A1 | 11/2001 | Thill |
| 2001/0051803 A1 | 12/2001 | Desai et al. |
| 2002/0128672 A1 | 9/2002 | Dinger et al. |
| 2002/0143322 A1 | 10/2002 | Haghighi |
| 2002/0156472 A1 | 10/2002 | Lee et al. |
| 2003/0028189 A1 | 2/2003 | Woloszko et al. |
| 2003/0045893 A1 | 3/2003 | Ginn |
| 2003/0045901 A1 | 3/2003 | Opolski |
| 2003/0050665 A1 | 3/2003 | Ginn |
| 2003/0065364 A1 | 4/2003 | Wellman et al. |
| 2003/0069570 A1 | 4/2003 | Witzel |
| 2003/0078578 A1 | 4/2003 | Truckai et al. |
| 2003/0092988 A1 | 5/2003 | Markin |
| 2003/0093071 A1 | 5/2003 | Hauck et al. |
| 2003/0120268 A1 | 6/2003 | Bertolero et al. |
| 2003/0144652 A1 | 7/2003 | Baker et al. |
| 2003/0144694 A1 | 7/2003 | Chanduszko et al. |
| 2003/0158551 A1 | 8/2003 | Paton et al. |
| 2003/0199868 A1 | 10/2003 | Desai et al. |
| 2003/0208232 A1 | 11/2003 | Blaeser |
| 2003/0225421 A1 | 12/2003 | Peavey et al. |
| 2003/0233091 A1 | 12/2003 | Whayne et al. |
| 2004/0059347 A1 | 3/2004 | Hamilton |
| 2004/0092973 A1 | 5/2004 | Chanduszko et al. |
| 2004/0098031 A1 | 5/2004 | Van der Burg et al. |
| 2004/0098042 A1 | 5/2004 | Devellian et al. |
| 2004/0102721 A1 | 5/2004 | Mckinley |
| 2004/0143292 A1 | 7/2004 | Marino et al. |
| 2004/0153057 A1 | 8/2004 | Davison |
| 2004/0153098 A1 | 8/2004 | Chin et al. |
| 2004/0176799 A1 | 9/2004 | Chanduszko et al. |
| 2004/0220596 A1 | 11/2004 | Frazier et al. |
| 2004/0243122 A1 | 12/2004 | Auth |
| 2004/0249398 A1 | 12/2004 | Ginn |
| 2005/0021059 A1 | 1/2005 | Cole et al. |
| 2005/0033288 A1 | 2/2005 | Auth et al. |
| 2005/0033327 A1 | 2/2005 | Gainor et al. |
| 2005/0055050 A1 | 3/2005 | Alfaro |
| 2005/0065506 A1 | 3/2005 | Phan |
| 2005/0065509 A1 | 3/2005 | Coldwell et al. |
| 2005/0070952 A1 | 3/2005 | Mcintosh |
| 2005/0075665 A1 | 4/2005 | Brenzel et al. |
| 2005/0080406 A1 | 4/2005 | Malecki et al. |
| 2005/0119675 A1 | 6/2005 | Adams et al. |
| 2005/0125032 A1 | 6/2005 | Whisenant et al. |
| 2005/0131401 A1 | 6/2005 | Malecki et al. |
| 2005/0171526 A1 | 8/2005 | Rioux et al. |
| 2005/0187568 A1 | 8/2005 | Klenk et al. |
| 2005/0192626 A1 | 9/2005 | Widomski et al. |
| 2005/0192627 A1 | 9/2005 | Whisenant et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2005/0251201 A1 | 11/2005 | Roue et al. |
| 2005/0256532 A1 | 11/2005 | Nayak et al. |
| 2005/0267495 A1 | 12/2005 | Ginn et al. |
| 2005/0267525 A1 | 12/2005 | Chanduszko |
| 2006/0009762 A1 | 1/2006 | Whayne |
| 2006/0036284 A1 | 2/2006 | Blaeser et al. |
| 2006/0052821 A1 | 3/2006 | Abbott et al. |
| 2006/0069408 A1 | 3/2006 | Kato |
| 2006/0079870 A1 | 4/2006 | Barry |
| 2006/0079887 A1 | 4/2006 | Buysse et al. |
| 2006/0173510 A1 | 8/2006 | Besio et al. |
| 2006/0271030 A1 | 11/2006 | Francis et al. |
| 2006/0271040 A1 | 11/2006 | Horne et al. |
| 2007/0088355 A9 | 4/2007 | Auth |
| 2007/0287999 A1 | 12/2007 | Malecki et al. |

FOREIGN PATENT DOCUMENTS

| | | |
|---|---|---|
| EP | 199694 A2 | 10/1986 |
| EP | 0265532 A1 | 5/1988 |
| EP | 0375556 A1 | 6/1990 |
| EP | 0428812 A1 | 5/1991 |
| EP | 0947165 A1 | 10/1999 |
| GB | 1260919 | 1/1972 |
| GB | 1550676 | 8/1979 |
| GB | 2 359 024 A | 8/2001 |
| WO | WO 85/00018 A1 | 1/1985 |
| WO | WO 87/04081 A1 | 7/1987 |
| WO | WO 90/04352 A1 | 5/1990 |
| WO | WO 91/15996 A1 | 10/1991 |
| WO | WO 92/04864 A1 | 4/1992 |
| WO | WO 93/05705 A1 | 4/1993 |
| WO | WO 93/15791 A1 | 8/1993 |
| WO | WO 94/00178 A1 | 1/1994 |
| WO | WO 98/07375 A1 | 2/1998 |
| WO | WO 99/18862 A1 | 4/1999 |
| WO | WO 99/18864 A1 | 4/1999 |
| WO | WO 99/18870 A1 | 4/1999 |
| WO | WO 99/18871 A1 | 4/1999 |
| WO | WO 99/23959 A1 | 5/1999 |
| WO | WO 99/49788 A | 10/1999 |
| WO | WO 00/07506 A2 | 2/2000 |
| WO | WO 00/09027 A1 | 2/2000 |
| WO | WO 01/13810 A1 | 3/2001 |
| WO | WO 01/78596 A1 | 10/2001 |
| WO | WO 01/82778 A | 11/2001 |
| WO | WO 03/022159 A1 | 3/2003 |
| WO | WO 03/022160 A1 | 3/2003 |
| WO | WO 03/026496 A2 | 4/2003 |
| WO | WO 03/053493 A2 | 7/2003 |
| WO | WO 03/071957 A2 | 9/2003 |
| WO | WO 03/082076 A2 | 10/2003 |
| WO | WO 03/094742 A1 | 11/2003 |
| WO | WO 2004/019791 A2 | 3/2004 |
| WO | WO 2004/043266 A2 | 5/2004 |
| WO | WO 2004/069055 A2 | 8/2004 |
| WO | WO 2004/082532 A1 | 9/2004 |
| WO | WO 2004/091411 A2 | 10/2004 |
| WO | WO 2005/006990 A2 | 1/2005 |
| WO | WO 2005/027753 A1 | 3/2005 |
| WO | WO 2005/034738 A2 | 4/2005 |
| WO | WO 2005/074814 A2 | 8/2005 |
| WO | WO 2005/046487 A1 | 12/2005 |
| WO | WO 2005/115256 A | 12/2005 |

OTHER PUBLICATIONS

Athiraman et al., "Selective Photothermal Tissue Interaction Using 805-nm Laser and Indocyanine Green in Tissue Welding," *Journal of X-Ray Science and Technology*, (2004), vol. 12(2): 117-126.

De Castro et al., "Morphological and Functional Characteristics of Patent Foramen Ovale and Their Embolic Implications," *Stroke* (Oct. 2002), 10: 2407-2413.

Cordis Corporation, Cordis Ducor® Lumeleo™ Electrode Catheters [brochure], Cordis Corporation, (Dec. 1984), 2 pages.

Del Sette, "Migraine with Aura and Right-to-Left Shunt on Transcranial Doppler: A Case Control Study," *Cerebrovas Dis* (1998) 8:327-330.

Fenner et al., "Shear Strength of Tissue Bonds as a Function of Bonding Temperature: A Proposed Mechanism for Laser-Assisted Tissue Welding," *Lasers in Medical Science*, (1992), 7:39-43.

Godlewski et al., "Applications and Mechanisms of Laser Tissue Welding in 1995: Review," *Proc. SPIE*, (Jan. 1996) 2623: 334-341.

Gillette, "Catheter Ablation in Dysrhythmias," *Cardio*, (Mar. 1984), pp. 67-69.

Ho et al., "Morphological Features Pertinent to Interventional Closure of Patent Oval Foramen," *J Interventional Cardiology*, (2003) 16(1): 33-34.

Kennedy et al., "High-burst-Strength, feedback-controlled bipolar vessel sealing," *Surg Endosc* (1998) 12:876-878.

Koenig et al., "Role of Intracardiac Echocardiographic Guidance in Transcatheter Closure of Atrial Septal Defects and Patent Foramen Ovale Using the Amplatzer® Device," *J. Interventional Cardiology*, (2003) 16 (1): 51-62.

Morady, "Transvenous Catheter Ablation of a Posterospetial Accessory Pathway in a Patient with the Wolff Parkinson-White Syndrome," *The New England Journal of Medicine*, (Mar. 15, 1984), 310(11): 705-707.

Morandi et al., "Transcatheter Closure of Patent Foramen Ovale: A New Migraine Treatment?" *J Interventional Cardiology*, (2003), 16(1): 39-42.

Olson et al., "Developing an Animal Model for the Study of Fusion Using RF Energy," *Proc. SPIE*, (2004) 5312: 147-161.

Ott et al., "Comparative in Vitro Study of Tissue Welding Using a 808 nm Diode Laser and a Ho:YAG laser," *Lasers Med Sci*, (2001)16: 260-266.

Pfleger, "Haemodynamic Quantification of Different Provocation Manoeuvres by Simultaneous Measurement of Right and Left Atrial Pressure: Implications for the Echocardiographic Detection of Persistent Foramen Ovale," *Eur J Echocardiography* (2001) 2:88-93.

Polgar et al., "A New Technique for Closed-Chest Human His Bundle Ablation Using Suction Electrode Catheter and DC Shock," In: Perez Gomez F, ed. Cardiac Pacing Electrophysiology Tachyarrhythmias. Madrid, Spain: Grouz Publishers; (1985) pp. 1582-1586.

Polgar et al., "Comparison of Two Different Techniques for Closed-Chest His Bundle Ablation," In: Perez Gomez F, ed. Cardiac Pacing Electrophysiology Tachyarrhythmias. Madrid, Spain: Grouz Publishers; 1985:1578-1587.

Polgar, "Closed Chested Ablation of His Bundle: A New Technique Using Suction Electorde Catheter and DC Shock," *Nachdruck Aus: Cardio Pacing*, (1983), pp. 883-890.

Poppas et al., "Temperature-Controlled Laser Photocoagulation of Soft Tissue: in Vivo Evaluation Using a Tissue Welding Model," *Lasers Surg Med.*, (1996) 18 (4): 335-344.

Stewart et al., "Laser Assisted Vascular Welding with Real Time Temperature Control," *Lasers Surg Med.*, (1996) 19(1): 9-16.

Stuart, "What's All the Flap About PFO Closure?," *Start-Up: Windhover's Review of Emerging Medical Ventures*, (Nov. 10, 2004), pp. 9-14.

Sztajzel et al., "Patent Foramen Ovale, a Possible Cause of Symptomatic Migraine: A Study of 74 Patients with Acute Ischemic Stroke," *Cerebrovas Dis* (2002) 13: 102-106.

Tang et al., "Quantitative Changes in Collagen Levels Following 830-nm Diode Laser Welding," *Lasers Surg Med.*, (1998) 22( 4): 207-211.

Tang et al, "Morphologic Changes in Collagen Fibers after 830 nm Diode Laser Welding," *Lasers Surg Med.*, (1997) 21: 5438-43.

Thomas, "Patent Foramen Ovale with Right-to-left Shunting: Echocariographic Alternatives," *Eur J Echocariography* (2001) 2:74-75.

Wilmhurst et al., "Effect on Migraine of Closure of Cardiac Right-to-Left Shunts to Prevent Recurrence of Decompression Illness of Illness or Stroke or for Haemodynamic Reasons," *The Lancet*, (Nov. 11, 2000) 356:1648-1651.

Wilmhurst et al., "Relationship between Migraine and Cardiac and Pulmonary Right to Left Shunts," *Clinical Science* (2001) 100:215-220.

Besio et al., "Quantizing the Depth of Bioelectrical Sources for Non-Invasive 3D Imaging," IJBEM, vol. 7, No. 2, 2005, 4 pages total.

\* cited by examiner

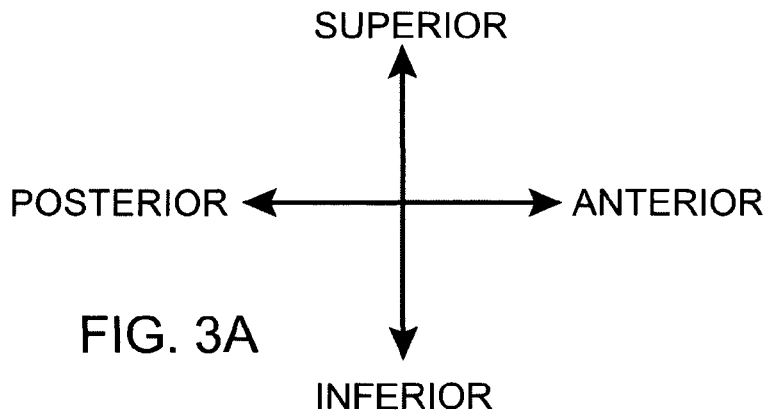
FIG. 3A
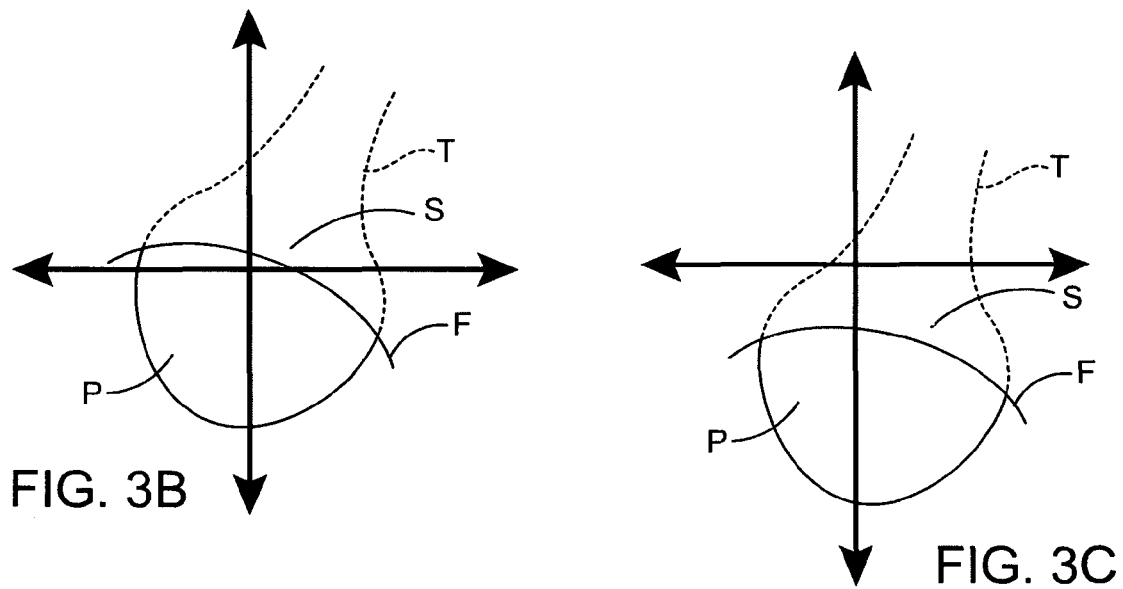
FIG. 3B
FIG. 3C
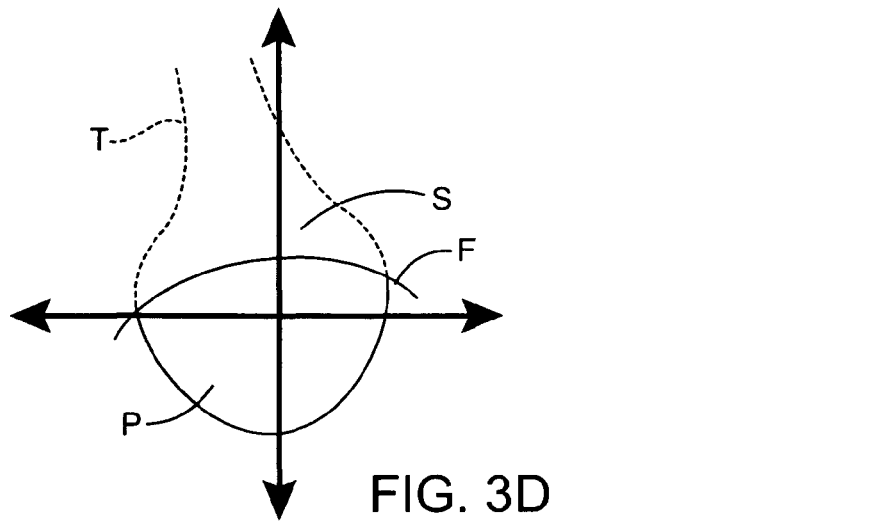
FIG. 3D

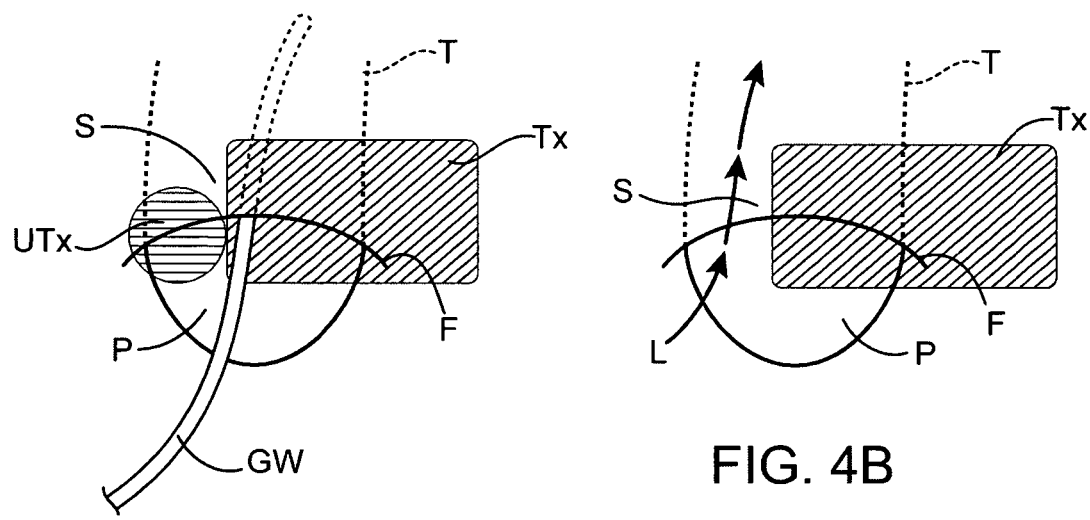
FIG. 4A
FIG. 4B
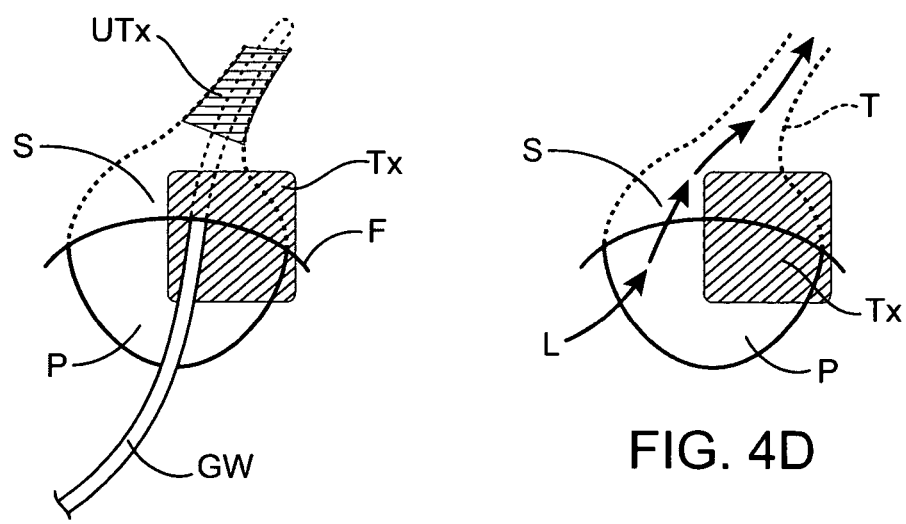
FIG. 4C
FIG. 4D

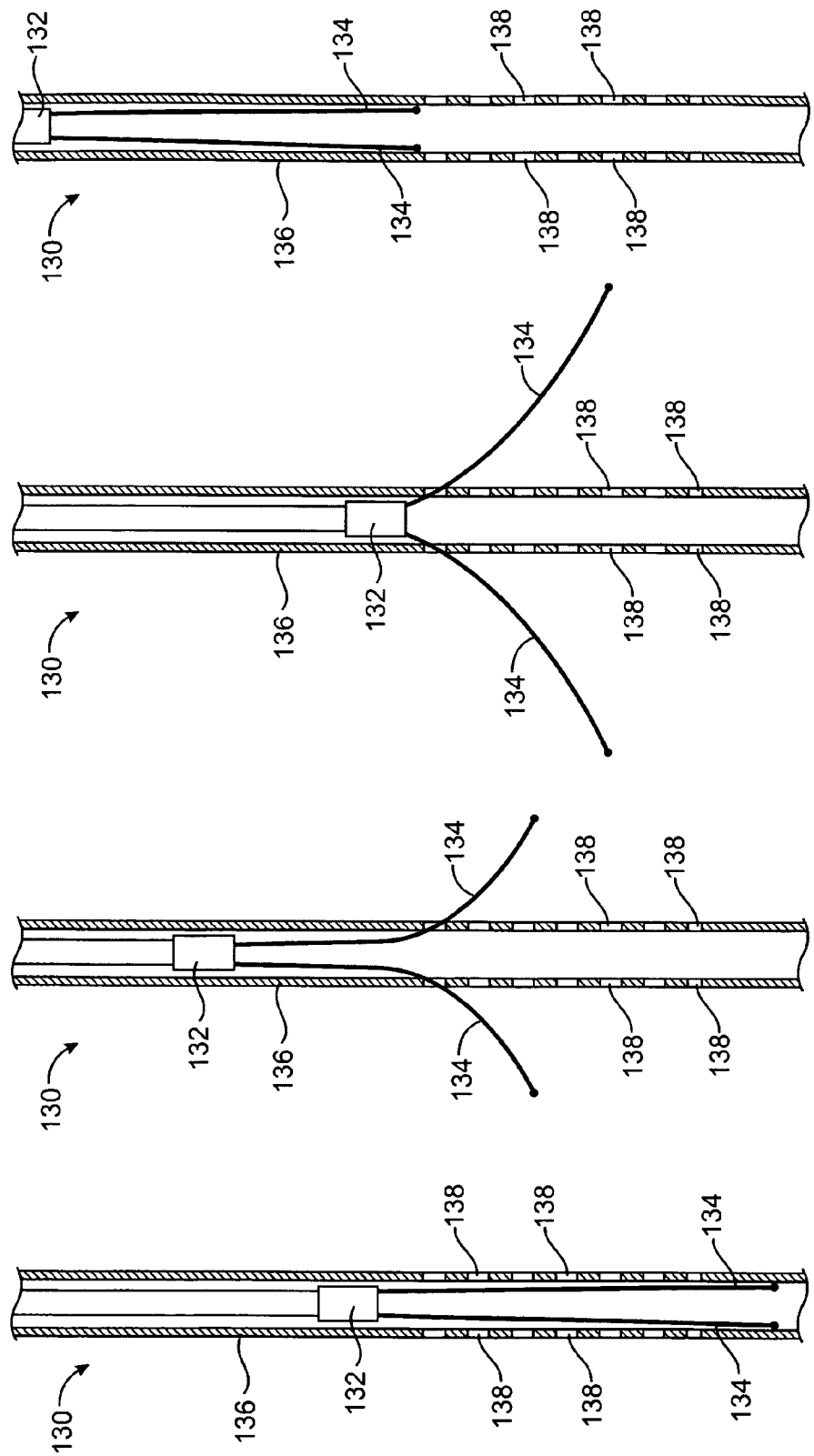

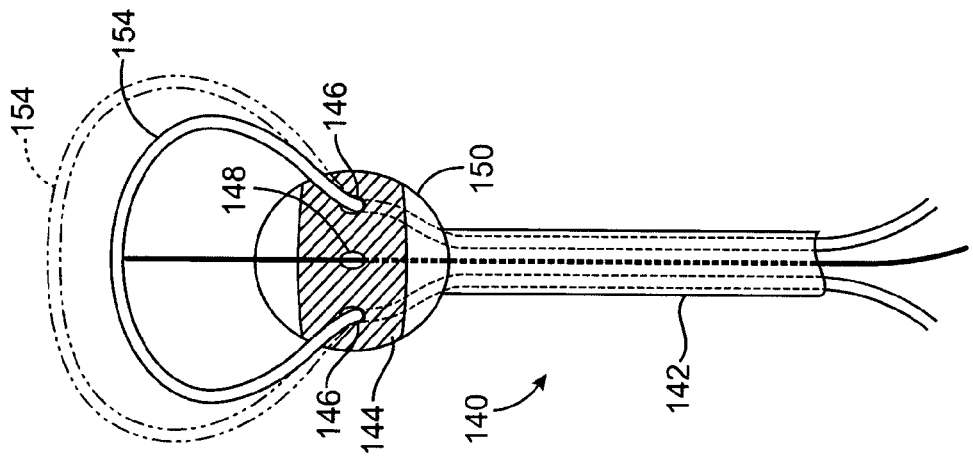
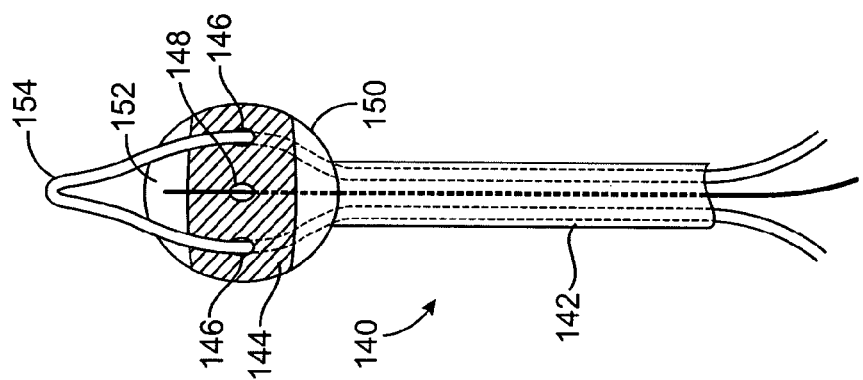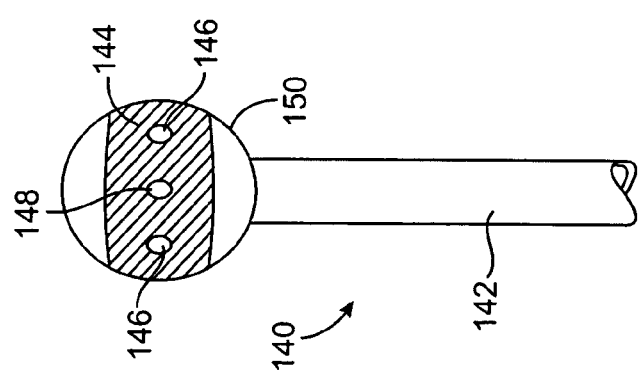

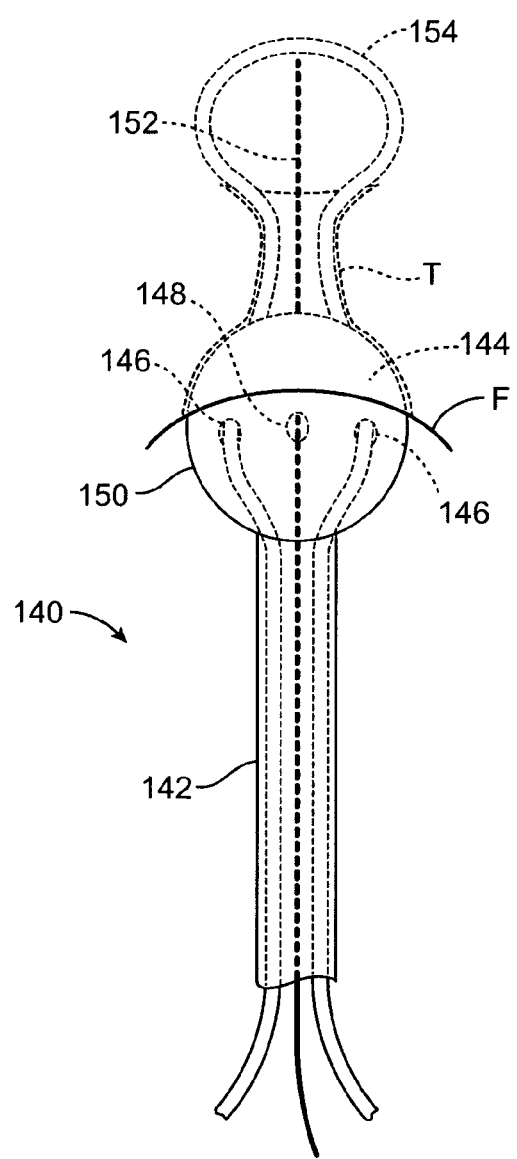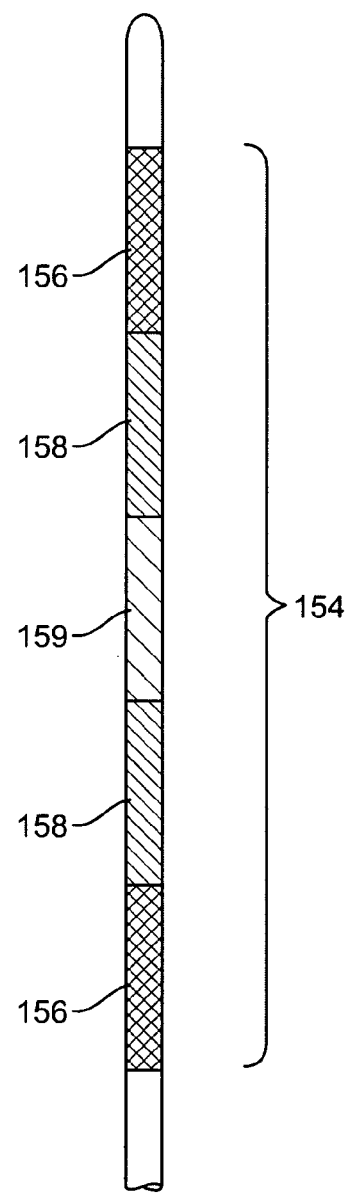
FIG. 16D
FIG. 16E

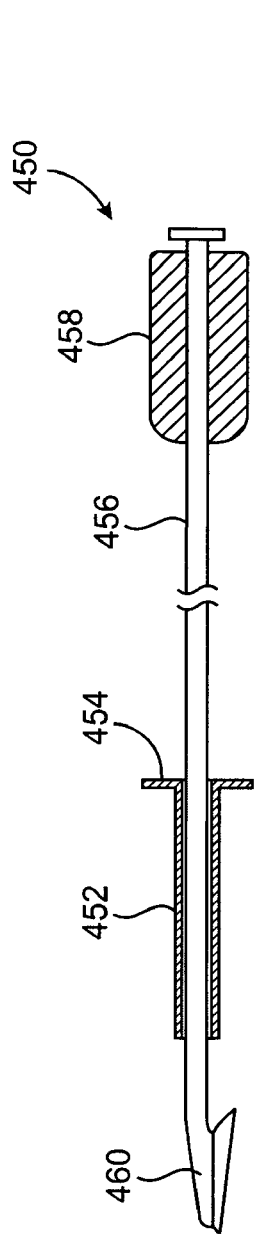
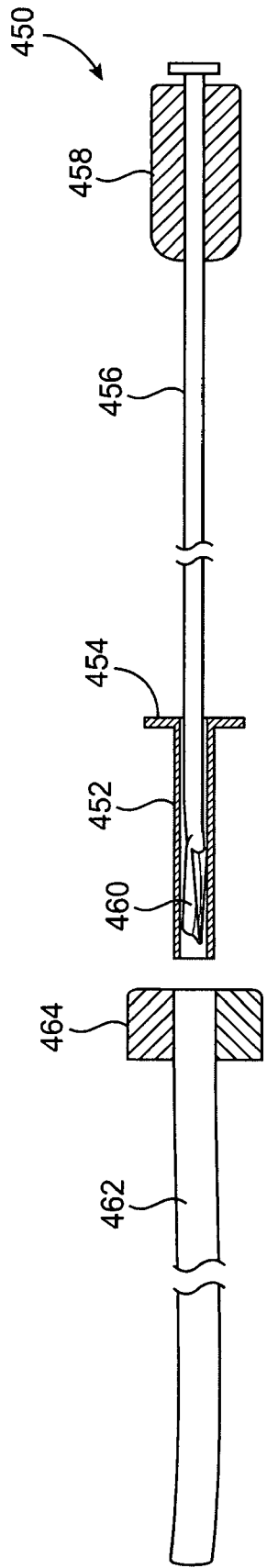
FIG. 24A
FIG. 24B

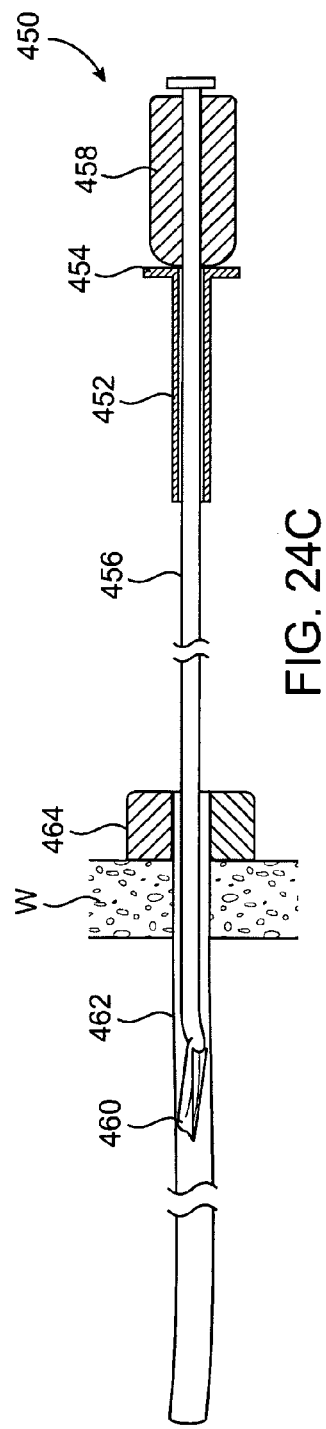
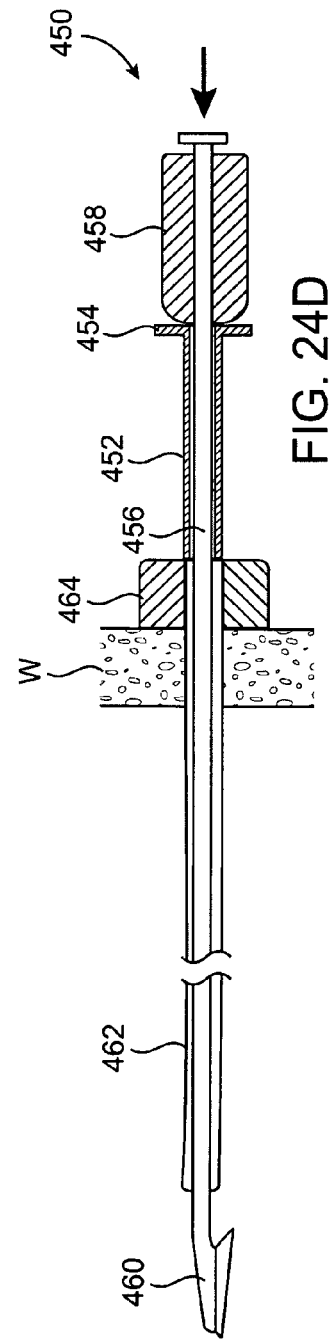
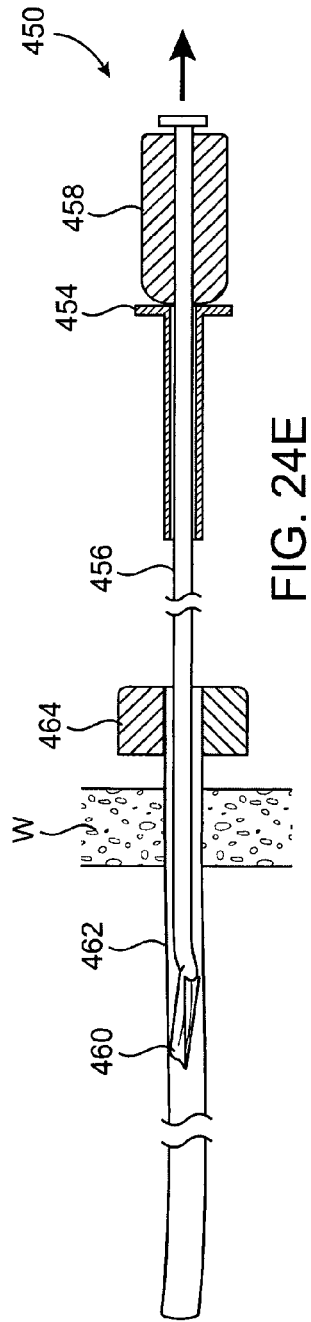

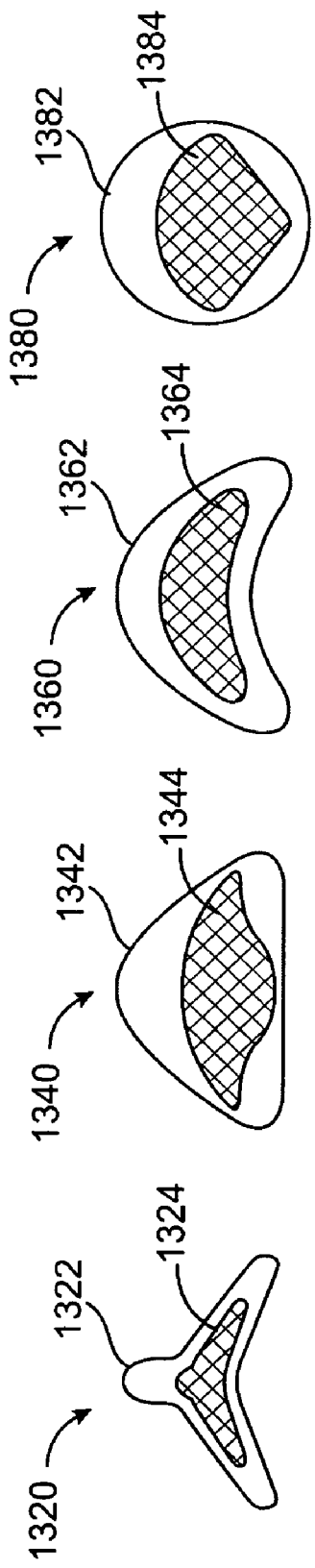

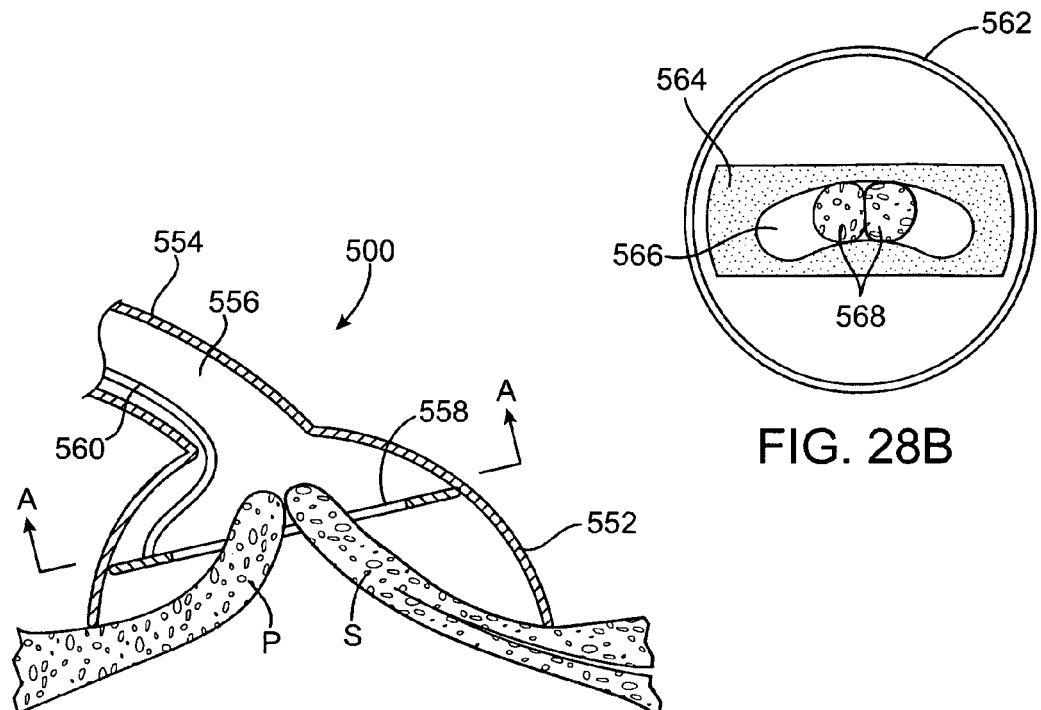
FIG. 28A
FIG. 28B
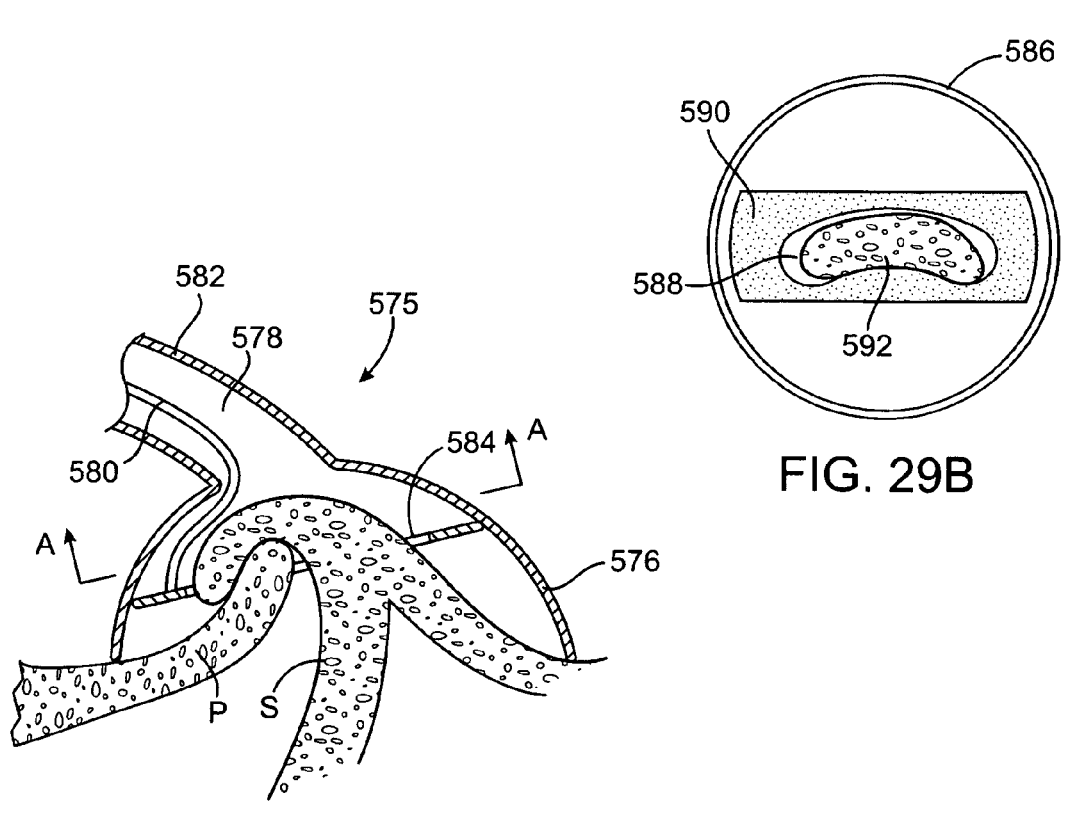
FIG. 29A
FIG. 29B

METHODS AND ELECTRODE APPARATUS TO ACHIEVE A CLOSURE OF A LAYERED TISSUE DEFECT

CROSS-REFERENCES TO RELATED APPLICATIONS

The present application is a non-provisional of U.S. patent application Ser. No. 60/670,535, filed Apr. 11, 2005, the full disclosure of which is incorporated herein by reference.

BACKGROUND OF THE INVENTION

The invention generally relates to medical devices and methods. More specifically, the invention relates to positioning closure devices, including energy based devices and methods for treatment of anatomic defects in human tissue, such as a patent foramen ovale (PFO), atrial septal defect (ASD), ventricular septal defect (VSD), patent ductus arteriosis (PDA), left atrial appendages (LAA), blood vessel wall defects and other defects having layered and apposed tissue structures.

The following is an example of how one particular type of anatomical defect, a PFO, is formed. Fetal blood circulation is very different from adult circulation. Because fetal blood is oxygenated by the placenta, rather than the fetal lungs, blood is generally shunted past the lungs to the peripheral tissues through a number of vessels and foramens that remain patent (i.e., open) during fetal life and typically close shortly after birth. For example, fetal blood passes directly from the right atrium through the foramen ovale into the left atrium, and a portion of blood circulating through the pulmonary artery trunk passes through the ductus arteriosus to the aorta. This fetal circulation is shown in FIG. 1.

At birth, as a newborn begins breathing, blood pressure in the left atrium rises above the pressure in the right atrium. In most newborns, a flap of tissue closes the foramen ovale and heals together. In approximately 20,000 babies born each year in the U.S., the flap of tissue is missing, and the hole remains open as an atrial septal defect (ASD). In a more significant percentage of the population (estimates range from 5% to 20% of the entire population), the flap is present but does not heal together. This condition is known as a patent foramen ovale (PFO). Whenever the pressure in the right atrium rises above that in the left atrium, blood pressure can push this patent channel open, allowing blood to flow from the right atrium to the left atrium. Blood shunting also occurs in a patent ductus arteriosis (PDA), where a tubular communication exists between the pulmonary artery and the aorta. The PDA typically closes shortly after birth.

Patent foramen ovale has long been considered a relatively benign condition, since it typically has little effect on the body's circulation. More recently, however, it has been found that a significant number of strokes may be caused at least in part by PFOs. In some cases, a stroke may occur because a PFO allows blood containing small thrombi to flow directly from the venous circulation to the arterial circulation and into the brain, rather than flowing to the lungs where the thrombi can become trapped and gradually dissolved. In other cases, a thrombus might form in the patent channel of the PFO itself and become dislodged when the pressures cause blood to flow from the right atrium to the left atrium. It has been estimated that patients with PFOs who have already had cryptogenic strokes may have a risk of having another stroke.

Further research is currently being conducted into the link between PFO and stroke. At the present time, if someone with a PFO has two or more strokes, the healthcare system in the United States may reimburse a surgical or other interventional procedure to definitively close the PFO. It is likely, however, that a more prophylactic approach would be warranted to close PFOs to prevent the prospective occurrence of a stroke. The cost and potential side-effects and complications of such a procedure must be low, however, since the event rate due to PFOs is relatively low. In younger patients, for example, PFOs sometimes close by themselves over time without any adverse health effects.

Another highly prevalent and debilitating condition, chronic migraine headache, has also been linked with PFO. Although the exact link has not yet been explained, PFO closure has been shown to eliminate or significantly reduce migraine headaches in many patients. Again, prophylactic PFO closure to treat chronic migraine headaches might be warranted if a relatively non-invasive procedure were available.

Currently available interventional therapies for defect closure are generally fairly invasive and/or have potential drawbacks. One strategy is simply to close a defect during open heart surgery for another purpose, such as heart valve surgery. This can typically be achieved via a simple procedure such as placing a stitch or two across the defect with vascular suture. Performing open heart surgery purely to close an asymptomatic PFO or even a very small ASD, however, would be very hard to justify.

A number of interventional devices for closing defects percutaneously have also been proposed and developed. Most of these devices are the same as or similar to ASD closure devices. They are typically "clamshell" or "double umbrella" shaped devices which deploy an area of biocompatible metal mesh or fabric (ePTFE or Dacron, for example) on each side of the atrial septum, held together with a central axial element, to cover the defect. This umbrella then heals into the atrial septum, with the healing response forming a uniform layer of tissue or "pannus" over the device. Such devices have been developed, for example, by companies such as Nitinol Medical Technologies, Inc. (Boston, Mass.) and AGA Medical, Inc. (White Bear Lake, Minn.). U.S. Pat. No. 6,401,720 describes a method and apparatus for thoracoscopic intracardiac procedures which may be used for treatment of PFO.

Although available devices may work well in some cases, they also face a number of challenges. Relatively frequent causes of complications include, for example, improper deployment, device embolization into the circulation and device breakage. In some instances, a deployed device does not heal into the septal wall completely, leaving an exposed tissue which may itself be a nidus for thrombus formation. Furthermore, currently available devices are generally complex and expensive to manufacture, making their use for prophylactic treatment of PFO and other defects impractical. Additionally, currently available devices typically close a PFO by placing material on either side of the tunnel of the PFO, compressing and opening the tunnel acutely, until blood clots on the devices and causes flow to stop.

Research into methods and compositions for tissue welding has been underway for many years. Of particular interest are technologies developed by McNally et. al., (as shown in U.S. Pat. No. 6,391,049) and Fusion Medical (as shown in U.S. Pat. Nos. 5,156,613; 5,669,934; 5,824,015 and 5,931,165). These technologies all disclose energy delivery to tissue solders and patches to join tissue and form anastomoses between arteries, bowel, nerves, etc. Also of interest are a number of patents by inventor Sinofsky, relating to laser suturing of biological materials (e.g., U.S. Pat. Nos. 5,725,522; 5,569,239; 5,540,677 and 5,071,417). None of these disclosures, however, show methods or apparatus suitable for positioning the tissues of an anatomic defect for welding or for delivering the energy to an anatomic defect to be welded. These disclosures do not teach methods that would be particularly useful for welding layered tissue structures such as PFOs, nor do they teach bringing together tissues of a defect such that a tissue overlap is created that can then be welded together.

Causing thermal trauma to close a patent foramen ovale has been described in two patent applications by Stambaugh et al. (PCT Publication Nos. WO 99/18870 and WO 99/18871). The intent is to eventually cause scar tissue formation which will close the PFO. Blaeser et al. (U.S. Patent Publication US2003/0208232), describes causing trauma, or abrading, and holding the abraded tissue in apposition to allow the tissue to heal together. Using such devices and methods, the PFO typically remains patent immediately after the procedure, or abrasion, and only closes sometime later, or is treated and then held together to heal over time. Frequently, scar tissue may fail to form or may form incompletely, resulting in a still patent PFO.

In addition to PFO, a number of other anatomic tissue defects, such as other ASDs, ventricular septal defects (VSDs), patent ductus arteriosis (PDA), aneurysms and other blood vessel wall defects, atrial appendages and other naturally occurring cavities within which blood clots can form, and the like cause a number of different health problems (note that the term "defect" may include a naturally occurring structure that results a potential health risk such as the clot forming in the atrial appendage). U.S. patent application Ser. No. 2004/0098031 (Van der Burg), and U.S. Pat. No. 6,375,668 (Gifford) and U.S. Pat. No. 6,730,108 (Van Tassel et al.), the full disclosures of which are incorporated herein by reference, disclose a variety of techniques and devices for treating anatomic defects. In addition, the inventors of the present invention have described a number of improved devices, methods and systems for treating a PFO, many of which may be adapted for treating other anatomic tissue defects as well. For example, related patent applications assigned to the assignee of the present invention include U.S. patent application Ser. No.: 10/665,974, filed on Sep. 16, 2003; Ser. No. 10/679,245, filed Oct. 2, 2003; Ser. No. 10/952,492, filed Sep. 27, 2004; Ser. No. 10/873,348, filed on Jun. 21, 2004; Ser. No. 11/049,791, filed on Feb. 2, 2005; Ser. No. 10/787,532, filed Feb. 25, 2004; Ser. No. 10/764,148, filed Jan. 23, 2004; Ser. No. 10/811,228, filed Mar. 26, 2004; and U.S. Provisional Application 60/670,535, filed Apr. 11, 2005, the full disclosures of which are incorporated herein by reference.

Despite improvements made thus far, it would be advantageous to have even further improved methods, systems, and apparatus for treating anatomic tissue defects such as PFOs and the other anatomic structures mentioned above. Ideally, such methods and apparatus would help position a closure device so that a complete seal of a PFO or other anatomic tissue defect can be achieved reliably and in a predictable fashion. Also, such devices and methods would leave no foreign material (or very little material) in a patient's heart. Furthermore, such methods and apparatus would preferably be relatively simple to manufacture and use, thus rendering prophylactic treatment of PFO and other tissue defects a viable option. Ideally, such methods and apparatus could also be used in a minimally invasive manner, with low profile for ease of introduction into the body, while effectively closing the PFO quickly, effectively and without causing damage to other portions of the body. When success of the closure procedure can be well predicted, physicians are more likely to recommend such a procedure prophylacticly. At least some of these objectives will be met by the present invention.

BRIEF SUMMARY OF THE INVENTION

The present invention provides apparatus, systems and methods for treating anatomic defects in human tissues, particularly defects involving tissue layers where it is desired to weld or fuse the layers together, such as a patent foramen ovale (PFO). The methods will also find use with closing a variety of other defects which may or may not display layered tissue structures, such as atrial septal defects, ventricular septal defects, patent ductus arteriosis, left atrial appendages, blood vessel wall defects, and the like. For the treatment of PFOs, the apparatus will usually comprise endovascular/intravascular catheters having an elongate catheter body with a proximal end and a distal end. A housing may be positioned at or near a distal end of the catheter body, where the housing has an opening for engaging a tissue surface where the tissue defect may be present. Usually, the housing will be connectable to a vacuum source to enhance engagement of the housing against the tissue, and an energy transmission member, such as an electrode, may be positioned at or near the opening in the housing to apply energy to the tissue to effect welding and closure. For purposes of this disclosure, the terms sealing, closing, welding, fusing are used interchangeably to describe bringing tissues of a defect together so as to result in a substantial seal e.g. no physiologic leak of biological fluid or operator infused fluid across the sealed area. Although a variety of mechanisms may work to achieve this, the sealing or closing of the defect can occur via the presence or absence of a variety of biologic processes, some of which may be fusion or lamination of the tissue cells, layers or collagen, expression/combination of factors from the tissue that are expressed upon application of energy, denaturation and renaturation of tissue elements, crosslinking, necrosis or partial necrosis or other cellular phenomena present at the treatment site upon application of the energies described herein, or combinations thereof.

Alternatively, instead of an electrode, the suction housing may be adapted for passage of a closure device such as a clip or fixation element that may be placed through the tissue of the defect while it is stabilized by the suction housing. The following description will often focus on PFO treatment, but at least many of the inventive embodiments may be employed for treating other tissue defects and in other contexts.

In a first aspect of the present invention, an apparatus for fusing a layered tissue structure comprises a catheter body with proximal and distal ends, a housing on a distal portion of the catheter body and an energy transmission member associated with the housing. The energy transmission member is configured to distribute energy over a predetermined pattern.

In a second aspect of the present invention, an apparatus for fusing a layered tissue structure comprises a catheter body having both proximal and distal ends, a vacuum housing on a distal portion of the catheter body and an energy transmission member disposed on or within the vacuum housing. The energy transmission member also has at least one opening which is adapted to receive tissue when a vacuum is applied to the housing.

In a third aspect of the present invention, a method for fusing apposed layered tissue structures comprises advancing a closure device at a first treatment site having apposed layers of tissue, applying energy from the closure device to the layers of tissue and controlling the applied energy to minimize creation of aberrant conductive paths and to enhance fusing at of the layers. The method may further include cooling down the closure device and the apposed layers to tissue and releasing the closure device away from the tissue structure. Often the method includes a closure device comprising a catheter body having a proximal end and a distal end, a housing on the distal portion of the catheter body and an energy transmission member associated with the housing is configured to deliver energy over a predetermined pattern.

In a fourth aspect of the present invention, a method generally takes the same form as the method previously described, except here, the method comprises a catheter body having a proximal and distal end, a vacuum housing on a distal portion of the catheter body and an energy transmission member disposed on or within the vacuum housing and having an opening adapted to receive tissue when a vacuum is applied to the housing.

In the first four aspects of the present invention, as described above, various embodiments are contemplated. For example, the energy transmission member may be disposed over an opening in the housing and is adapted to allow the housing to appose the layered tissue structure. Often the energy transmission member is collapsible and typically has an active surface. In some embodiments, the energy transmission member also has an inactive surface. A non-conductive mask may be used to define the active surface which may be variable. The non-conductive mask can be connected with the active region and forms an insulated region between the housing and the energy transmission member.

Often, the energy transmission member is an electrode, and the geometry of the energy transmission member substantially approximates the layered tissue structure to be treated. In some embodiments, the layered tissue structure is a patent foramen ovale (PFO) and the energy transmission member can treat PFOs ranging in size from about 1 mm to about 30 mm. The electrode may be adapted to penetrate tissue.

In other embodiments, the energy transmission member comprises a band which can be shaped in a number of ways, including elliptical, circular, rectangular, triangular and combinations thereof. Other patterns for the band include an undulating wave-like pattern and the energy transmission member can also comprise a mesh, lobes or a bar. In the case of a bar, the bars have a length and a width and the bar length is often greater than the bar width. Also, the bars may have first and second regions which are hingedly connected or oppositely charged and adapted to deliver bipolar energy. The oppositely charged regions may alternatate.

In still other embodiments, the bars may interdigitate with one another or they may be substantially parallel to each other. The bars may comprise an opening which can be a slit and the slit width is usually less than the bar width. Some embodiments include a guidewire lumen disposed in the catheter body, passing through the housing and the lumen has an exit port between the bars. A ramp may be employed near the distal exit port. Often, a vacuum may be applied through the bars which have been adapted so that tissue adherence is minimized and also allows a smooth interface with the layered tissue structure. The bars can also be adapted to form an edge from which energy is delivered.

The energy transmission member is usually biased toward a proximal portion of the housing in order to maximize the physical distance between the AV node of the human heart and an active portion of the energy transmission member when it is positioned over the layered tissue structure for treatment. General features may include coating or plating the energy transmission member for either enhanced electrical or radiopaque characteristics. Also, a guidewire port may be disposed adjacent to the energy transmission member and a vacuum can be applied through the transmission member. Often, struts in the energy transmission member connect it with the housing, or elastic elements flexibly connect the two together. Also, a thermocouple may be disposed near the energy transmission member in some embodiments and the housing can be adapted to allow fluid delivery to the layered tissue structure when the housing is apposed with the tissue.

In another aspect of the present invention, an apparatus for fusing a layered tissue structure comprises an elongated catheter body with a proximal and distal end, and an energy transmission member connected with the elongated body. The energy transmission member is adapted to appose the layered tissue structure and also adapted to deliver bipolar energy sufficient to fuse the structure. Often the energy transmission member is a collapsible electrode which may be adapted to penetrate tissue. The energy transmission member has a geometry which substantially approximates the layered tissue structure to be treated and can treat a PFO with a size ranging from about 1 mm to about 30 mm.

In another aspect of the present invention, a method is disclosed which is similar to that previously described, except that in this aspect, the closure device comprises an elongated catheter body with a proximal and distal end as well as an energy transmission member. The energy transmission member is connected with the catheter and adapted to appose the layered tissue structure and fuse the structure upon.

In both aspects of the preceding apparatus and method, the energy transmission member may comprise a ring, a mesh or bars. Often, the apparatus comprises a guidewire lumen axially disposed in the catheter body with a distal exit port adjacent to the energy transmission member. A ramp may be located near the distal exit port and a vacuum may be applied through the energy transmission member. The energy transmission member is also adapted to minimize adherence with tissue. It also may be biased toward a proximal portion of the catheter body in order to maximize the physical distance between the AV node of the heart and the energy transmission member when it is positioned adjacent to the layered tissue structure to be treated. Optionally, the energy transmission member may be coated or plated for enhanced electrical characteristics or radiopacity. Often, a vacuum is applied through the energy transmission member and a thermocouple may be adjacent to the energy transmission member.

In another aspect of the present invention, a system for fusing layered tissue structure comprises a treatment catheter having an energy transmission member adapted to deliver energy deliver energy to the layered tissue structures and a controller connected to the treatment catheter. The controller is programmed to vary an energy delivery parameter from the energy transmission member to the layered tissue structure to minimize creation of aberrant conductive paths and enhance fusing of adjacent tissue layers in the layered tissue structure.

The controller can be programmed to vary at least one parameter such as power, pulse rate, frequency and duration. The energy delivery parameter is typically varied in response to an algorithm which may depend upon a tissue response parameter. The system often includes one or more sensors for measuring a tissue response parameter while the size of the energy transmission member and/or the amount of energy delivered by the controller are selected to create a weld lesion having an effective size in the range from about 5 $mm^2$ to 90 $mm^2$. In the case of a patent foramen ovale, the size of the energy transmission member and/or the amount of energy delivered by the controller are selected to create a weld lesion adequate to treat a PFO ranging in size from about 1 mm to about 30 mm.

In another aspect of the present invention, a method for fusing apposed layered tissue structures comprises applying energy to the layered tissue structure and controlling the applied energy to minimize creation of aberrant conductive paths and enhance fusing of adjacent tissue layers in the tissue structure. Controlling the energy typically involves varying over time at least one parameter such as power, pulse rate, frequency, rate of increase, rate of decrease or duration.

Typically, the power parameter is varied at least partially in response to an algorithm which may be dependent upon a tissue response parameter. The energy is also controlled to create a weld lesion having a predetermined size, typically in the range of 2 mm$^2$ to 400 mm$^2$, and often in the range of 5 mm$^2$ to 90 mm$^2$. Power is usually increased or decreased during a portion of the treatment cycle. If a tissue response parameter is used to control the power parameter, common tissue responses include tissue temperature, impedance and moisture.

The method also comprises controlling power by applying power at an initial level of $P_0$, increasing power to a higher level of $P_1$ over a time period of $t_1$ and then terminating power after a time period $t_2$ if no impedance spike occurs. The method may further comprise reducing or terminating power if an impedance spike occurs, reapplying power at a lower level $P_2$ over a time period $t_3$ and terminating the reapplied power if an impedance spike occurs. The method also can comprise controlling power by applying power at an initial level of $P_0$ and decreasing power if an impedance spike occurs. Power may be decreased if the impedance spike is observed within a predetermined time period, and power is terminated after a predetermined cumulative treatment time has passed. Other treatment parameters which may be used to control the procedure are selected based on patient characteristics and may include tissue characteristics and the nature of the defect being treated, which can be a patent foramen ovale.

In still another aspect of the present invention, a method for fusing apposed layered tissue structures comprises applying power to the apposed layered tissue structure an initial level $P_0$, measuring tissue impedance including initial impedance $Z_0$ and increasing power by an amount k to a higher level after a given duration of time $t_1$ until a maximum power level $P_{max}$ is obtained. Power application is terminated if an impedance spike occurs and power has been applied for a given duration of time $t_2$ or longer.

Additional steps comprise temporarily stopping application of power if an impedance spike occurs and power has been applied for less than a given duration of time $t_2$ and re-applying power to the tissue structure at a power level $P_1$ lower than $P_0$, if total power delivery time is less than $t_3$, where $t_3$ is less than $t_2$. Power may be increased by an amount 2k if impedance has not exceeded its minimum value $Z_0$ by a given amount r after a time $t_4$, where $t_4$ is greater than $t_1$.

Additionally, the method may comprise increasing power by another amount 2k if impedance has not exceeded its minimum value $Z_0$ by a given amount r after a time $t_4$. Power application is terminated when an impedance spike occurs and power has been applied for a given duration of time $t_2$ or longer. Power is also stopped, temporarily if an impedance spike occurs and power has been applied for less than a given duration of time $t_2$. Power is then reapplied to the tissue structure at a power level $P_1$, and lower than $P_0$, if total power delivery time is less than $t_3$, where $t_3$ is less than $t_2$.

The method further comprises applying power at a level equal to $P_1+2k$ when total power application time prior to decreasing power to $P_1$ exceeds time $t_3$. Power is increased if impedance has not exceeded its minimum value after power was decreased to $P_1$ by r after a time $t_4$, and power is terminated if an impedance spike occurs and power has been applied for a given duration of time $t_2$ or longer. Again, power may be temporarily stopped if an impedance spike occurs and power has been applied for less than a given duration of time $t_2$. Power is then re-applied to the tissue at a power level selected from the group consisting of $P_1$, $P_1+2k$ and $P_1+4k$.

Again, if an impedance spike occurs, power application is terminated. In all cases, power application is terminated after application of power for a maximum time $t_{max}$.

BRIEF DESCRIPTION OF THE DRAWINGS

FIGS. 3A-3D show various orientations of PFOs.

FIGS. 4A-4D show how a treated PFO may not be fully sealed.

FIGS. 15A-15D shows a positioning device with retractable whiskers.

FIGS. 16A-16E illustrates a positioning device utilizing a looped wire design.

FIGS. 24A-24E show how the collapsing introducer of FIG. 23 is used.

FIGS. 25C-25I show a bottom view of several housing and electrode configurations.

FIGS. 26-36 show various ways a therapeutic element of a treatment device can appose defect tissue.

DETAILED DESCRIPTION OF THE INVENTION

Devices, systems, and methods of the present invention generally provide for treatment of anatomic defects in human tissue, such as a patent foramen ovale (PFO), atrial septal defect (ASD), ventricular septal defect (VSD), left atrial appendage (LAA), patent ductus arteriosis (PDA), vessel wall defects and/or the like through application of energy. The present invention is particularly useful for treating and fusing layered tissue structures where one layer of tissue at least partly overlaps a second layer of tissue as found in a PFO. Therefore, although the following descriptions and the referenced drawing figures focus primarily on treatment of PFO, any other suitable tissue defects, such as but not limited to those just listed, may be treated in various embodiments.

I. PFO Anatomy

Figure 1:
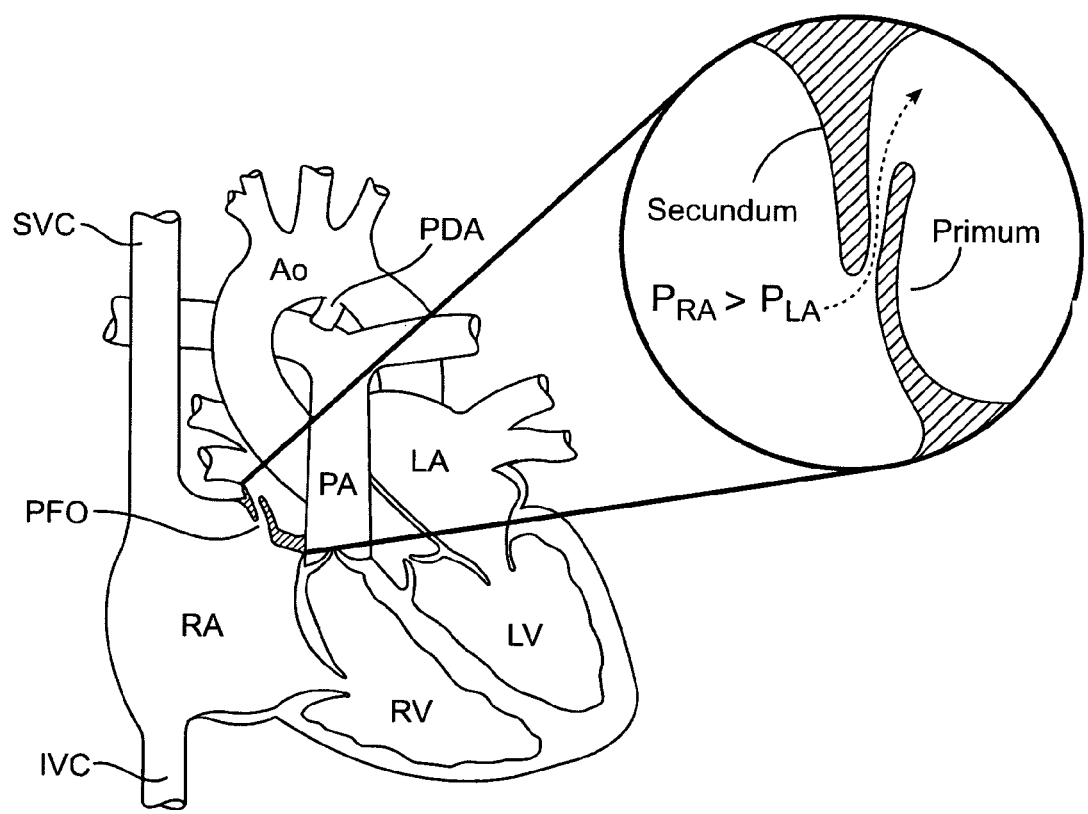
FIG. 1 illustrates the anatomy of fetal circulation, including a PFO and PDA.

As mentioned in the background section above, FIG. 1 is a diagram of the fetal circulation. The foramen ovale is shown PFO, with an arrow expanded view demonstrating that blood passes from the right atrium RA to the left atrium LA in the fetus. After birth, if the foramen ovale fails to close (thus becoming a PFO), blood may travel from the right atrium RA to the left atrium LA or vice versa, causing increased risk of stroke, migraine and possibly other adverse health conditions, as discussed above.

Figure 2A:
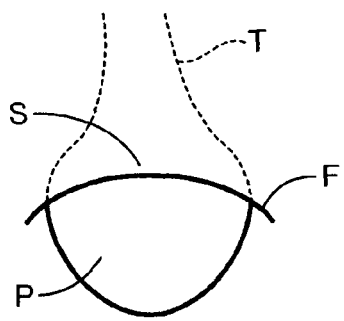
FIGS. 2A-2I show various anatomies of a PFO.
Figure 2B:
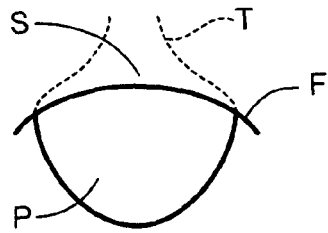
Figure 2C:
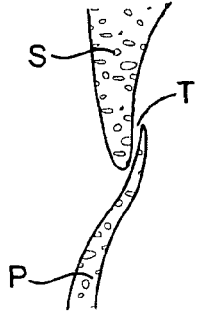
Figure 2D:
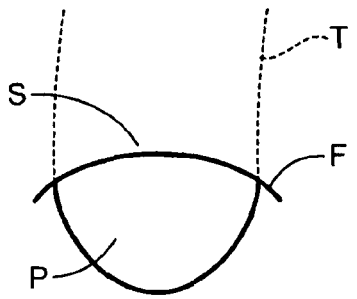
Figure 2E:
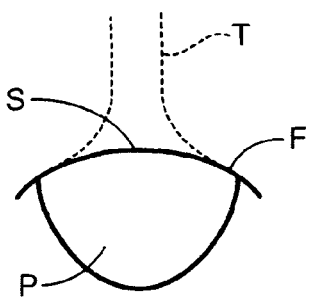
Figure 2F:
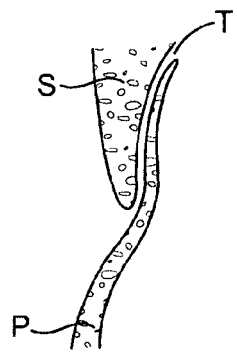
Figure 2G:
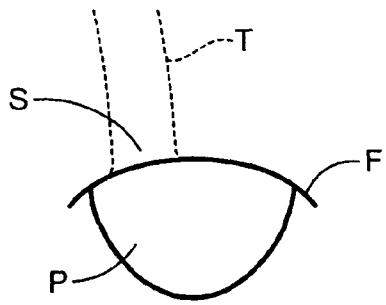
Figure 2H:
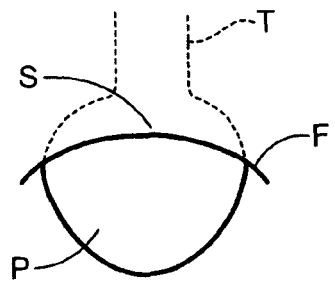
Figure 2I:
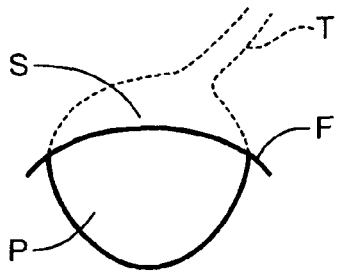
Figure 5A:
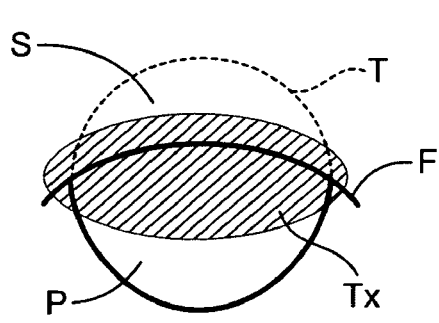
FIGS. 5A-5F show various treated regions that successfully seal the PFO.
Figure 5B:
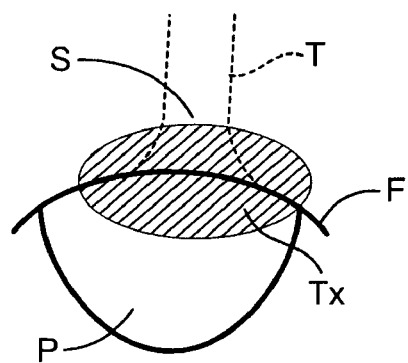
Figure 5C:
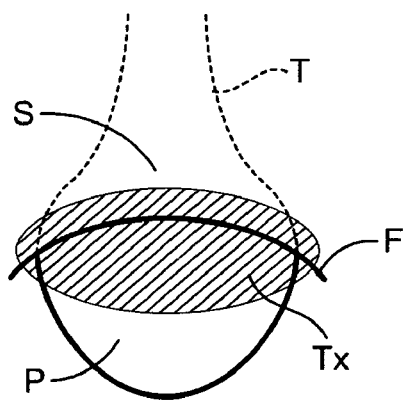
Figure 5D:
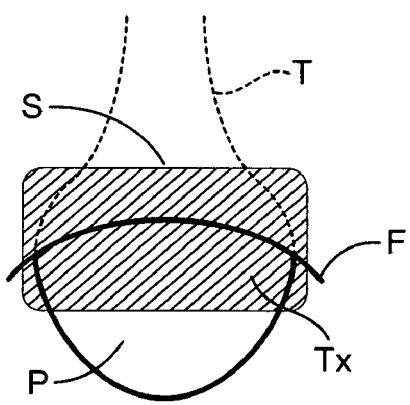
Figure 5E:
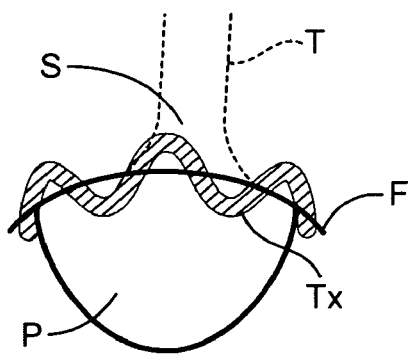
Figure 5F:
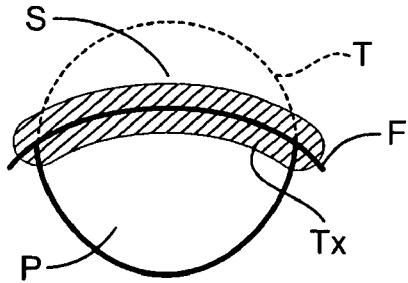

FIGS. 2A-2I illustrate various PFO anatomies. For example, FIG. 2A shows the secundum S overlapping with the primum P to form a frown line F which is the entrance the PFO tunnel T and here, which is narrow and slightly offset. The PFO tunnel T may also be short and shallow as illustrated in FIG. 2B and cross-sectional view in FIG. 2C, or the tunnel T may be wide and long as shown in FIG. 2D. FIG. 2E and cross-sectional view FIG. 2F show a PFO tunnel T that is long. Other PFO tunnel T anatomies include an offset tunnel as in FIG. 2G, or an initially wide tunnel T which narrows in FIG. 2H or an initially wide tunnel T that narrows and is offset as illustrated in FIG. 2I.

In addition to tunnel variations, the opening or frown F of the PFO and height of the PFO limbus can also vary. FIG. 3A refers to anatomic locations for FIGS. 3B-3D where superior points toward the head, inferior points toward the feet, posterior is toward the back of the body and anterior is toward the front. FIG. 3B shows the overlap of the primum P with the secundum S forming a frown line F which is the entrance to the PFO tunnel T. In FIG. 3B, the PFO tunnel T has an anterior orientation, while in FIG. 3C the PFO is inferior with an anterior tunnel T and FIG. 3D shows a superior PFO with a posterior tunnel T.

II. Placement

Given the anatomical variations of a PFO, using a traditional guidewire to guide a closure device to the defect for treatment may not result in optimal placement all of the time. For example, in FIG. 4A, a traditional guidewire GW placed through a wide PFO tunnel T may direct the closure device to a treatment region Tx that only includes a portion of the tunnel opening F, leaving an untreated region UTx that results in a leak L, as shown in FIG. 4B.

Similarly, as illustrated in FIGS. 4C and 4D, a single strand guidewire GW placed through a deeper PFO tunnel T that is somewhat offset, may align the device with the location of the tunnel T, but not let the operator know that the device is not placed in a position to affect the mouth or opening of the tunnel F, and may therefore result in a treated region Tx that falls short of sealing off the mouth of the tunnel, resulting in a leak path L.

Proper positioning is achieved when the closure device is placed optimally in relation to the defect to deliver the desired closure device. Closure of the defect following accurate placement of the device in a variety of PFO anatomies is illustrated in FIGS. 5A-5F. These figures show the overlap of the primum P with the secundum S to form a frown line F which is the opening to the PFO tunnel T. Various treatment regions Tx are shown which successfully close the PFO tunnel T. Accurate placement allows the therapeutic device to be more precise, and in addition, in the case of energy delivery catheters to seal the PFO, deliver the energy just to the opening on the defect so as to minimize the location and amount of energy delivered to the heart tissue. As illustrated in FIGS. 5A-5F, various electrode configurations and treatment zones can be employed accurately with use of the present invention.

III. Positioning

In any of these procedures, a key aspect to performing closure of an anatomic defect is positioning the catheter or treatment device at the optimal location over the defect to be treated. Failure to place the device in the optimal location can result in incomplete closure of the defect, and require either a repeat application of the closure mechanism, or an additional intervention (e.g. second procedure). For example if a traditional single strand guidewire is placed through a PFO defect with a long tunnel, or a wide tunnel, it is difficult to predict, where in that tunnel the guidewire is going to reside and therefore even if a closure catheter is tracked over the wire that is through the PFO, it may not be directed to the center of the tunnel (in the case of a wide PFO), or to the mouth of the tunnel (in the case of a longer PFO tunnel). Various other misalignments can also occur depending on the size, width, angle, and/or depth of the targeted defect.

Various steps may be undertaken prior to performing a procedure to close a PFO, including sizing the defect, determining the orientation of the defect, assessing the depth of the defect, and determining any related or adjacent anatomic features such as a septal aneurysm. PFOs can range in size from about 1 mm to 30 mm although they are typically in the range from about 3 mm to 26 mm. Sizing of the defect could be accomplished by placing gradations or markers on a sizing device or a series of calibrated sizers could be utilized. Any of these can be adapted to be radiopaque or echogenic and therefore fluoroscopy, intravascular ultrasound, TEE, ICE and other visualization techniques may be employed to visualize and determine the foregoing so that the physician can better determine how best to size and place the closure device to achieve closure of the defect. For example, radiopaque markers mounted on a balloon inflated in the PFO would permit the PFO tunnel diameter to be observed and estimated under a fluoroscope. Other apparatus and methods for characterizing the tissue defect are described herein.

In addition, these visualization techniques may be employed in combination with the intravascular devices of the present invention to not only provide sizing information to the user, but in some cases provide a mechanical guide or rail, over which to accurately place a closure catheter. These features may be combined into one device, or a series of devices to assess the geometry of the PFO, place and position a closure device and ultimately deliver the closure therapy (clip, energy, sutures, etc.).

Figure 6:
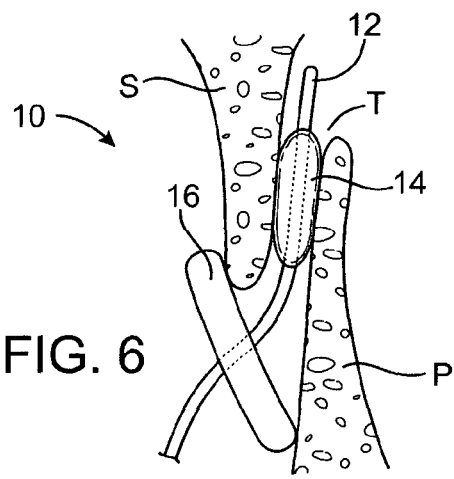
FIG. 6 shows a balloon properly positioning a closure device with respect to a layered tissue defect such as a PFO.

FIG. 6 illustrates a closure system 10 wherein a guiding member 12 such as a catheter shaft or guidewire is inserted into the PFO tunnel T created by the overlap of primum P and secundum S layers of tissue. An inflatable member 14 such as a balloon mounted on the guiding member 12 is then inflated thereby centering the guiding member 12 and closure device 16 with the tissue defect. The closure device may be advanced into apposition with the tissue defect by pushing the closure system 10 forward towards the defect, or a vacuum may be used to draw the tissue toward the closure device. Other tissue apposition apparatus and methods are discussed hereinafter. An example of a sizing/orientation apparatus is the PTS® Sizing Balloon Catheter available from NuMed, Hopkington, N.Y. The properly aligned closure device 16 can then successfully treat and close the defect. The combined apparatus allows sizing and or visual (radiographic, ultrasonic, etc.) feedback of PFO anatomy, as well as guiding features (such as over the wire placement of a closure catheter) so that closure catheters can be correctly positioned in the vicinity of a PFO or other anatomic defect to deliver a variety of closure devices including suture delivery catheters, clip delivery catheters, patch delivery catheters, energy welding catheters and the like. Examples closure devices include, but are not limited to a suturing device as described in U.S. Patent Publication 2005/0070923 (McIntosh); a clip in U.S. Patent Publication 2005/0119675 (Adams); a transeptal puncture in publication WO 05/046487 (Chanduszko); a coil electrode in publication WO 05/074517 (Chanduszko); a clip in U.S. Patent Publication 2005/0187568 (Klenk); a transeptal puncture and electrode catheter in U.S. Patent Publication 2004/0243122 (Auth); and a gathering clip in publication WO 05/027753 (Brenzel); the full disclosures of which are incorporated herein by reference.

Figure 7A:
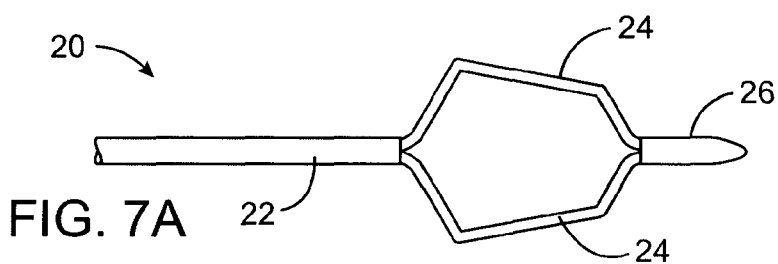
FIGS. 7A and 7B show tapered elongated members or a tapered balloon on the distal end of a catheter used to position the catheter.
Figure 7B:
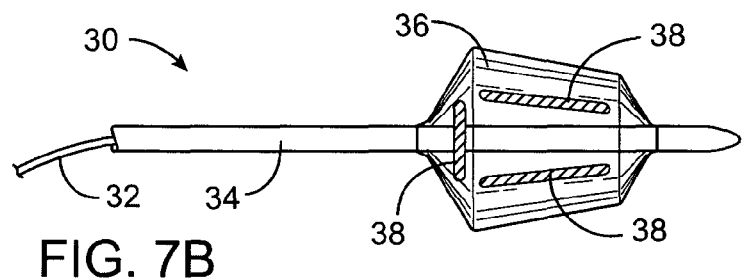

Another embodiment of a positioning device is shown in FIGS. 7A and 7B. In FIG. 7A, positioning device 20 comprises a guiding member 22 such as a catheter or guidewire with a tapered set of elongated members 24 near the distal tip 26 of the device. The positioning device 20 may then be advanced into the PFO tunnel and it is automatically centered as the tapered elongated members engage the tunnel walls. In addition to positioning, the device also facilitates sizing of the defect. A closure device may then be introduced over the guiding member 22 so that it is properly positioned and a closure treatment is then applied to the defect. In another embodiment shown in FIG. 7B, a positioning device 30 comprises a catheter 34 having an expandable member 36 such as a balloon disposed near the distal end of the device. The expandable member is expanded in the PFO tunnel resulting in the centering of the positioning of the device. Radiopaque markers 38 are disposed on the balloon 36 allowing a physician to size the defect and observe position. Once properly positioned, a closure device is then delivered over the positioning device to the defect so that a closing treatment may be applied. The tapered elongated members 24 from FIG. 7A may also be incorporated into this embodiment to assist with positioning of the device. The catheter 34 may also have a guidewire lumen to allow use of a guidewire 32.

Figure 8:
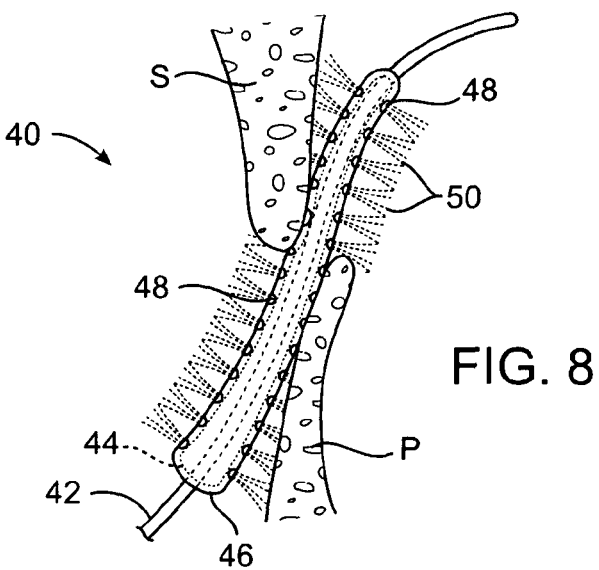
FIG. 8 shows a dual layer balloon in a layered tissue defect.

With reference now to FIG. 8, a dual layer balloon is used to position and size the tissue defect. A positioning device 40 has an inner balloon 44 and an outer balloon 46 mounted on the distal end of a catheter 42. The catheter 42 is advanced into the tunnel of a PFO and the inner balloon 44 is then inflated until it engages the walls of the of tunnel, thereby centering the device in the tunnel. The outer balloon 46 may then be inflated with contrast media and holes 48 in the outer balloon allow contrast media to weep out 50. Hole geometry may be varied to provide appropriate contrast flow rates. This may be observed under fluoroscopy and therefore the tissue defect anatomy and dimensions can be estimated including tunnel length, as well as allowing verification that the device is properly positioned. A closure device is then introduced over the positioning catheter to the defect and a closure treatment is applied. Visualizing the contrast media also helps to verify that the closure device is properly positioned with respect to the defect prior to treatment.

Figure 9:
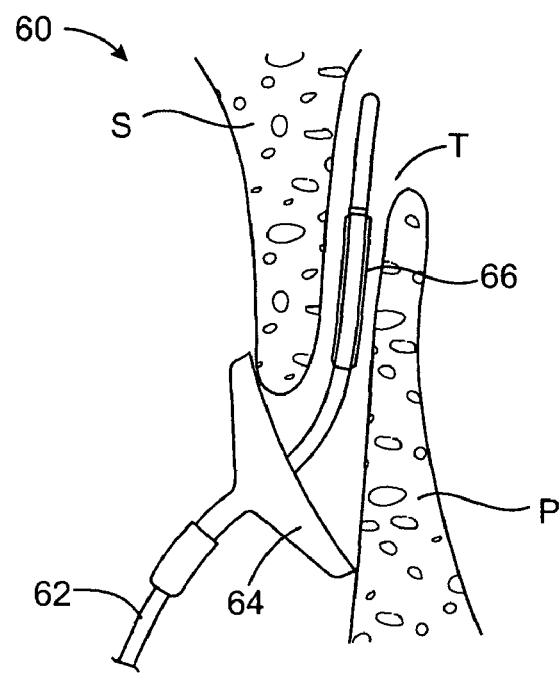
FIGS. 9-9A illustrate how expandable mechanical elements may be used to properly position a closure device at a layered tissue defect.
Figure 9A:
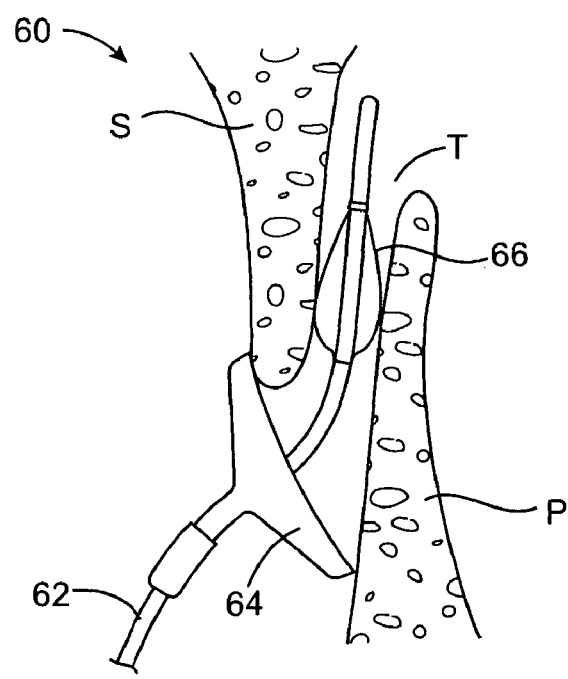

Another embodiment of a mechanical expansion device used for positioning is shown in FIGS. 9 and 9A-9D. In FIG. 9, a closure system 60 is illustrated having a catheter 62 with mechanical positioning elements 66 in the collapsed position, mounted on the distal end of the catheter 62. The catheter 62 and positioning elements 66 are advanced into the tunnel T of the PFO and then the mechanical elements 66 are expanded until they engage the defect walls and the device is positioned as illustrated in FIG. 9A. A closure device 64 also disposed on the catheter 62 is therefore also simultaneously positioned against the tissue defect and then a treatment can be applied to close the PFO defect. FIG. 9A shows the closure system when the mechanical elements 66 are expanded and engaged with the PFO tunnel, T.

Figure 9B:
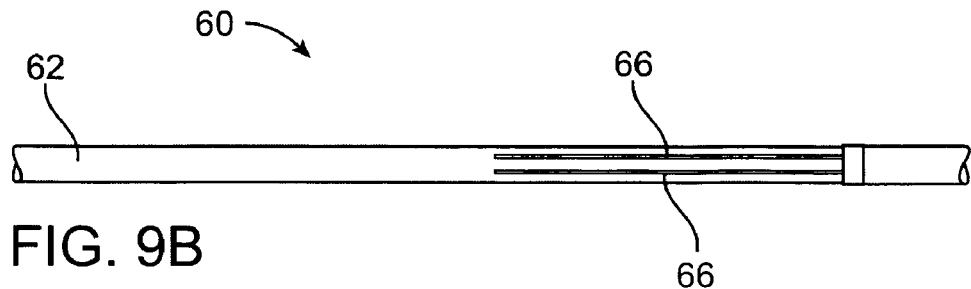
FIGS. 9B-9D show expandable mechanical elements on a catheter shaft.
Figure 9C:
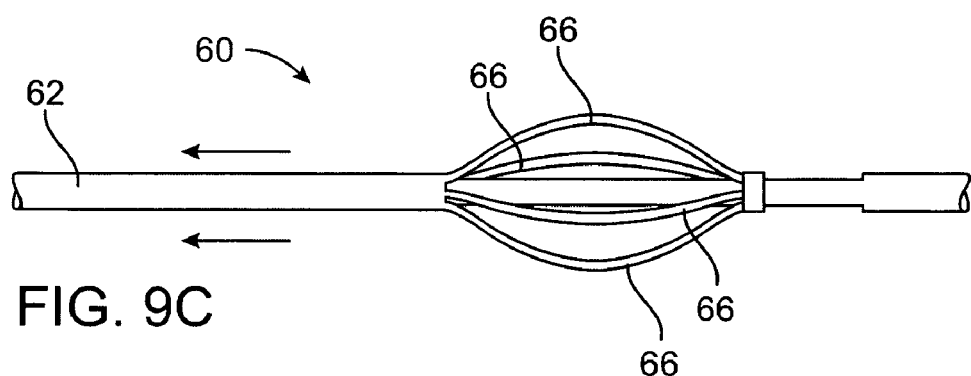
Figure 9D:
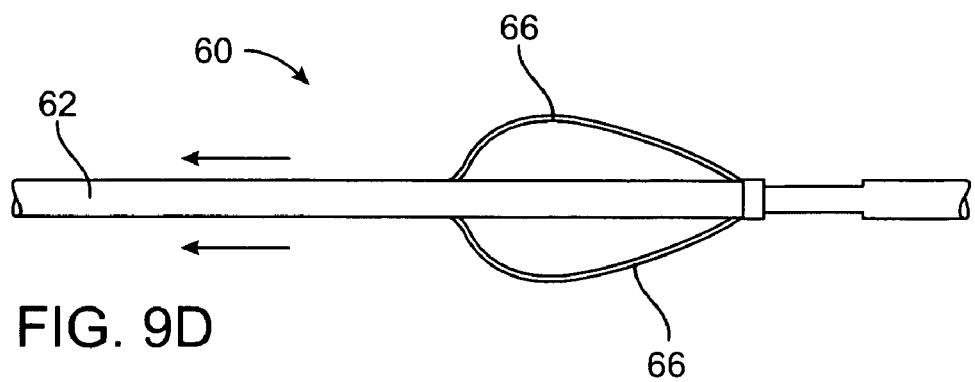

FIGS. 9B-9D illustrate how the mechanical expansion elements 66 function. In FIG. 9B the mechanical elements 66 are unexpanded and remain in a low profile position against the catheter 62. When the catheter 62 is actuated as shown by the arrows in FIG. 9C, the mechanical expansion members 66 flex and bow outward to various diameters depending on how far the catheter 62 is actuated. In FIG. 9C four expansion members are illustrated, although more or less may be employed, as shown in FIG. 9D where two members are shown. The expansion members may be fabricated from polymers or metals having a spring temper or superelastic alloys such as nitinol.

Figure 10A:
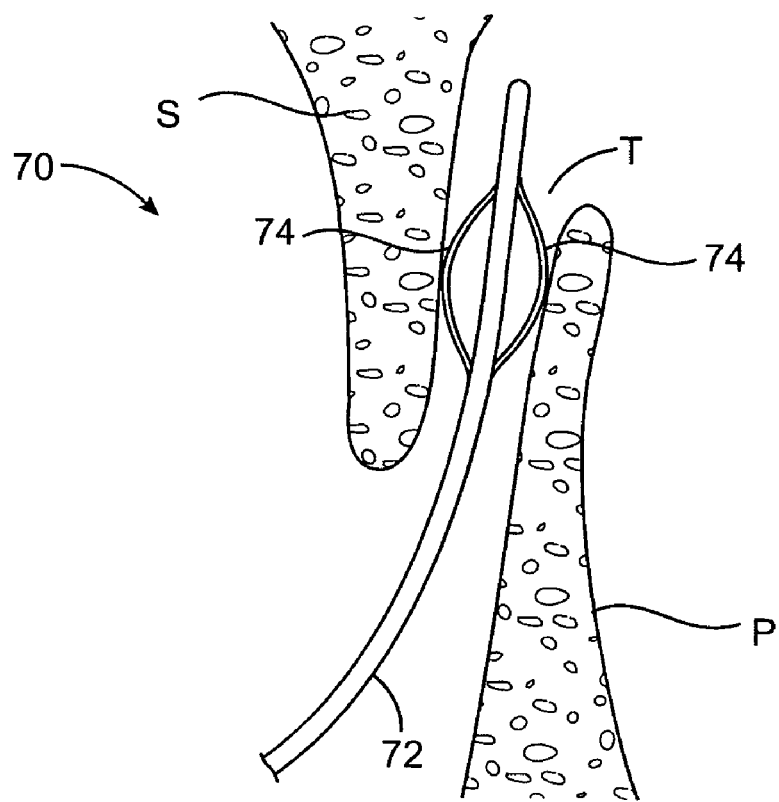
FIGS. 10A-10B show an alternative embodiment of expandable mechanical positioning elements.
Figure 10B:
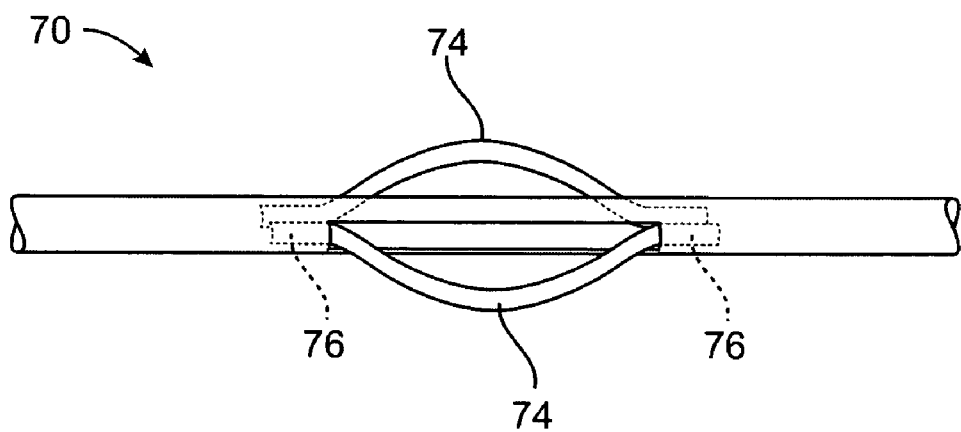

Another mechanical expansion embodiment is shown in FIGS. 10A and 10B. In FIG. 10A, a positioning device 70 comprises a catheter 72 which is introduced into the tunnel T of the PFO defect. Expansion members 74 are then expanded thereby properly positioning the device within the tunnel. In this embodiment, the expansion elements 74 are retractable into openings 76 in the catheter. The expansion elements 74 are actuated directly to control their expansion, and when unexpanded, have an even lower profile than the embodiment of FIG. 9C.

Figure 11:
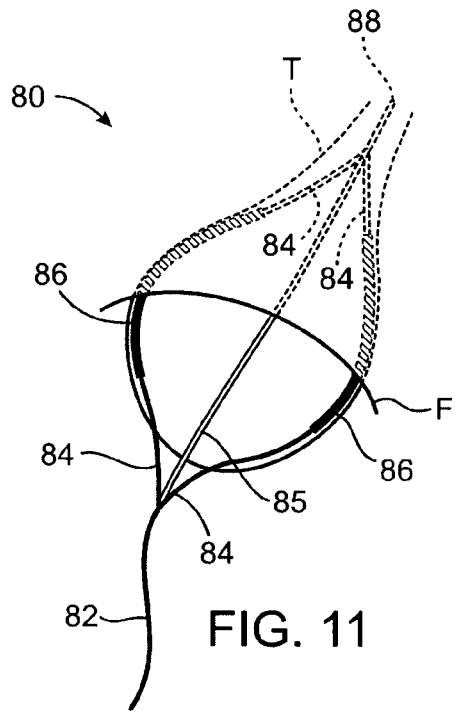
FIG. 11 shows how radiopaque markers on a flexible wire may be used to position a catheter and estimate tissue defect size.

With reference now to FIG. 11, a positioning device 80 may include single or multiple flexible members 84 with both ends fixed to an elongate member such as a catheter 82. A part of the catheter shaft 85 may act as a core member between the flexible members 84 to further add rigidity to the positioning device 80 to assist with its pushability toward and through a tissue defect. The positioning device 80 may be deployed through a closure device, or through a separate introducer catheter that is then removed, leaving the positioning device in place. Radiopaque markers 86 or coatings may be placed on various segments of the flexible members 84 to allow the user to view the orientation and spacing of the flexible members 84 and correlate them to the defect anatomy. For example, markers may be useful on the widest point of the flexible members to show the width of the PFO frown or opening, F, and may also continue along the length of the flexible members to help delineate the tunnel T (e.g. see the angle, show tunnel width, etc.). At least a portion of the flexible members are preferably placed between the tissue of the PFO with the main catheter 82 extending into or through the defect tunnel. The flexible members 84 extend laterally from the main body of the catheter to provide definition of the outer edges of the PFO, transitioning to define the location (angle) and size or width of the defect tunnel. The radiopaque markers 86 in FIG. 11 are visible under fluoroscopy and permit orientation of the defect and location of the frown or opening to be discerned based on observation of the geometry of the flexible members placed within the defect.

Figure 12:
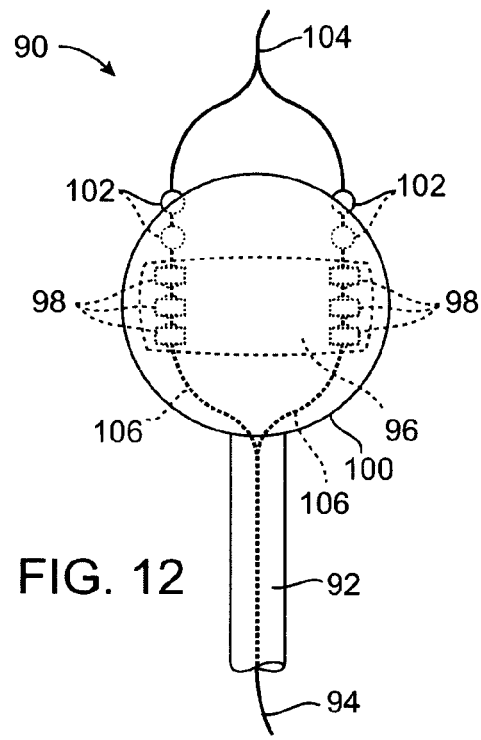
FIG. 12 shows an alternative embodiment of a treatment device with flexible wires used for positioning and radiopaque markers for sizing and indicating treatment region.

FIG. 12 shows how a treatment device may be used with a positioning device. In FIG. 12, a closure treatment catheter 90 has an elongate shaft 92 and a housing 100 on the distal end. A treatment region 96 is disposed within the housing 100 and radiopaque markers 98 outline the treatment area 96. A positioning device 94 is advanced to a layered tissue defect such as a PFO until the distal end 104 extends beyond the defect. Flexible elongate members 106 delineate the tunnel of the PFO and radiopaque markers 102 allow the physician to see the defect under fluoroscopy. The closure treatment catheter 90 is then advanced over the positioning device 94 until the radiopaque markers of treatment region 98 are aligned with the radiopaque markers 102 of the positioning device and it is clear that the treatment catheter 90 is positioned over the defect properly for treatment. The positioning device 94 may then be removed and a closure treatment can then be applied to the defect to close the layered tissue defect. If the treatment device 90 is placed directly over the positioning device 94, the positioning device 94 is preferably constructed so that it can be removed with the treatment device 90 left in place. For example, in this embodiment, it is preferable that the flexible elongate members 106 can be pulled back through a lumen of the treatment device 90.

Figure 12A:
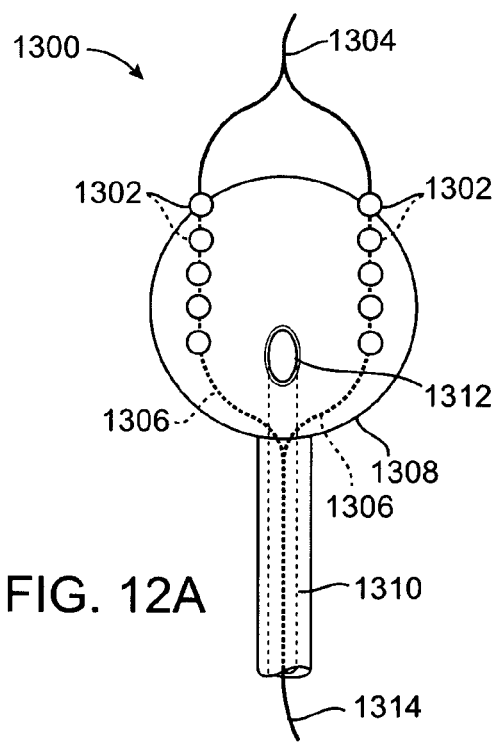
FIG. 12A shows a crossing catheter with a guidewire lumen.
Figure 38A:
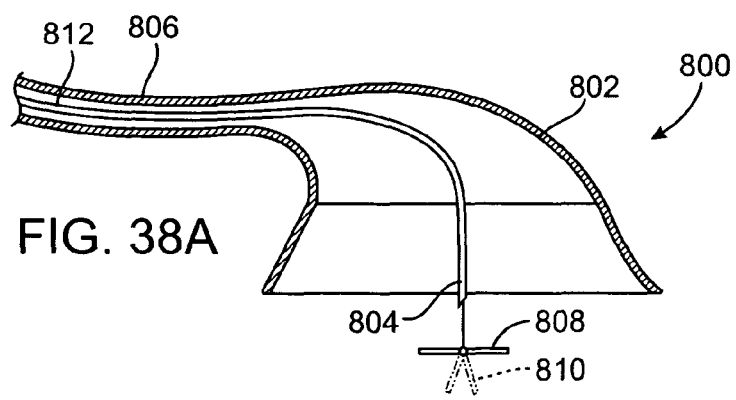
FIGS. 38A-38D show an apposition device and how it apposes tissue.
Figure 38B:
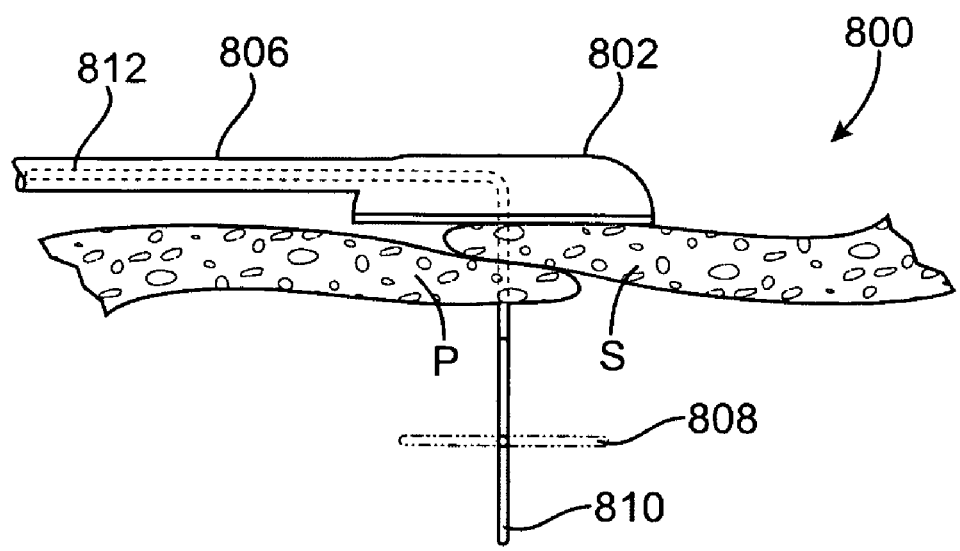

FIG. 12A shows a crossing catheter similar to the embodiment described in FIG. 12 above. In FIG. 12A, the crossing catheter 1300 is also used with a positioning device. Here, the crossing catheter 1300 has an elongate shaft 1310 and a housing 1308 on the distal end of the shaft. An inner lumen shown by dotted lines is axially disposed within the crossing catheter elongate shaft 1310 and has an exit port 1312 in the housing. The crossing catheter 1300 is used with a positioning device 1314 that is advanced to the layered tissue defect (such as a PFO) until the distal end 1304 extends over the defect. The positioning device 1314 has flexible elongate members 1306 that mark the boundaries of the tissue defect. In the case of a PFO, the flexible elongate members 1306 indicate the tunnel of the PFO and radiopaque markers 1302 permit a physician to observe the defect under fluoroscopy. Once the positioning device 1314 has been delivered, the crossing catheter 1300 is then advanced over the positioning device 1314 until the housing 1308 is disposed over the tissue defect as indicated by the radiopaque markers. A vacuum may then be applied to the crossing catheter, either via the inner lumen or another lumen so that the housing 1308 is apposed with the tissue defect. Once apposition is obtained, the positioning device 1314 may be removed and a treatment device, or a guidewire over which a treatment device may be delivered, may be advanced axially along the catheter elongate shaft 1310 through the inner lumen or another lumen until the distal end of the treatment device exits the inner lumen port 1312. For example, the inner lumen port may be curved laterally such that, in the case of placing a guidewire, the guidewire exits the inner lumen at an angle sufficient to direct the guidewire transeptally, or through the tissue of the layered defect (for example from right atrium to left atrium either through the primum, through the secundum or through both tissue structures as depicted in FIG. 38B hereinbelow). Once the guidewire is placed transeptally and centered optimally with respect to the defect, a closure catheter may be passed over the guidewire such that it may be deployed across the atrial septum at a point that is substantially centered, or positioned to close the PFO. For purposes of this disclosure, "centered" or "positioned" may be descriptors of how the crossing catheter is optimally positioned to guide a transeptal puncture device in order to position a separate treatment catheter at the position on or over the tissue defect such that when a closure device is deployed, it substantially closes the defect. Once the layered tissue defect is repaired, the closure treatment device and crossing catheter may then be removed from the treatment site.

Figure 13:
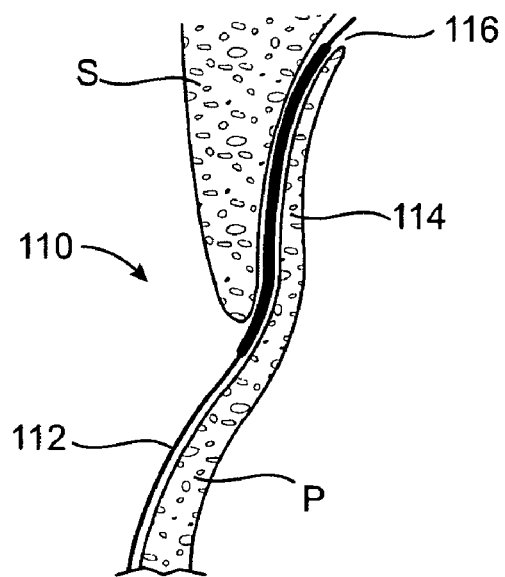
FIG. 13 is a cross-sectional view of a positioning device in the tunnel of a layered tissue defect.
Figure 14:
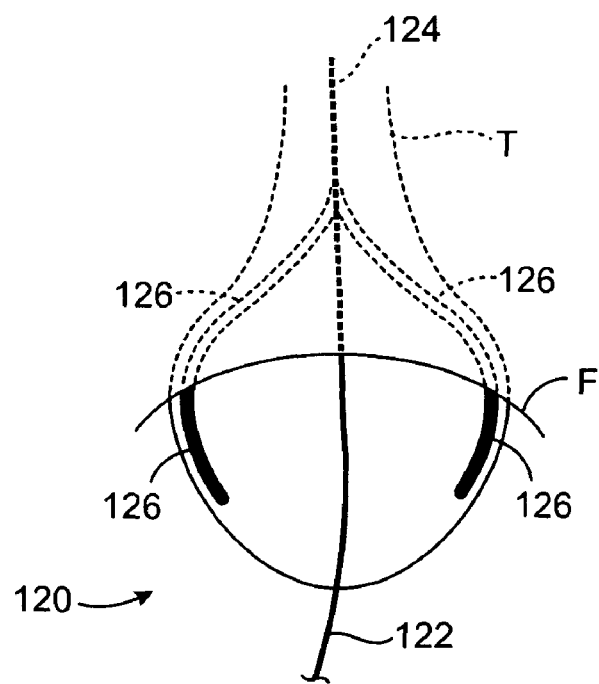
FIG. 14 illustrates how whiskers on a catheter position the device and indicate the width of the tunnel entrance.

FIG. 13 shows a cross-sectional view of a portion 114 of a positioning device 110 in a PFO tunnel. A portion of the positioning device 110 extends past the tunnel exit 116, while the proximal end of the device is outside of the tunnel, 112. FIG. 14 shows another embodiment of a positioning device. Positioning device 120 represents a guidewire with whiskers 126 at the distal end to seat the wire device through a PFO and also to assist in sizing the width and locating the tunnel entrance or mouth F. The whiskers 126 may be fabricated from a pre-formed resilient material (e.g. nitinol, spring temper steel, Elgiloy®, formed or coiled stainless steel wire) such that when the guidewire is deployed from a catheter, the whiskers 126 deploy outwardly to seat within the corners of the PFO tunnel T. Once in place, the closure device can be tracked over the guidewire 122. The closure device may include radiopaque markers that can be aligned with guidewire markers (not shown) to seat over the outer limits of the width of the PFO and to include the tunnel entrance. Once in place the guidewire can be removed through the guidewire lumen in the closure device. In the case of the whisker wire, the whiskers would flex upwards to be in line with the main wire and all be pulled out through the guidewire lumen.

Additionally, the whisker elements may be spring loaded to ensure that they extend out to the farthest width of the defect that they are measuring or positioning. It is also within the scope of the invention that the guidewire device may be a separate catheter and while it provides a visual docking target, the closure catheter and the guidewire/positioning catheter are not physically linked, but are placed separately from each other.

FIGS. 15A-15D shows one embodiment of the whiskers positioning device discussed above with respect to FIG. 14. In FIG. 15A, a positioning device 130 has a sheath housing 136 with slits 138. A positioning catheter 132 lies in the sheath 136 and positioning whiskers 134 also remain covered by the sheath 136. Once the positioning device 130 is placed within a PFO, the whiskers 134 may be released from the sheath 136, and the whiskers then expand through the slits 138 in the sheath 136, as shown in FIG. 15B. The whiskers 134 spring to a fully deployed position thereby properly positioning the device 130 and allowing PFO sizing, shown in FIG. 15C. Once the positioning device 130 is no longer required, the whiskers 134 may be retracted into the sheath 136 which is illustrated in FIG. 15D.

In another embodiment shown in FIGS. 16A-16C, a looped wire design is employed. In this embodiment, a looped guidewire type of positioner is used to position the device. In FIG. 16A, a closure device 140 has an elongated catheter shaft 142 and a distal housing 150. A treatment region 144 is disposed on the housing 150 along with placement wire apertures 146 and a guidewire aperture 148. The looped guidewire in FIG. 16B with high flexibility is retractable into apertures 146 and can be extended into the defect in a looped configuration to form a sizing and positioning device, as well as serving as a rail over which closure device can be placed accurately at a treatment site. In FIG. 16C, the looped wire 154 is advanced until it engages the walls of the layered tissue defect. A guidewire 148 may also be used to help deliver the closure device 140 to the tissue defect, and it exits out of aperture 148. FIG. 16D shows how the guidewire 152 and looped wire 154 fit into a PFO tunnel T and position the closure device housing 150 over the entrance of the defect, F. The looped wire 154 may be designed with variable stiffness along its length to facilitate sizing and positioning. For example, the looped wire 154, shown in a straightened out configuration in FIG. 16E may have a stiff section 156 for accommodating the widest PFOs, a less stiff section 158 adjacent to the stiffest section 156 and a flexible section 159 in the middle of the loop wire.

Figure 17A:
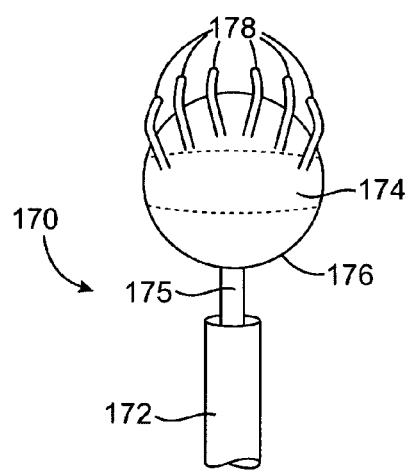
FIGS. 17A-17B show other features on the closure device housing that facilitate with positioning.
Figure 17B:
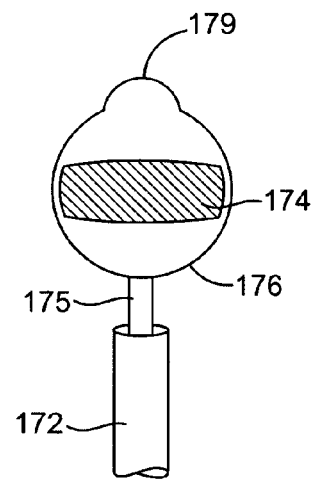
Figure 18A:
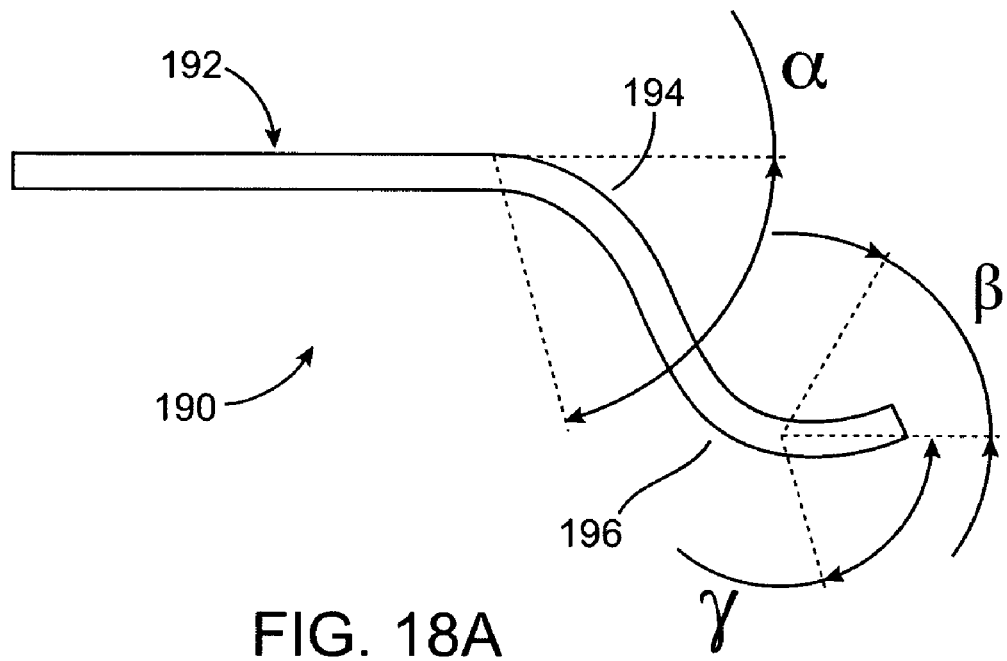
FIGS. 18A-18B illustrate a compound bend in the closure device that assists with device positioning.
Figure 18B:
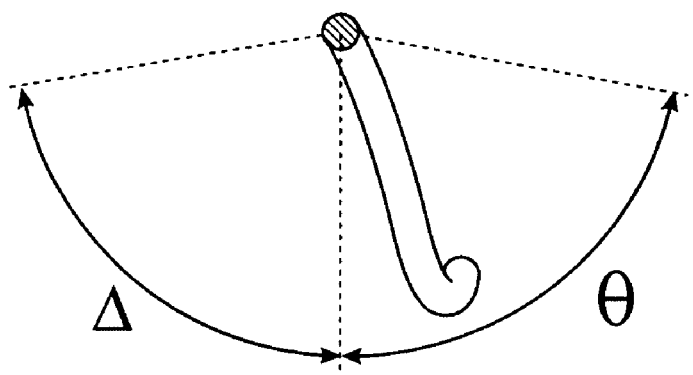

Additional catheter features may also be employed in order to aid in placement and sizing. For example, in FIG. 17A, a closure device 170 has a retractable catheter shaft 175 with a housing 176 attached to the catheter shaft 175. The housing 176 has a treatment region 174 on the housing and extensible positioning rails 178 serve as feelers to help stabilize the treatment device 170. The housing 176 and positioning rails 178 are retractable into sheath 172. Alternatively, the housing shape may be modified to include an extended nose 179 as seen in FIG. 17B. This shape helps position the closure device 170 against the tissue defect. A moveable guidewire lumen (not shown) may also be used to facilitate placement and sizing. A compound bend can also help the closure device to be properly positioned adjacent to a tissue defect as shown in FIG. 18A. In FIG. 18A, several bends 194, 196 in the shaft 192 of a closure device 190 help to properly position the treatment portion of the device 190 against the tissue defect. In FIG. 18A, typical ranges for the first bend indicated by angle α is up to 75° while a second bend indicated by angles β and γ are up to 60° and 75° respectively. FIG. 18B shows a back view of the of the treatment device shaft where angles θ and Δ both typically can range up to positions that encompass a range up to 80°.

Figure 19A:
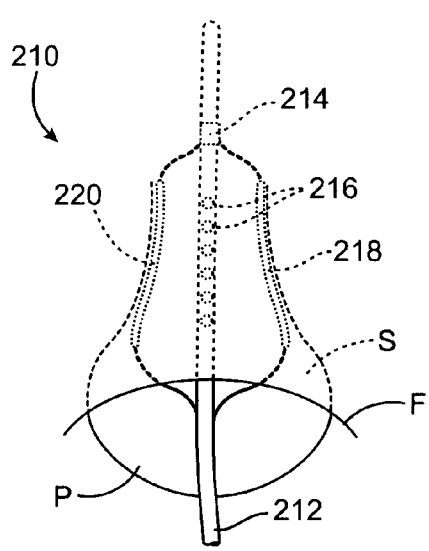
FIGS. 19A-19B show various embodiments of a bipolar positioning and sizing closure device.
Figure 19B:
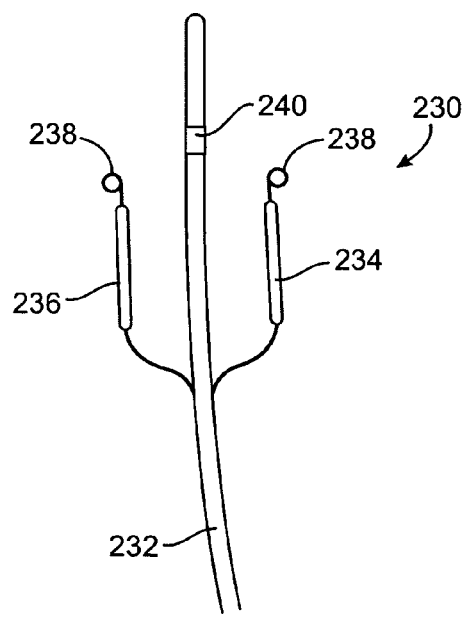

In an alternative embodiment, a wire sizing, positioning and treatment device may also include an electrode or multiple electrodes for applying energy to the defect while it is in position or near the position to close the defect. The electrode may be formed or treated to be radiopaque to assist in sizing of the defect. Wire forms the bipolar electrode configurations, and sizes, orients and applies energy to close the defect. In FIG. 19A, a wire sizing, positioning and treatment device 210 is placed in a PFO. Wires 218 and 220 position the device 210 within the tunnel, and also serve as electrodes. A radiopaque marker band 214 may be employed to indicate device position and vacuum lumens 216 may also be employed to allow the treatment device to approximate the defect surfaces prior to, during or following the application of sealing energy. In an alternative embodiment, FIG. 19B shows a design where the electrodes 234, 236 are modified on positioning, sizing and treatment device 230 with tips 238 that help the device to be removed after application of energy without disturbing the weld created.

IV. Catheter Device

Figure 20:
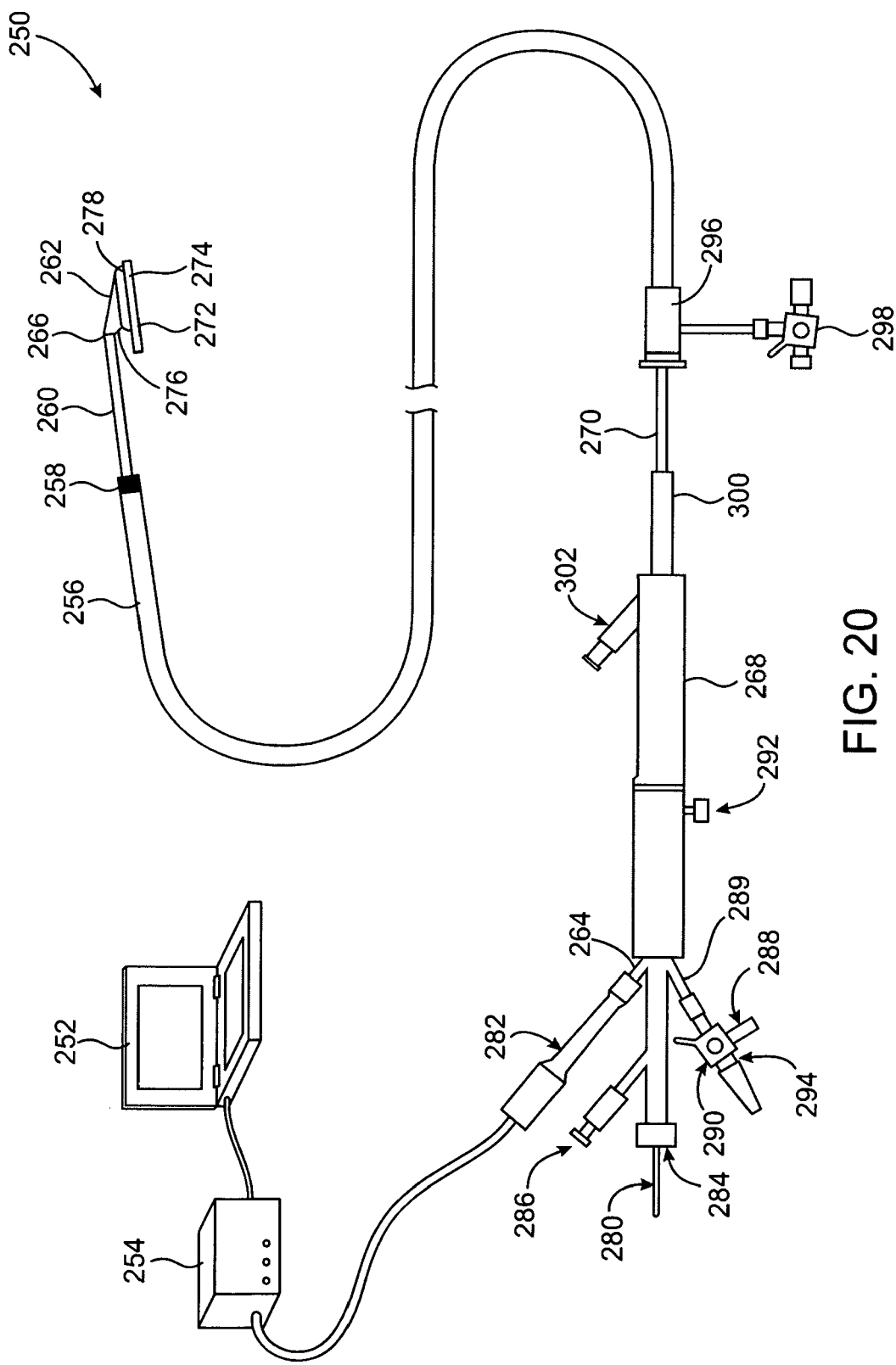
FIG. 20 illustrates a closure treatment system.

Referring now to FIG. 20, in an exemplary catheter device 250 which may be modified according to the present invention for treating an anatomic tissue defect includes an elongate catheter shaft 260 having a proximal end 264 and a distal end 266, a sheath 256 (or "sleeve") optionally disposed over at least part of shaft 260, a handle 268 coupled with a proximal end of sheath 256, and a housing 262 coupled with catheter shaft distal end 266. A distal opening 272 for opposing tissue, an electrode 274 (or other suitable energy transmission member in alternative embodiments for transmitting radiofrequency (RF) energy to tissues, attachment members 276 (or "struts") for coupling electrode 274 with housing 262 and for providing support to housing 262, and radiopaque markers (not shown) for coupling attachment members 276 with housing 262 and/or catheter body distal end 266 and for facilitating visualization of device 250. A guidewire 280 is passed through catheter 250 from the proximal end through the distal end. In the embodiment shown, catheter body proximal end 264 includes an electrical coupling arm 282, a guidewire port 284 in communication with a guidewire lumen (not shown), a fluid infusion arm 286 in fluid communication with the guidewire lumen, a suction arm 289 including a suction port 294, a fluid drip port 288, and a valve switch 290 for turning suction on and off.

Fluid drip port 288 allows fluid to be passed into a suction lumen to clear the lumen, while the suction is turned off. A flush port with stopcock valve 298 is coupled with sheath 256. Flush port and stopcock valve 298 allows fluid to be introduced between sheath 256 and catheter body 260, to flush that area. Additionally, sheath 256 has a hemostasis valve 296 for preventing backflow of blood or other fluids. The distal tip of the sheath also has a soft tip 258 for facilitating entry and release of the catheter housing 262 during delivery. The catheter device 250 also includes a collapsing introducer 300 partially disposed in handle 268.

The collapsing introducer facilitates expansion and compression of the catheter housing 262 into the introducer sheath 256. By temporarily introducing the collapsing introducer sheath 300 into introducer sheath 256 the catheter housing 262 may be inserted into introducer sheath 256 and then removed, thereby allowing the introducer sheath 256 to accommodate a larger housing 262 without having to simultaneously accommodate the collapsing introducer 300 as well. The collapsing introducer 300 also has a side port for fluid flushing 302 and a valve (not shown) prevents fluid backflow. Locking screw 292 disposed in the handle 268 may be tightened to control the amount of catheter shaft 260 movement. Finally, an energy supply 254 is connected to the catheter via the electrical coupling arm 282 and a controller 252 such as a computer is used to control energy delivery. In operation, it may also be possible to de-couple the handle from the device if desired, or to remove the handle altogether.

Figure 21:
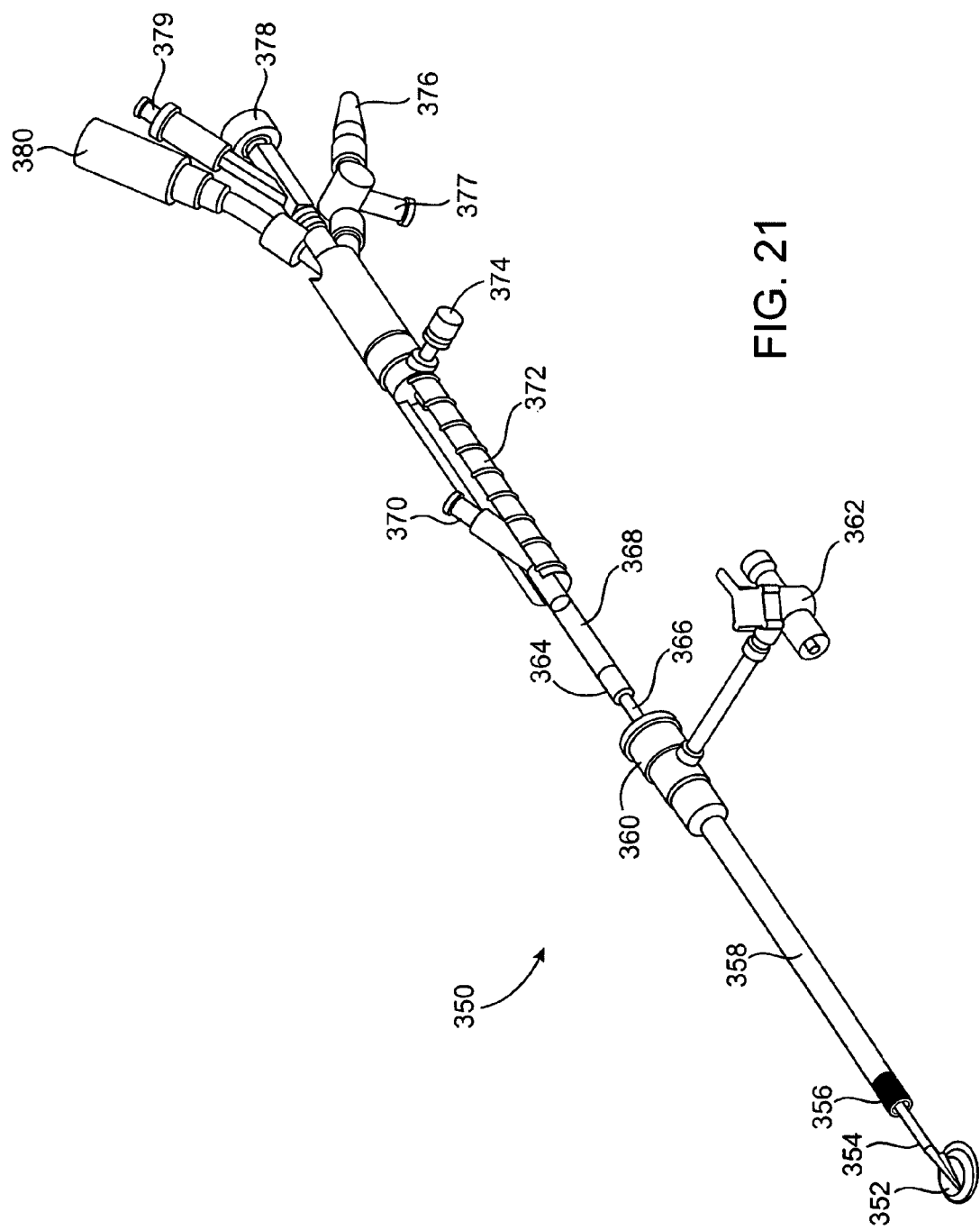
FIG. 21 shows a closure treatment apparatus.

FIG. 21 illustrates the treatment catheter device 350 only. The treatment catheter 350 has an elongate catheter shaft 366 having a distal end 354. A housing 352 on the distal end of the catheter shaft 354 delivers a treatment to a layered tissue defect to close the defect. The catheter shaft 366 is axially aligned with a handle 372 and exits at a proximal end of the device and is sealed with a hemostasis valve 378 to prevent fluid backflow. An energy connector 380 and flush port 379 are also disposed on the proximal catheter end along with a vacuum port 376 with additional port 377. A screw 374 tightens the catheter shaft 366 within the handle 372 to minimize motion between the two. A collapsing introducer tube 368 with soft tip 364 and flush port 370 is also disposed partially in the handle 372 and is used to collapse the housing 352 and introduce it into an introducer sheath 358. The introducer sheath 358 also has a soft tip 356 which helps to accommodate and collapse the housing 352 when it is being withdrawn back into the introducer sheath 358 for removal from the body. A radiopaque marker may also be placed near the soft tip 356 to assist in visualization during a treatment procedure using fluoroscopy. Both the collapsing introducer 368 and the introducer sheath 358 have side ports 370, 362 for flushing. Valves in the collapsing introducer (not shown) as well as a hemostasis valve in the introducer sheath 360 prevent blood or other fluids from backflowing.

Figure 22B:
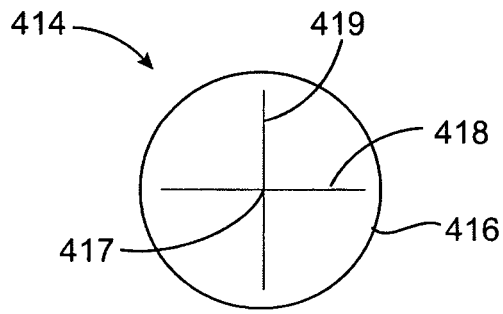
FIGS. 22A-22B illustrates an introducer sheath and hemostasis valve used with a closure treatment apparatus.
Figure 22A:
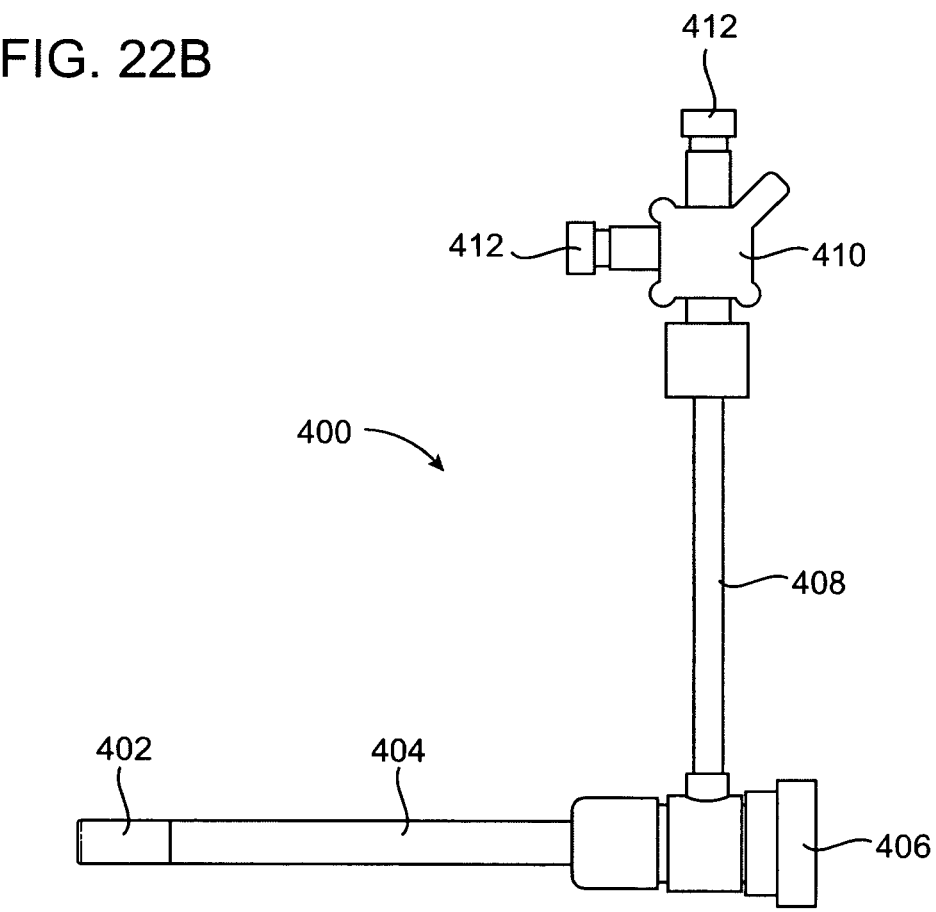

FIG. 22A shows the introducer sheath preferably used in the closure treatment system of FIG. 20. In FIG. 22A, introducer sheath 400 has an elongated shaft 404 which is used to introduce the closure treatment device into the human body. The introducer sheath 400 in FIG. 22A is shown as an elongated sheath, however the sheath may be angled or bent in different directions to assist with placement of the closure treatment device. The introducer sheath 400 has a soft distal tip 402 and may include a radiopaque marker, which helps to accommodate the larger size distal end of a treatment catheter and collapse it into the sheath during removal as well as facilitate visualization under fluoroscopy. A side port 408 with one or more flush ports 412 and a stopcock valve 410 is also useful for flushing the introducer sheath and a hemostasis valve 406 prevents blood or fluid backflow when the treatment catheter is placed in the sheath. FIG. 22B illustrates one embodiment of the hemostasis valve, where two silicone disks 416 are used to create the hemostasis valve membrane 414. In FIG. 22B the silicone disk 416 is then scored partially through the top surface and also partially through the bottom surface, but not all the way through the disk. Two score lines are created 418, 419 transverse to one another. At the intersection of the score lines 417, the silicone disk is punctured all the way through. This permits a catheter distal tip to penetrate the silicone disk and when it is advanced further, the score lines separate enough to accommodate the catheter while maintaining a seal. In preferred embodiments, the silicone disk is approximately 0.352" in diameter and the slit widths can accommodate and seal over a 16 F shaft.

Figure 23:
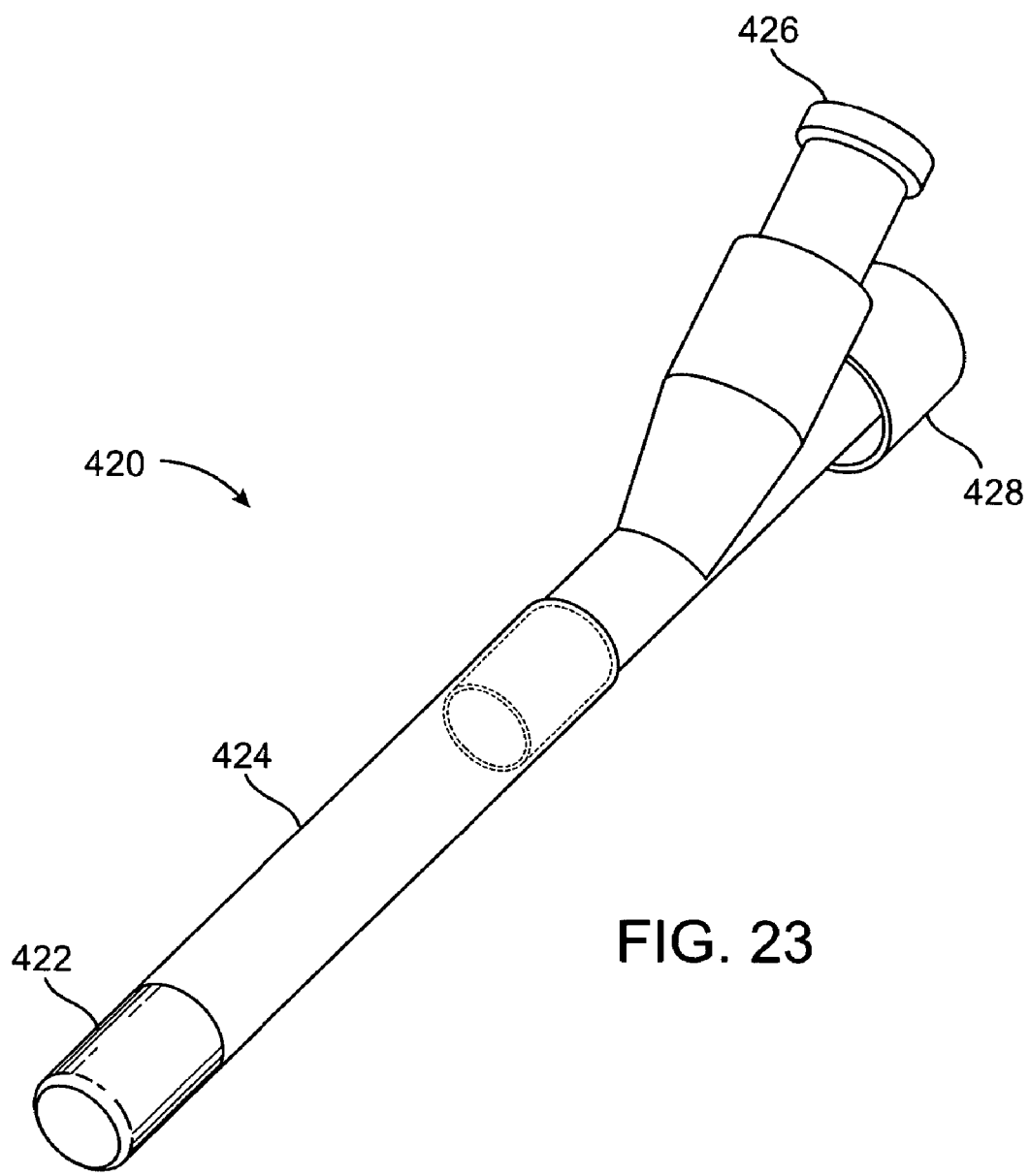
FIG. 23 illustrates a collapsing introducer.

The collapsing introduce 420 is illustrated next in FIG. 23. Collapsing introducer 420 has an elongate section 424 which can accommodate a distal treatment catheter housing. By collapsing the housing in the collapsing introducer, it can then be easily introduced into the introducer sheath previously described. The distal tip of the collapsing introducer is soft to help accommodate the larger size treatment catheter housing. In a preferred embodiment, the collapsing introducer has a length approximately 6 inches and its soft tip is fabricated with Pebax polymer having a durometer of, for example, 35D while the elongate section 424 comprises, for example Pebax 72D durometer. Other relative durometers may also be used in the scope of the present invention to facilitated collapse of the catheter housing, while still providing flexibility and torqueability of the catheter shaft. While currently illustrated as round, the soft tip may also be oval, crescent moon, or asymmetrically crescent shaped to facilitate collapsing the housing. The proximal end of the collapsing introducer has a hemostasis valve 428 designed to accommodate the treatment catheter shaft as well as a flush port 426.

FIGS. 24A-24E illustrate how the collapsing introducer works. In FIG. 24A, a treatment catheter 450 is inserted into the collapsing introducer 452. In FIG. 24B, the collapsing introducer 452 is slidably moved towards the distal end of the treatment catheter 450 until the housing 460 is collapsed and enclosed by the collapsing introducer 452. The treatment catheter 450 with its housing 460 collapsed in the collapsing introducer 452 is then advanced and introduced into an introducer sheath 462 in FIG. 24C, and the collapsing introducer 452 is pulled back, so that the housing 460 is released from the collapsing introducer 452 but still is constrained by the introducer sheath 462. In FIG. 24D the treatment catheter 450 is advanced forward into the introducer sheath 462 until the housing 460 exits the introducer sheath 462 and resumes its shape. The treatment catheter is advanced to a layered tissue defect and a treatment is then applied. After the treatment is competed, the catheter housing 460 is pulled back into the introducer sheath 462 and the catheter 450 may be removed from the patient's body.

In alternative embodiments as described in detail below, additional features or fewer features may be included on catheter device 250. For example, a number of modifications may be made to catheter body distal end 266 in accordance with different aspects of the invention. Some of these may include lubricious liners or coatings on the device as well as heparin coatings for reducing thrombus. Different configurations for fluid delivery and vacuum are also possible. Additionally, a controller built into the power generator can alleviate the need for a computer controller, except for displaying treatment parameters. Therefore, the following description of embodiments is intended to be primarily exemplary in nature and should not be interpreted to limit the scope of the invention as it is described in the claims.

V. Optimizing Tissue Apposition

A. Housing Design and Other Tools. One aspect of a successful tissue weld of a defect to be treated, is the interface of the tissue at the therapeutic element (electrode, heating element, or mechanical closing mechanism). This interface may be impacted by the following variables, including any leaks in the housing, leaks or shunts in the anatomy (e.g. through the PFO), physical placement of the housing over the defect, deformation of housing against tissue interface and resulting housing volume, forces exerted by the housing, and the pressure used to appose the treatment site with the housing. Various embodiments are presented that may assist in tissue apposition within or against the treatment element for closing a PFO or other layered tissue defect. These designs may be used in conjunction with any of the defect closure devices described in the co-pending cases which have been previously incorporated by reference. Particularly, closure catheter devices such as those detailed in the co-pending application Ser. Nos. 10/873,348; 10/952,492; and 11/049,791 may be enhanced by the following features.

Figure 25A:
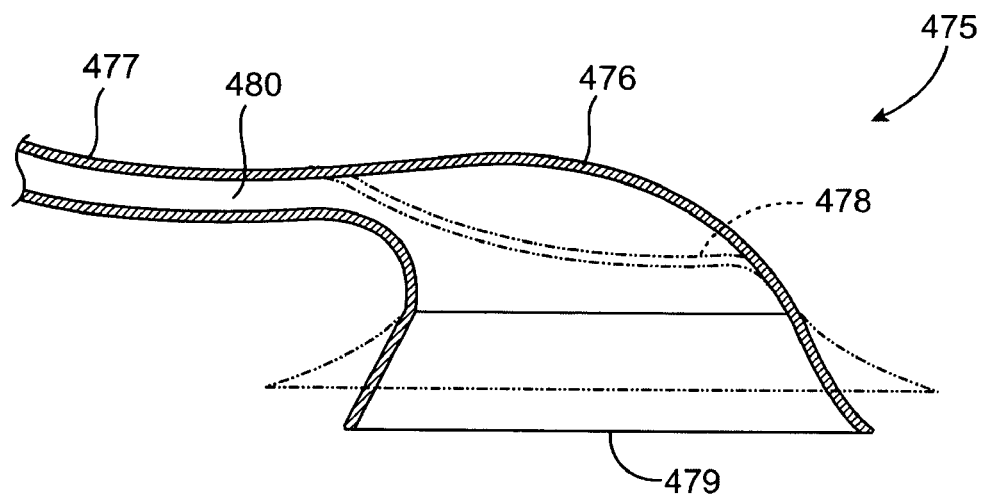
FIGS. 25A-25B show various aspects of the treatment catheter housing.

Housing designs that maintain a sufficient chamber and features to grip and appose the tissue of the defect, and maintain the seal of the therapeutic element at the tissue interface may be desirable. A representative embodiment of a catheter housing 475 is shown in FIG. 25A. The housing 475, is attached to a catheter shaft 477 and is formed from 60A durometer silicone because of its high tear strength and resistance to deformation at the temperatures employed to weld tissue. Other durometers may also be employed and in some cases a housing may be constructed of multiple durometer polymers in one device, or a polymer and a reinforcing element such as mesh or a filament. The housing 475 has a primary shape 476 and a surface 479 adapted to appose the tissue defect. However, upon application of vacuum through a lumen 480 in the catheter shaft 477, the housing may still flatten or collapse 478. Similarly, skirt or flange of the housing can flatten as well. This can lead to a shallower (shallower) housing volume within which tissue may be apposed. As such, certain features may be designed into the housing to define the optimum housing volume.

Figure 25B:
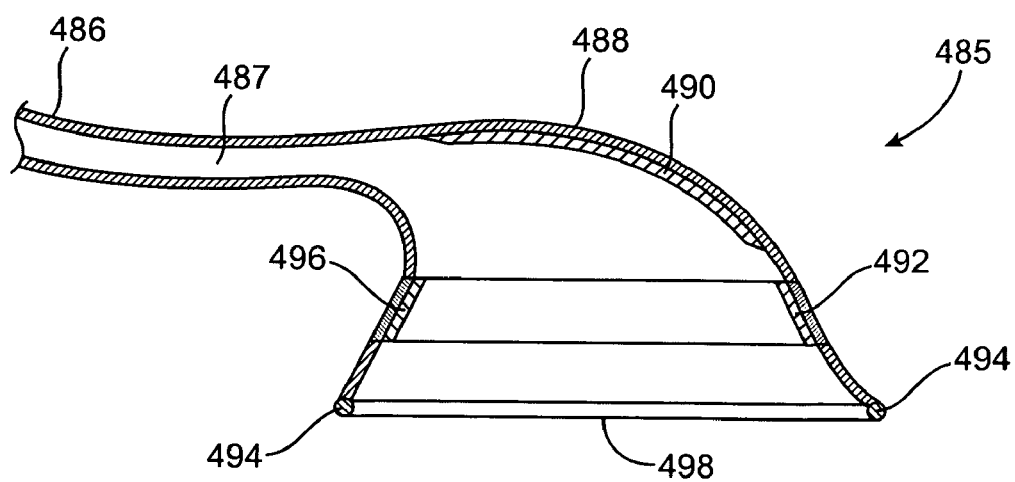

Some features that provide a more resilient housing, and in turn allow greater tissue invagination upon vacuum activation, include: reinforcing the roof of housing, taller housing, and reinforcements in flange or skirt of housing. As depicted below, areas of the housing may be selectively reinforced to aid in sealing the treatment area within the device housing. In particular the "roof" of the housing may be formed of a thicker material (preferred material is silicone and it would be molded, the mold cavity would be constructed to allow more material to flow into the reinforced region). The reinforced roof allows the housing to remain somewhat tented during vacuum apposition. For the roof reinforcement, a stiffening element, such as spring steel or nitinol may be used in thicknesses ranging from, for example between 0.002"-0.005." Reinforcement in the roof region may also be achieved by molding a thicker region using the material of the housing, or adding material to the roof of the housing to make the reinforced area in the range of 0.005" to 0.025" thick, for example 0.010" thick while still accommodating vacuum channels as described in copending application Ser. No. 10/952,492, the full disclosure of which has previously been incorporated by reference, and allowing the housing to collapse. Some of these features are incorporated into the embodiment of FIG. 25B. In FIG. 25B, the housing 485 comprises a reinforced region 490 in the roof 488 of the housing 485.

At the midpoint of the housing between the main housing and the flange, stiffening elements 492 or extensions 496 may be employed in a similar manner (e.g. additional molded material or separate resilient extensions). For example, such extensions or reinforcement may have a thickness of between 0.005" to 0.050" and between 1-3 mm in height.

In addition, a semi-rigid ring 494 may be incorporated into the bottom of the flange to give hoop strength to the flange, especially when vacuum is applied via a lumen 487 in the catheter shaft 486 connected with the housing 485. In certain embodiments, a 1 mm×1 mm square in cross-section of material was molded at the bottom of the flange. In another embodiment, a nitinol ring was used, allowing the thickness of the region to be about 0.010" or slightly smaller and not square in cross-section which allows for better collapsibility. In certain other embodiments, a polymer O-ring may be employed. Such additional housing material and reinforcement elements may be used alone or in combination with each other for the desired rigidity, while still allowing the housing to be collapsed within a guide catheter for deployment to and retrieval from the treatment site. The housing element 485 may be adapted to appose the tissue and keep it in place while a fusing or fixation element is brought into contact to secure the tissue. For example, the housing element 485 may be activated (suction applied) and then a catheter device containing a clip or fixation element may be advanced to the treatment site, and applied to the apposed tissue. Examples of fixation elements may be clips such as those described in pending application Ser. No. 10/787,532, filed Feb. 25, 2004; and Ser. No. 10/811,228, and further U.S. application Ser. No. 10/948,445 (Publication 2005/0070923) to McIntosh, U.S. application Ser. No. 10/856,493 (US Publication 2004/0249398) to Ginn, and PCT publication WO/04/069055 to Frazier, the full disclosures of which are incorporated herein by reference.

Other housing configurations adapted to appose a layered tissue defect such as a PFO are illustrated in FIGS. 25C through 25I, which shows a bottom view of the housing that apposes the tissue defect. For example, in FIG. 25C, a housing 1320 has a boomerang shaped side 1322 with a nose extending from the triangular apex region that may provide better apposition with certain tissue defects. FIG. 25D shows a triangular shaped side 1342 of the housing 1340 with apices radiused while FIG. 25E illustrates a kidney bean shaped side 1362 of the housing 1360. FIG. 25F shows a circular housing side 1382 while FIG. 25G depicts a housing 1400 with a generally triangular shaped side 1402 but with the base and apex modified to include nose-like protrusions. FIGS. 25H and 25I also show variations on the triangular shaped side of the housing for tissue apposition. In the case where an electrode is used to close the layered tissue defect, the electrode shape may match the housing or it may be modified to best match the tissue defect. FIGS. 25C through 25I show various electrode embodiments that may be used.

Figure 26:
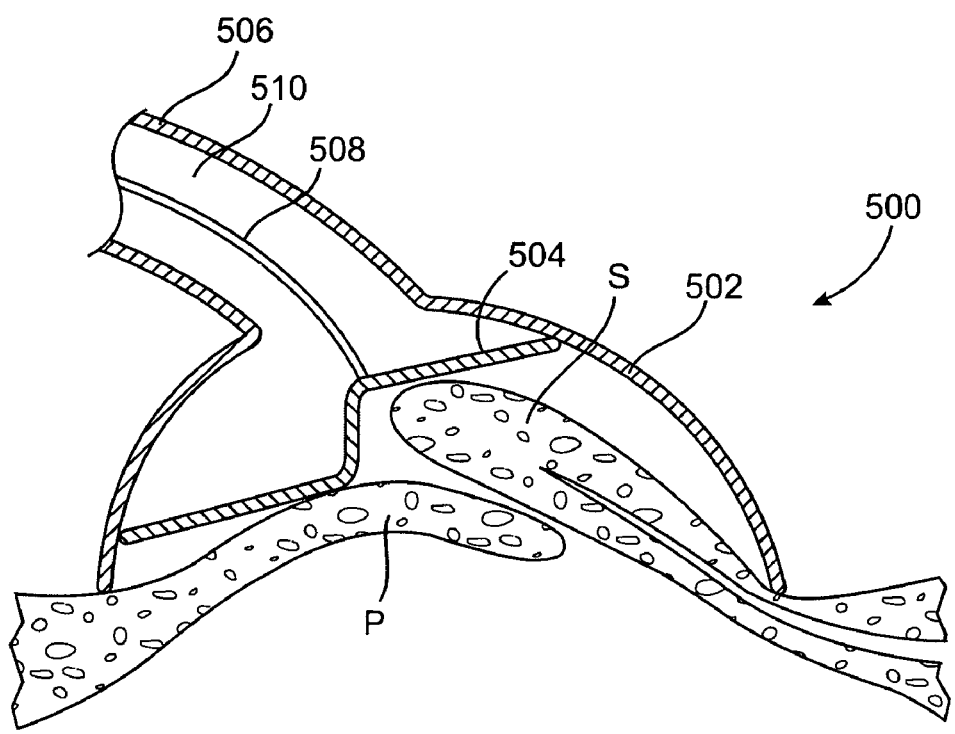
Figure 27:
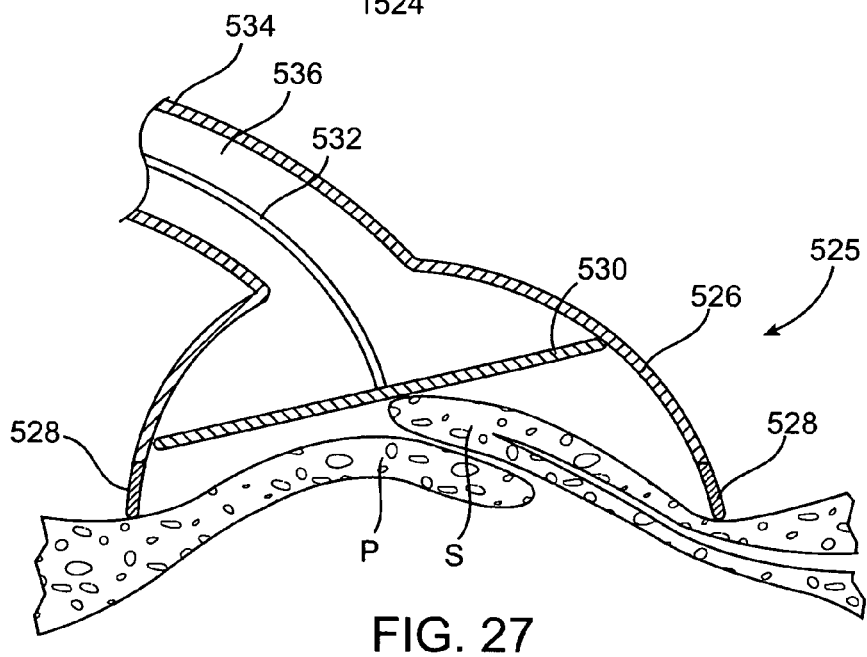

A cone shaped or domed housing can provide greater tissue apposition, (optionally in combination with a "stepped" electrode as set forth in application Ser. No. 10/952,492, the full disclosure of which has previously been incorporated herein by reference). An example of the stepped electrode 504 may be seen in housing 500 of FIG. 26. The electrode may alternatively be planar and optionally may be angled in the housing to accommodate tissue thickness variations. This is illustrated as electrode 530 in housing 525 of FIG. 27.

Figure 26A:
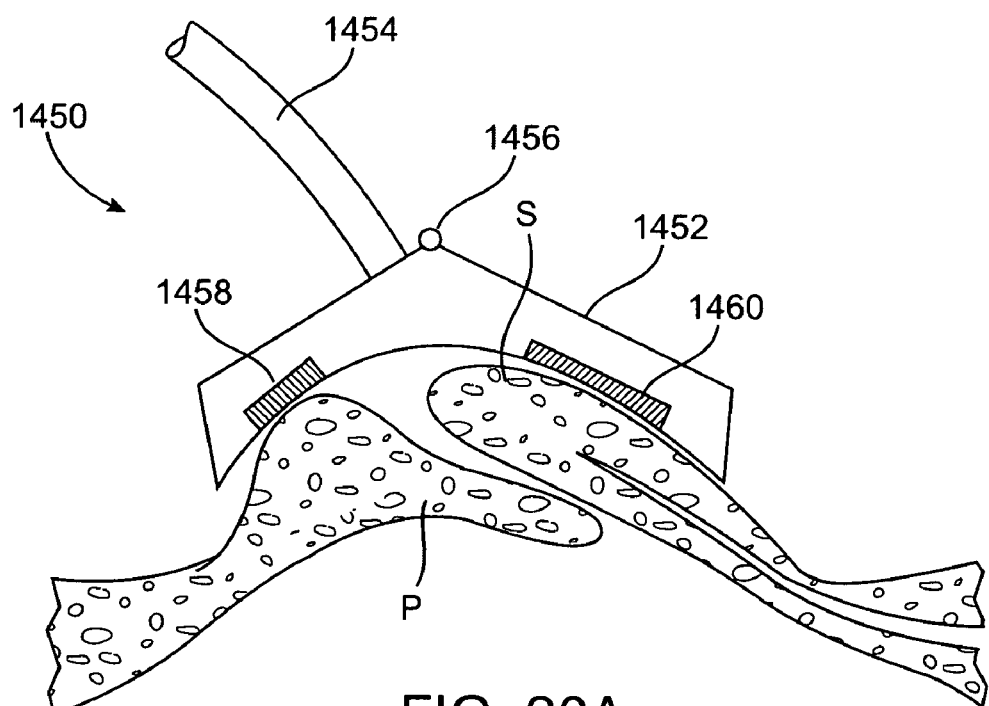

A hinged housing may also provide better tissue apposition and defect closure by allowing the housing to better adapt to anatomical variations in the tissue defect. In one embodiment shown in FIG. 26A, a treatment device 1450 comprises an elongated catheter shaft 1454 with a housing 1452 adjacent to its distal end. The housing has a hinge mechanism 1456 that allows the housing to articulate. When the housing articulates, its shape adjusts to better conform with the anatomy of the tissue defect. In FIG. 26A, an apposition surface 1462 is operatively coupled with the housing so that it too can better conform to the tissue defect anatomy. The apposition surface 1462 may only comprise a surface for apposition or may additionally comprise a treatment region that can be used to close the layered tissue defect. Furthermore, optional separate vacuum ports 1458 and 1460 may be located in the housing to assist the housing appose the tissue defect. In FIG. 26A, vacuum ports 1458 and 1460 are positioned within the housing so that they may help draw in the primum and secundum tissue layers for better apposition in a PFO defect.

Figure 26B:
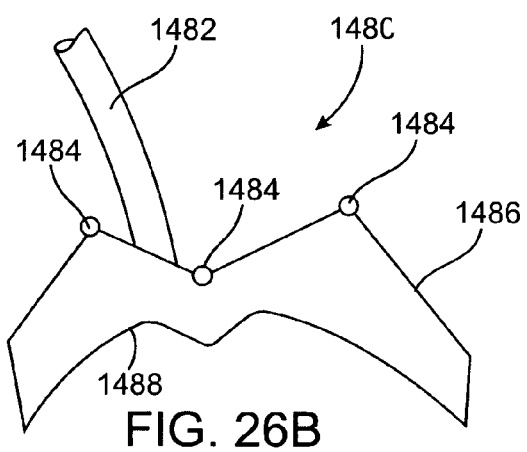
Figure 26C:
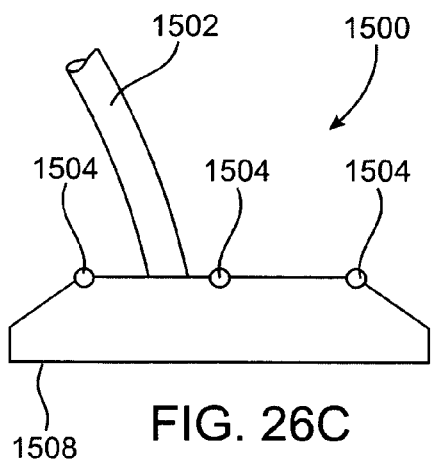
Figure 26D:
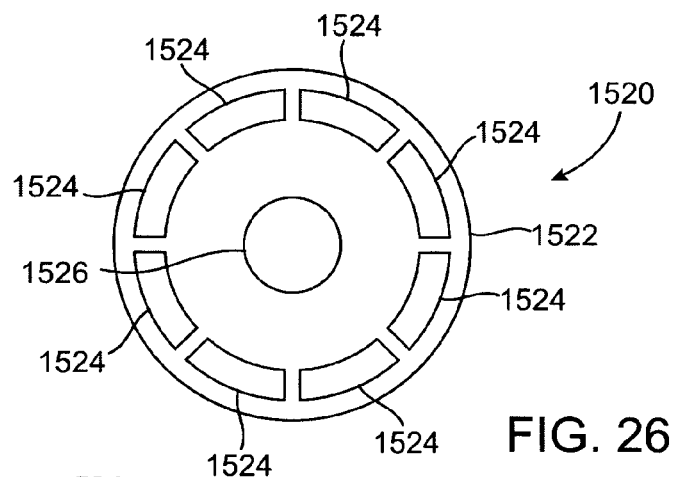

In another embodiment shown in FIG. 26B, multiple hinges 1484 are utilized in the housing 1486 of a treatment device 1480. An elongate shaft 1482 is connected to the housing 1486 and may be used to articulate the housing into different configurations with control rods or wires. The hinges may also be adapted to permit flexing of the housing when it is pressed against a surface. An apposition surface 1488 which generally takes the same form as apposition surface 1462 in FIG. 26A is also operatively connected to the housing 1486 so that its shape may be adjusted for better apposition with the tissue defect. FIG. 26C illustrates how the hinged housing 1506 of a treatment device 1500 provides an alternative apposition surface 1508. Furthermore, vacuum ports 1524, 1526 may be used in the housing 1522 of a closure device 1520, as illustrated in FIG. 26D. Here, vacuum ports 1524 around the circumference of the housing 1522 are combined with a centrally placed vacuum port 1526 for enhanced apposition of the housing 1522 against the tissue defect.

In alternative embodiments, a screen or slotted member may receive target tissue and oppose or "grip" the tissue during treatment. The screen may also be an electrode (monopolar/bipolar). FIG. 28A illustrates the primum P and secundum S tissue layers of a PFO being received into a screen upon application of vacuum through a lumen 556 in a catheter shaft 554 connected with the housing 552. In this embodiment, the screen is also an electrode with an electrical connector 560 running through a lumen 556 in the catheter shaft 554. A cross-sectional view of the tissue 568 being received into a screen 564 having a receiving aperture 566 is shown in FIG. 28B. FIG. 29A illustrates another way in which tissue P, S can be captured by the screen 584 and FIG. 29B shows a cross-sectional view of the tissue P, S being received by an aperture 588 in the screen 590. The screen 590 may also serve as an electrode to weld the tissue layers together or a secondary electrode may be deployed later during the procedure for welding.

Figure 30:
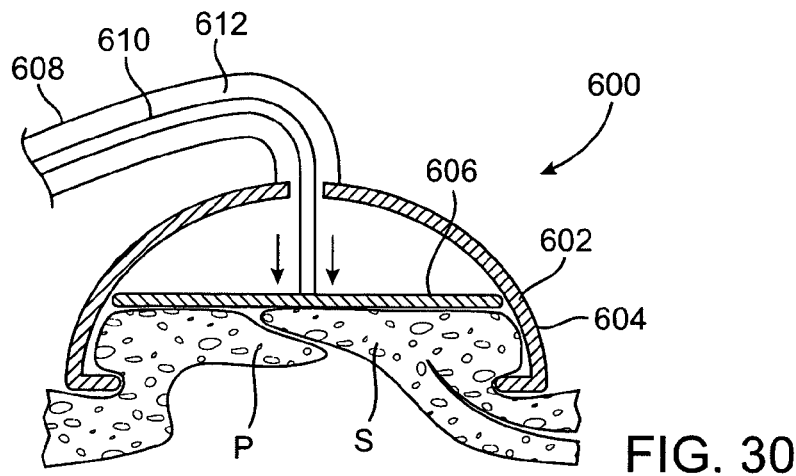

A recess in housing (or around skirt) 604 may assist in opposing or gripping tissue once the tissue is brought into the housing 600 using a vacuum. The screen 606 may be fixed to position tissue, or may be moveable as shown by the arrows in FIG. 30. Movement is controlled by an elongate member 610 through a lumen 612 in the catheter shaft 608 to further clamp tissue P, S against the recess 604, and the screen 606 may be an electrode. This embodiment is illustrated in FIG. 30.

Figure 31:
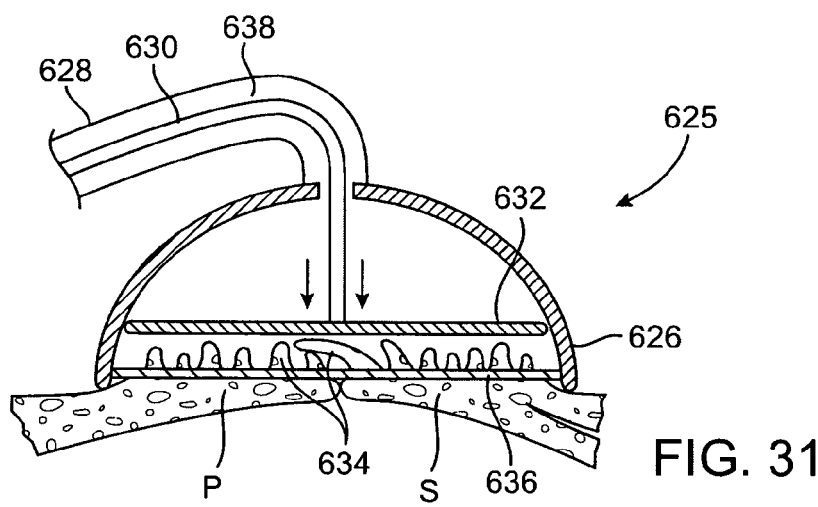

In another embodiment shown in FIG. 31, a first screen 633, usually with large interstices, may be employed together with a second screen 632. The second screen 632 is moveable between a first position and a second position as shown by arrows, or range of positions, relative to the first screen 633 and can be employed to trap the tissue P, S prior to treatment. Ideally, such screens 632, 633 could also be the electrode(s) for applying energy to join the tissue flaps of the heart defect together. They may be monopolar (one screen is energized while the other is totally insulated), or bipolar (wherein both screens are energized to create a bipolar energy field to assist in tissue fusing.

Figure 32:
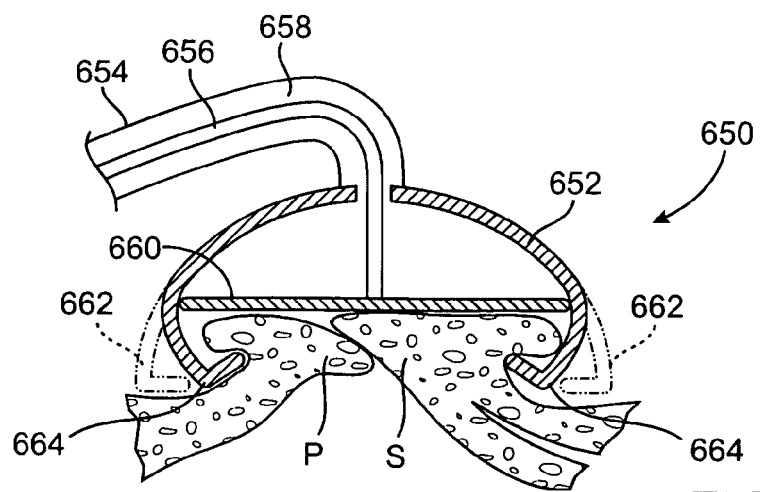

As shown in FIG. 32, the housing 652 may be actuated to further grip tissue with the recess feature 664 previously described above. Gripping action of the housing pivots the housing from one position 662 to a second position 664 and can be employed by actuatable struts (not shown) within housing material that extend from a pivot point at the apex of the housing, or by advancing a sheath (not shown) over the housing 652 to further collapse the structure on the tissue P, S.

Figure 32A:
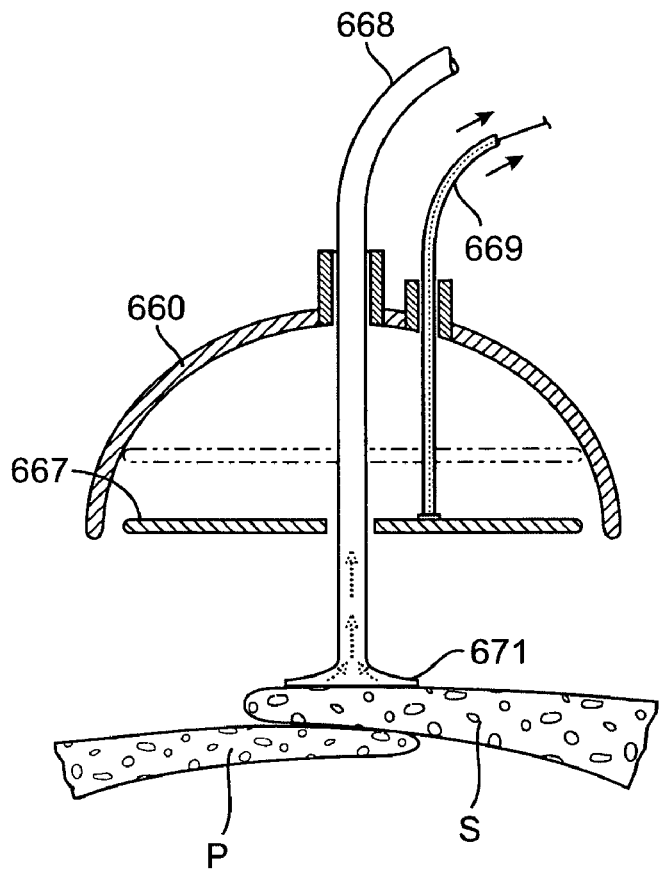
Figure 32B:
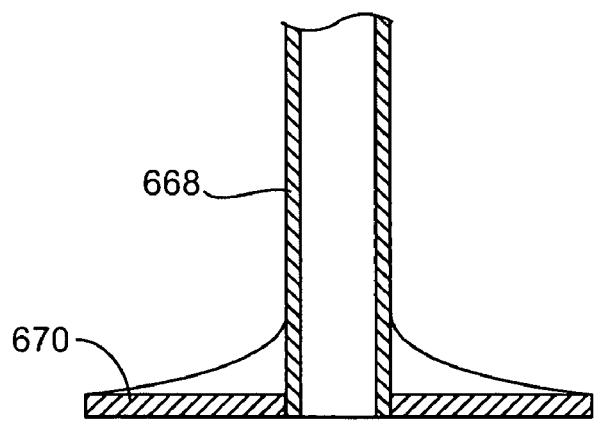

FIG. 32A illustrates an alternative approach to apposing tissue. In FIG. 32A, a moveable vacuum tube 671 is advanced in order to appose tissue P, S. Once vacuum is applied and the tissue is engaged, the vacuum tube 671 may be pulled back into the housing 666 so that tissue is engaged against a screen 667 which can also serve as an electrode. FIG. 32B shows that the vacuum tube 668 may have an optional vacuum screen 670 at its distal end to facilitate tissue engagement.

Figure 33:
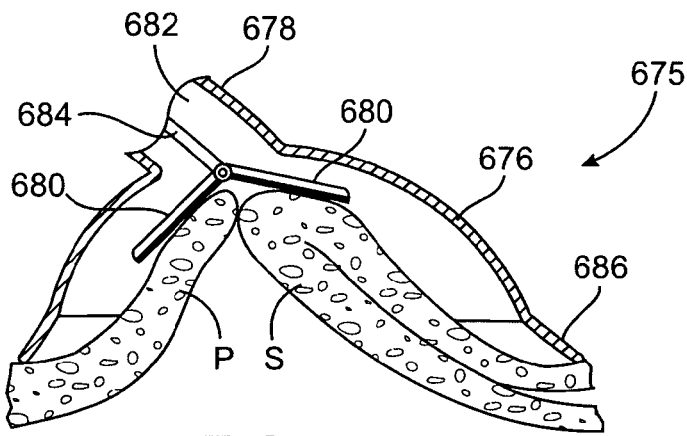

In a further embodiment depicted in FIG. 33, a bipolar clamping device (electrode structure) 680 may be integrated into the housing 676, or advanced as a separate element to grasp and weld the tissues P, S of the heart defect together. In one embodiment, the bipolar clamping element 680 may be deployed distally of the catheter housing to grasp the defect to be treated and draw it back into the housing for treatment. In this embodiment, such clamping graspers 680 may be employed separately or in conjunction with suction applied through a lumen 682 connected with the housing 676. The graspers 680 are controlled by an elongate member 684 through a lumen 682 in the catheter shaft 678. The suction operates to maintain a seal in the treatment area, and the clamp 680 can operate to not only clamp the tissue, but also to keep the treatment catheter 675 positioned at the site of the defect.

Figure 34A:
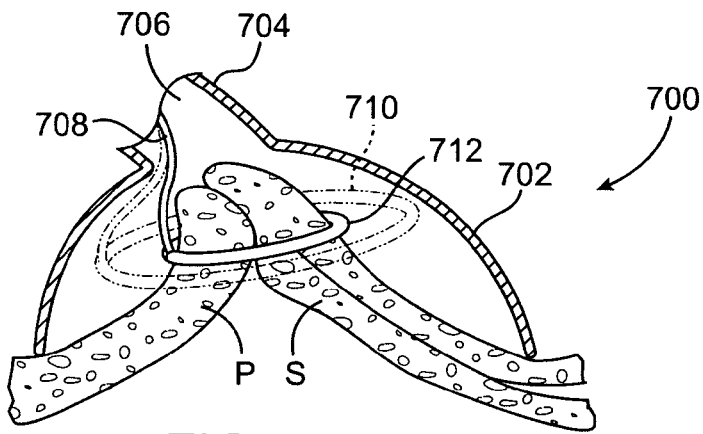
Figure 34B:
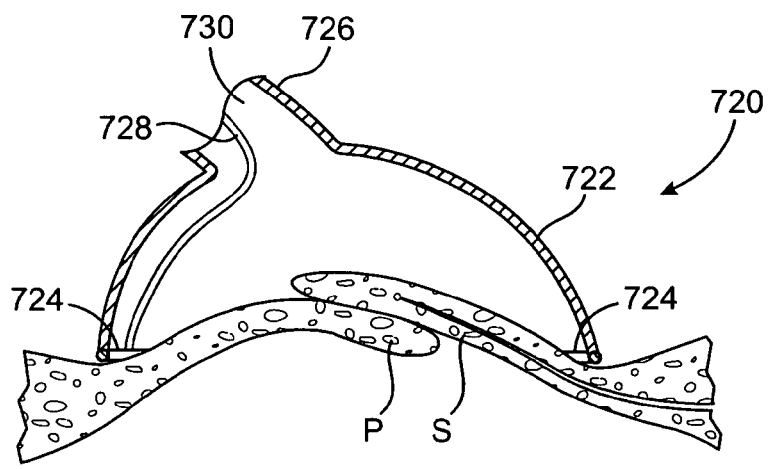

FIG. 34A shows another embodiment where a ring electrode 712 may be employed in the housing 702 or around the flange of the housing (724 in FIG. 34B) to seal tissue. In the case of the ring electrode 712 in the housing 702, it can either be fixed to the walls of the housing, or separate and deployable about the acquired tissue. FIG. 34A shows the ring electrode 712 separate from the housing 708. In some cases it may be desired to cinch the electrode from a larger diameter 710 to a smaller diameter 712 around the tissue P, S, such as a snare type device. In the case of the ring electrode 724 around the flange of the housing 722 depicted in FIG. 34B, the electrode structure can provide additional rigidity to the flange region, thereby assisting with tissue apposition while also being activated to delivery energy and seal.

Figure 35:
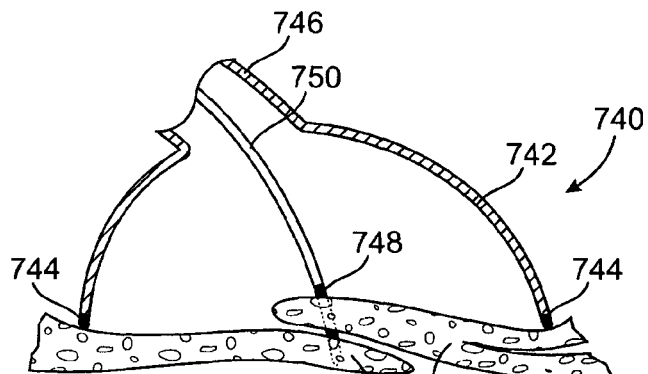
Figure 36:
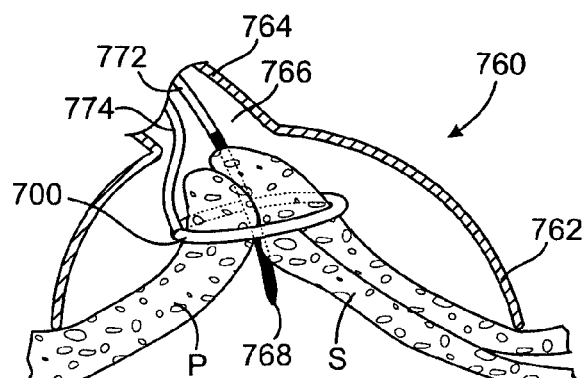

Further, the ring electrode in either configuration (cinched/snare ring or ring on outer housing) may be the return electrode in a bipolar system as shown in FIG. 35. In FIG. 35, a second active electrode 748 may be inserted into the tissue to be treated P, S while a ring electrode 744 is disposed within the housing 742 and serves as the return electrode. FIG. 36 shows an alternative embodiment where a second active electrode 768 is inserted into the treatment region P, S and a cinch or snare electrode 770 is the return electrode.

Figure 37:
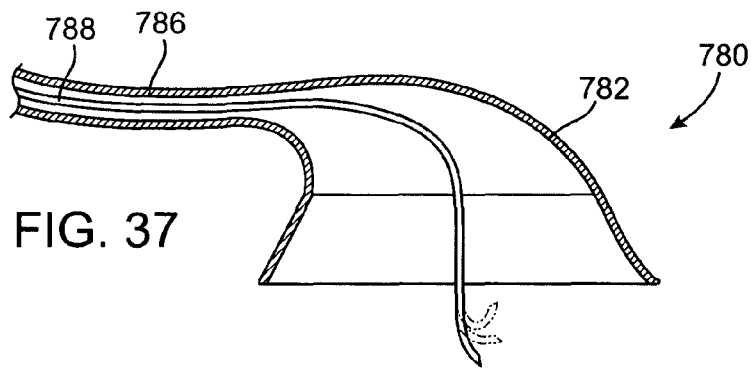
FIG. 37 shows one embodiment of an apposition device.
Figure 38C:
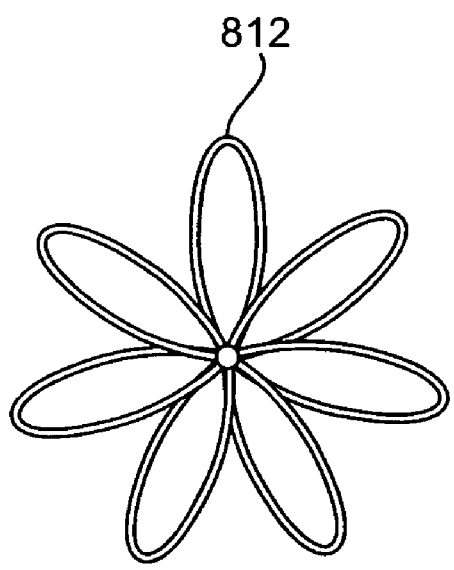
Figure 38D:
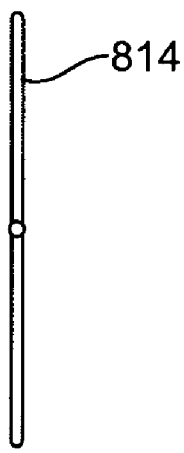

With reference now to FIG. 37, an additional embodiment shows an apposition device 780 of the present invention which may include a mechanical device 784 deployed from the housing 782, through the tissue or defect to be treated (see FIG. 38B), and capable of pulling the tissue back into apposition with the housing 782. Such a mechanical assistance device 784 can be used alone or in conjunction with vacuum apposition. The apposition device 784 would be very low profile in its "stowed" condition for placement through tissue of the defect or through the defect opening, and then deployed to an expanded condition as indicated by phantom lines, whereupon it may be drawn back toward the catheter housing 782 to tension the tissue between the catheter housing 782 (and electrode) and the expanded portion of the apposition device. One embodiment of this device shown in FIG. 38A includes a molly bolt type (or mallecott) apposition device 810 deployed through a needle 804 placed through defect or through defect tissues. The device is shown placed through tissue in FIG. 38B. Once placed through tissue, it is then expanded 808 to provide a backstop and hold tissue, and is illustrated in FIG. 38B. In yet another embodiment the apposition device may be a wire that expanded to a looped or "petal" type configuration 812 as shown in FIG. 38C and a side view in FIG. 38D. In any of these embodiments, the apposition device may be deployed through the guidewire lumen of the treatment device, or through a separate, dedicated lumen. These devices may be positioned with respect to the defect to be treated by using the positioning devices of the present invention described previously.

Figure 39A:
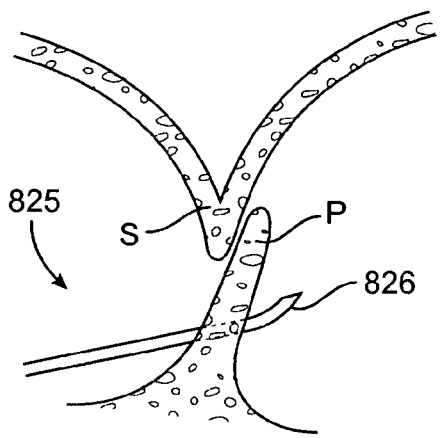
FIGS. 39A-39F show how an apposition device and a closure treatment device work together to close a layered tissue defect such as a PFO.
Figure 39B:
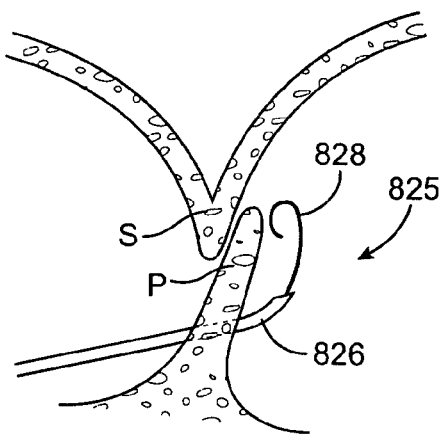
Figure 39C:
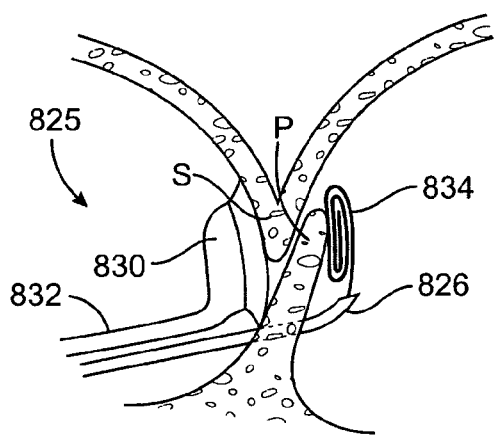
Figure 39D:
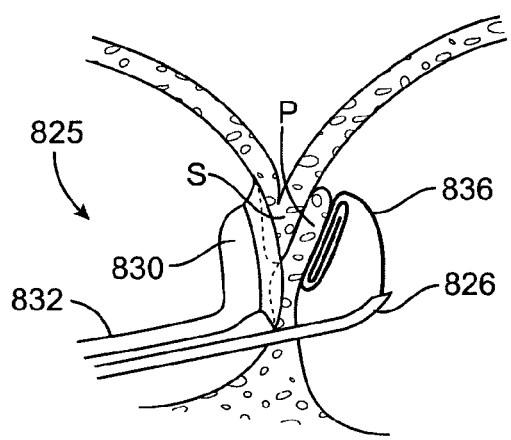
Figure 39E:
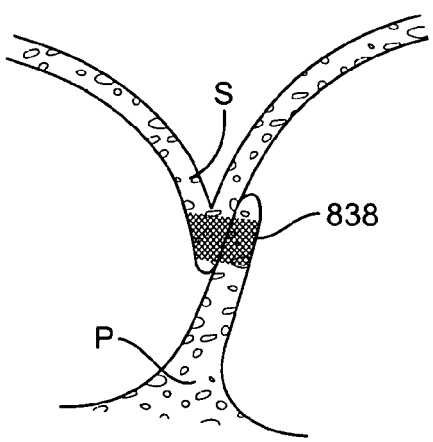
Figure 39F:
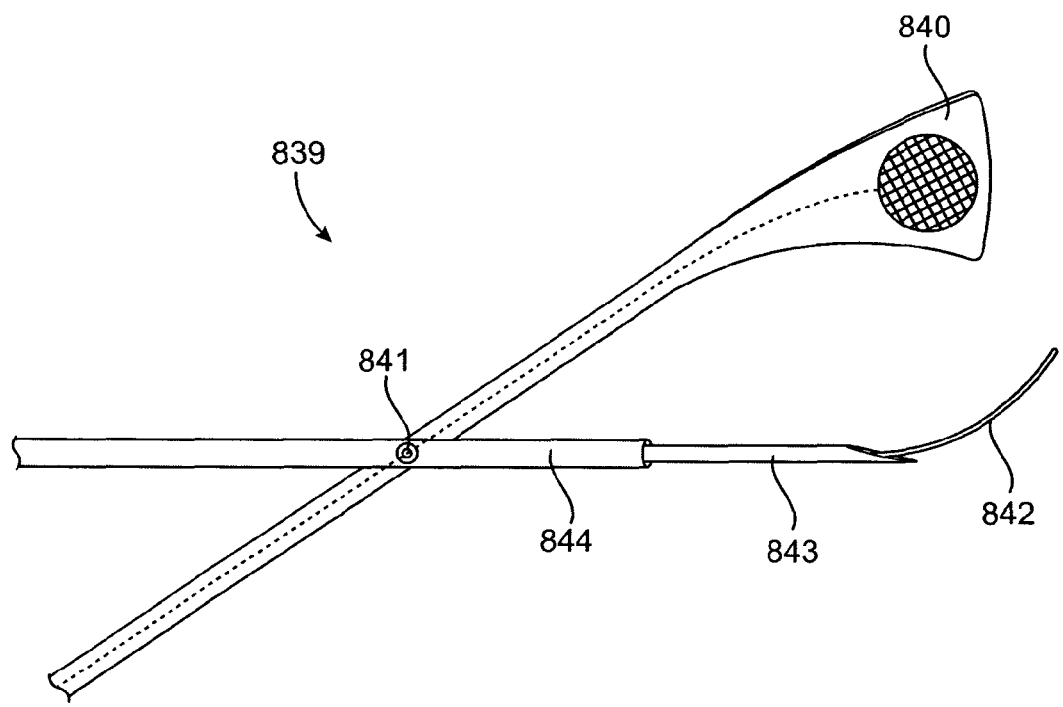

In a further embodiment, an apposition device may be deployed separately from the treatment device into the left atrium, remote from the treatment site, to "bookend" the defect against treatment catheter and thereby create enhanced tissue apposition. Such a separately deployed apposition device would preferably be low profile to allow the remote puncture site to heal naturally, without requiring a therapeutic intervention to close the puncture. FIGS. 39A-39E illustrate this with respect to a PFO closure, but several other defects in the heart could be apposed and closed in a similar manner. In FIG. 39A a needle cannula 826 is inserted from the right atrium to the left, remote from the defect opening. A tissue apposition device 828 is then deployed into the left atrium toward the site of the defect or tissues to be apposed, as shown in FIG. 39B. A treatment catheter 832 and the left atrial apposition member 834 are then brought into alignment at the site of the defect to be closed, which is illustrated in FIG. 39C. Force is applied to assist in apposing the tissue closely within the housing 830 of the treatment device 832, shown in FIG. 39E. Once the defect is closed, the treatment device 832 is removed and the apposition device 836 is retracted into the needle cannula 826, after which time the needle cannula 826 is removed and nothing is left on the left atrial side of the heart. The needle cannula entry site may be left to close naturally and the layered tissue defect is also closed as seen in FIG. 39E. Another embodiment is shown in FIG. 39F where a needle like structure 843 is used to penetrate the tissue defect. An apposition member 842 is then released from the needle structure 843 to provide a backstop. A pivot on the device 841 can then be actuated, bringing the treatment housing 840 and backstop 842 together. The closure treatment may then be applied. After the closure treatment is completed, the backstop 842 may be retracted into the needle structure 843, and both are withdrawn into a sheath 844, and the entire device is removed from the patient or moved to another treatment location.

Figure 39G:
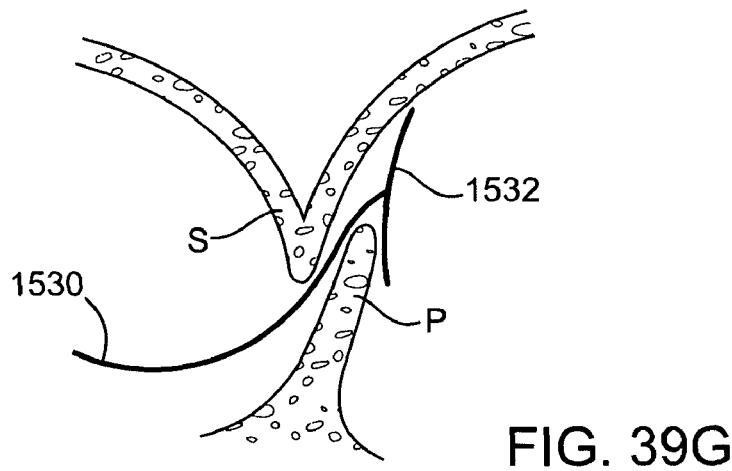
FIGS. 39G-39I show another apposition device and closure treatment device working together to close a layered tissue defect such as a PFO.
Figure 39H:
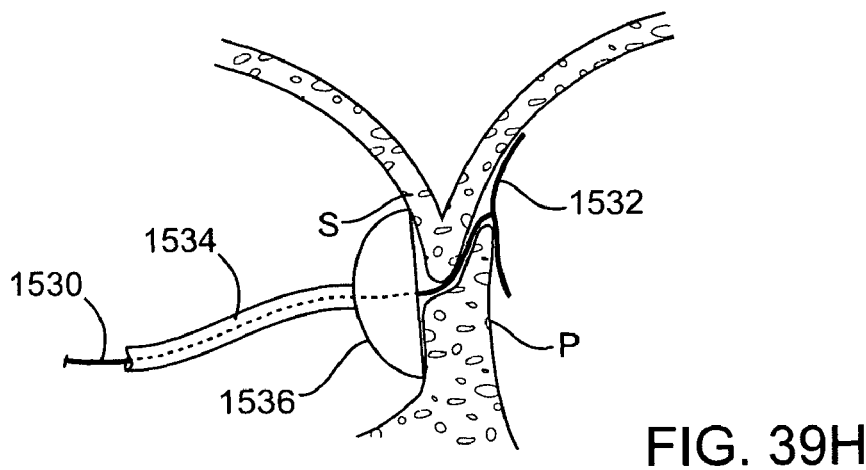
Figure 39I:
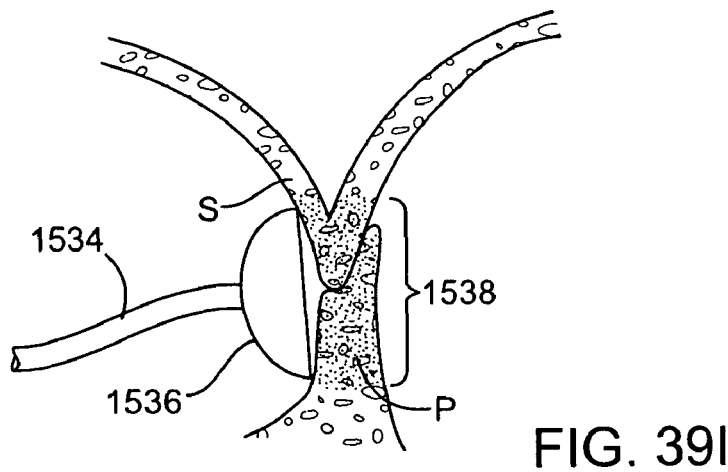

FIGS. 39G-39I illustrates another embodiment for enhanced apposition including a elongated guidewire 1530 with a flexible T-shaped distal end 1532. In FIG. 39G, the elongated guidewire 1530 is placed through the PFO tunnel until the T-shaped end exits the tunnel on the left side of the heart. The flexible whiskers 1532 which form the T-shaped end are then free to expand outwardly and then can serve as an anchor point for the guidewire 1530. In FIG. 39H, the elongated guidewire 1530 is retracted which results in the whiskers 1532 forcing the primum P against the secundum S, thereby reducing the gap therebetween and permitting better fusing of the two layers. A closure treatment device 1534 is then delivered to the treatment site, here, delivery of the closure treatment device 1534 is advanced axially over the guidewire 1530. The closure treatment device 1534 then applies a treatment to the tissue defect, partially closing the defect, except for the region where the guidewire 1530 rests. In FIG. 39I, after a partial closure of the defect is obtained, the guidewire 1530 is removed from the tunnel and the closure device 1534 may complete the treatment by sealing the PFO and fusing the primum P and secundum S together 1538.

Figure 40:
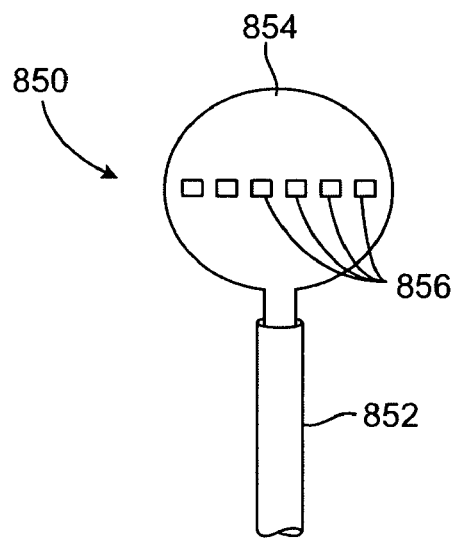
FIG. 40 shows an apposition device comprising magnets.
Figure 41:
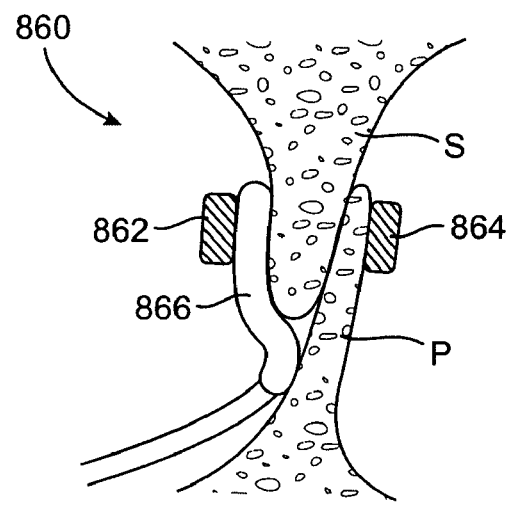
FIG. 41 illustrates how magnets on either side of a PFO are used to bring the tissue layers together.
Figure 42:
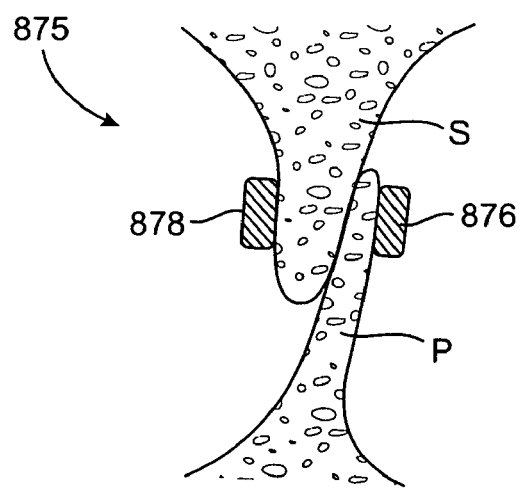
FIG. 42 shows magnets permanently implanted in order to close a PFO.

Using a similar technique, another approach to applying the required tissue compression prior to defect closure utilizes magnetic attraction as shown in FIGS. 40-42. By placing magnets or electromagnets on either side of the layers of tissue that require apposition, a compressive force can be applied without requiring a physical link between the sides of the tissue. Any combination of ferromagnetic material, magnet material, and/or electromagnetic material can be used to create the desired force. While not required, the use of rare earth permanent magnets such as Samarium Cobalt (SmCo) or Iron-Neodymium (NdFeB) provide substantial levels of magnetic flux for a given volume of material and are implantable grade materials. Coupling such a magnet with a ferromagnetic counterpart can simplify the use of magnetic attraction to create force because orientation of the ferromagnetic portion of the coupling does not require a specific orientation relative to the permanent magnet in order to create an attractive force. Further, use of an electromagnet can be beneficial since it can be selectively activated (turned on and off).

The magnet and/or ferromagnetic components used for such an application can be in singular elements, or an array of smaller elements that may be more easily delivered to a remote location through a patients vasculature. For example, magnetic components 856 may be coated or formed for implant in a human body, loaded into a catheter 852 as shown in FIG. 40. The assembly 850 may be delivered to relevant locations while contained, and then released at the desired location with respect to the defect to be treated, and deployed.

Alternatively, as shown in FIG. 41, magnetic elements 862, 864 are placed on either side of a PFO (one in the right atrium and one in the left atrium). An energy treatment catheter 866 is placed between the magnets 862, 864 in the right atrium to deliver the tissue welding treatment once the tissue or brought together by the magnetic force. Optionally, the magnet on the right atrium 862 could be incorporated into the energy treatment catheter. In this embodiment, the magnetic device deployed in the left atrium 864, could be placed with a similar needle catheter delivered remote from the defect to be treated, and once magnetic apposition was achieved and the defect closed, the left side magnetic 864 component would be removed.

It is also within the scope of the present invention, as shown in FIG. 42, to permanently implant a magnetic coupler 875 to close the anatomic defect. The magnetic coupler would have a first magnetic element 876 placed on the left side of the defect, and a second magnetic element 878 placed on the right side of the defect. One or more inflatable balloons may be used as deployment tools, for example to separate each magnetic element until proper positioning is obtained. Once each element is properly placed, the balloon can be deflated and removed, leaving the magnetic coupling elements in place, and able to attract each other to seal the defect.

B. Isolating Treatment Site. The ability to appose tissue and create a treatment area conducive to welding tissue may be enhanced by the application of negative pressure, i.e. vacuum, at the treatment site. In addition, it may be desirable to infuse fluid into the treatment site for a variety of reasons.

Sealing. Certain features of the housing may be constructed to assist in creating a robust seal at the tissue interface, and maintaining that seal for the duration of the treatment. To balance the housing features that allow for greater tissue apposition (e.g. a more resilient housing), the following features may be incorporated into the housing flange.

Figure 43:
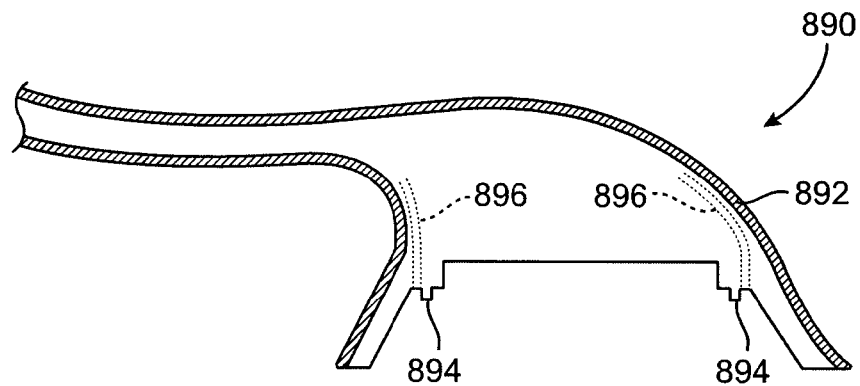
FIG. 43 shows additional features on the housing to help with tissue apposition.

Additional "grippers" or protrusions 894 in the rim of housing 892 increase tissue apposition to the device 890. An additional vacuum lumen 896 in the housing rim 892 may also be useful to distribute the vacuum force toward the outer edge of the housing at the housing/tissue interface. This is illustrated in FIG. 43.

Figure 44A:
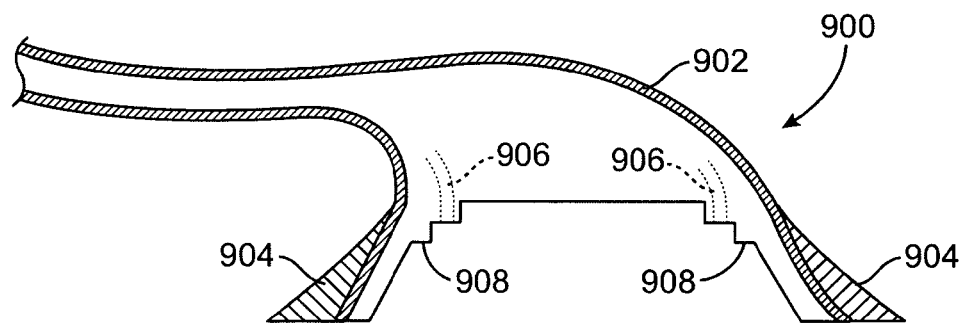
FIGS. 44A and 44B show other features on the housing that help with tissue apposition.
Figure 44B:
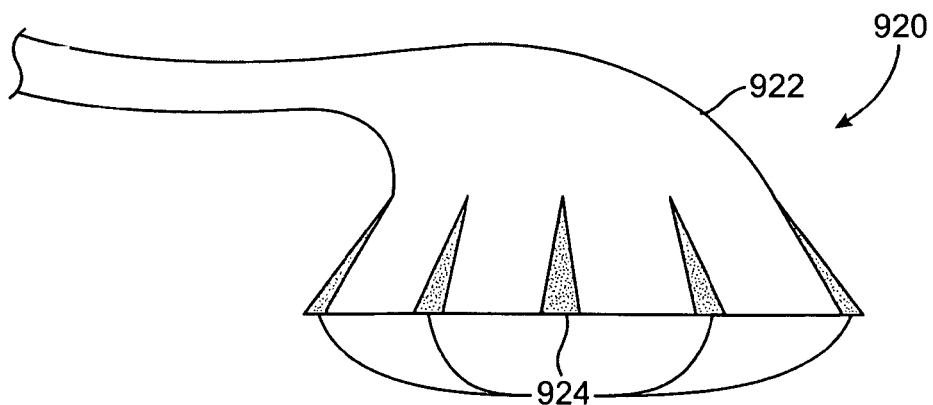

Alternatively, as illustrated in FIG. 44A, the location of the grippers 908 and the additional vacuum port 906 may be reversed. Furthermore, a gusset 904 may be added to the housing 902 to increase the sealing force of the flange, but still keep the housing flexible. Gussets 924 may be placed circumferentially around the outer housing flange 922 at various locations, and this is seen in FIG. 44B.

Figure 45A:
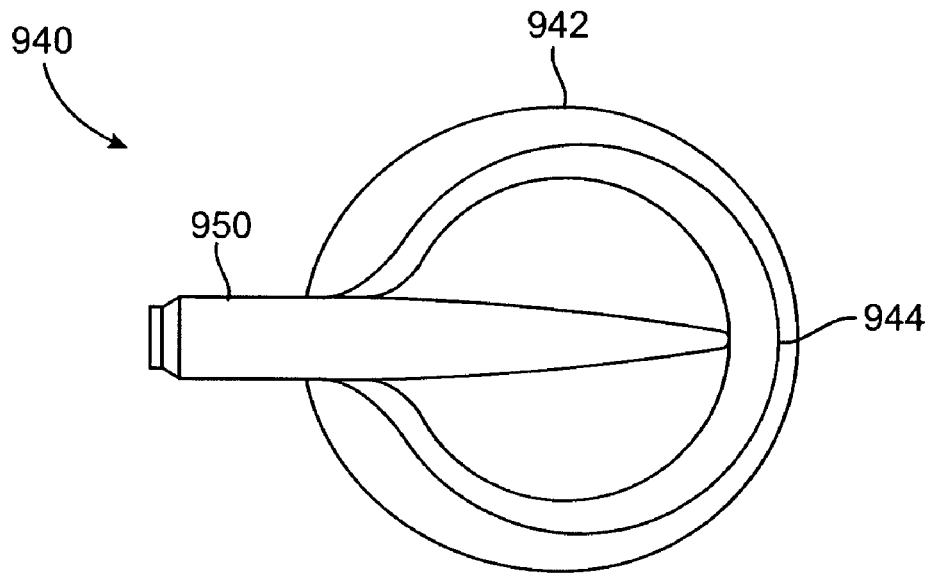
FIGS. 45A-45C show a preferred embodiment of the closure device housing.
Figure 45B:
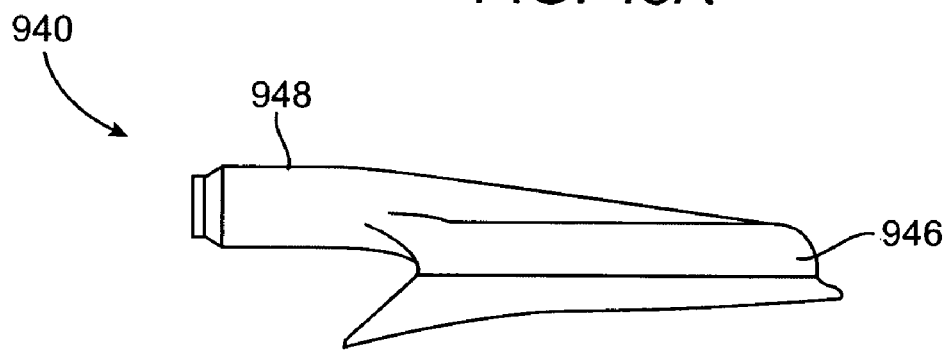
Figure 45C:
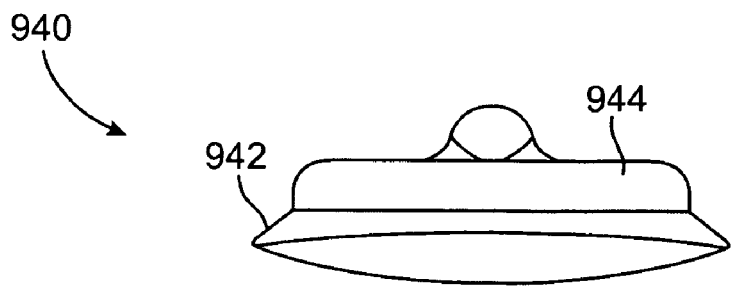

FIGS. 45A-45C show a preferred embodiment of the housing 940. FIG. 45A illustrates a top view of the housing which preferably has a flange or skirt 942 having a diameter of 0.921 inches and the housing itself has a diameter 944 of 0.730 inches. An elongate member 950 represents the transition from the housing 940 to a catheter shaft. The housing has a slightly tapered profile when observed from the side in FIG. 45B. The distal tip of the housing 946 is the lowest point of the taper, and preferably has a height of 0.140 inches while the proximal end of the housing 948 is higher and is preferably 0.297 inches high. A front view of the housing is seen in FIG. 45C and this view shows the flange or skirt 942 connected to the housing 944.

Figure 45D:
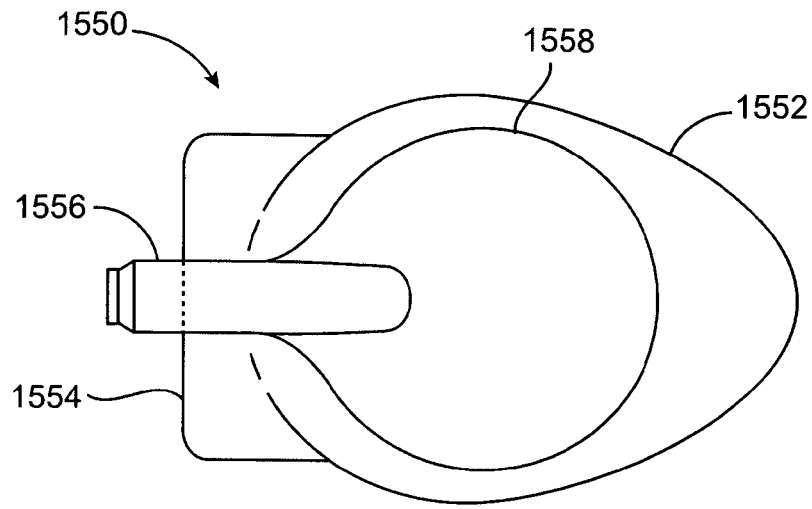
FIGS. 45D-45F show another embodiment of the closure device housing.
Figure 45E:
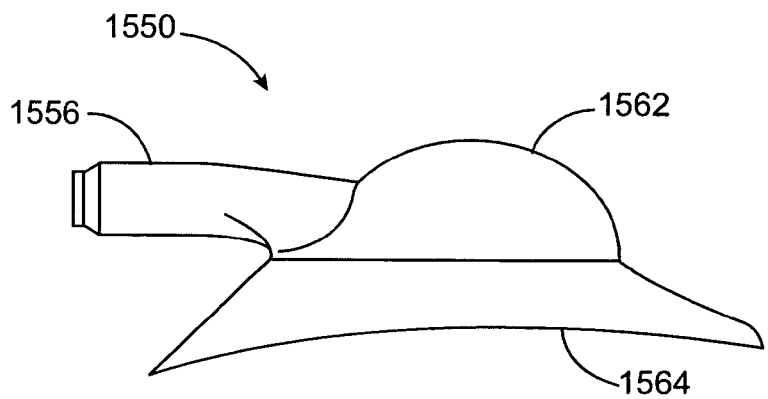
Figure 45F:
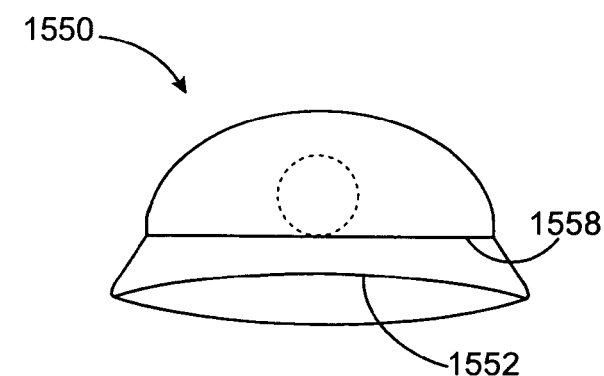

Another embodiment of the housing is illustrated in FIGS. 45D-45F. In FIG. 45D, a top view of the housing 1550 is shown. The housing 1550 here has a nose-like front projection 1552 and a rectangular-shaped 1554 rear projection. The housing is typically attached to an elongate catheter shaft 1556. Both projections 1552 and 1554 form a skirt around the housing 1550, attached along the housing rim 1558, and that helps the housing to match the tissue defect anatomy and appose the defect. FIG. 45E is a side-view of housing 1550 showing the skirt 1564 and a domed housing top 1562. A front view of the housing 1550 is shown in FIG. 45F which illustrates the skirt 1552 attached with the housing rim 1558.

Infusate. Successful welds of heart defects may be achieved in the presence of infusate or drip fluids into the treatment region, as described in application Ser. No. 10/952,492, the full disclosure of which has previously been incorporated herein by reference, to mediate the moisture content of the treatment area and maintain patency of the catheter lumens. Infusate is used primarily to prevent blood from stagnating within a treatment device distal housing and thereby clotting. By providing constant infusate flow, stagnation is avoided. Heparin can also be added to the infusate to further minimize clotting. Alternatively, welds of heart defects have also been achieved with relatively "dry" tissue (low or little infusate).

For example, in the event that the use of an infusate is desired, the following variables may affect the efficacy of the tissue weld, namely, type of infusate (saline, D5W (Dextrose 5% and water) or G5W (Glucose 5% and water), rate of infusion, flow distribution at tissue interface (pattern, consistency), temperature of infusate and the like. In an exemplary range, infusion may be used in the following range 0-30 ml/min, and more particularly in the range of 1-10 ml/min. The infusate is then aspirated from the treatment site via the vacuum lumen. The vacuum suction creates a continuous draw of flush through the infusion lumen, passing through the distal housing, and back out the vacuum lumen, for example a passive or "closed loop" infusion. The infusate is then collected in a vacuum canister. Operation and further detail on the infusion of fluid can be found in related application Ser. No. 10/952,492, incorporated herein by reference. Adequate vacuum seal can be determined by observation of the distal housing under fluoroscopy (lack of movement, "flattening" as determined by imaging of fluoroscopic markers or echogenicity of housing), and observation of the color of the fluid suctioned to the vacuum canister (e.g. by a change from blood to clear fluid as the dominant fluid suctioned to the vacuum canister (fluid changed from red to clear). Although a complete seal is desirable, an example of a substantial seal that may still include an "acceptable leak rate" is in the range of 0-150 ml/min, for example, in the range of 1-30 ml/min. This leak may be attributable to physiologic phenomena, as well as mechanical issues with the housing seal against the tissue.

C. Energy Application for Defect Closure: Electrode Design and Energy Algorithm Various parameters can be controlled to achieve the most advantageous result in closing a PFO or other defect in the heart with energy. As discussed above, greater tissue apposition can function to increase the likelihood of consistently welding the PFO tissues (primum and secundum), in a clinically acceptable procedure time. In addition to greater tissue apposition, various parameters related to the power algorithm can be controlled and optimized. Certain parameters include developing a feedback loop to ensure enough power is delivered to achieve the desired closure (plane of welding), that the power delivery does not lead to unwanted "pops," that the power delivery does not lead to impedance spikes of the kind that prohibit additional power delivery to tissue within the specified procedure time, and the like. Others include design of the electrode, including the size, thickness and other physical features that effect energy delivery. The treatment device and the power system of the present invention are depicted in FIG. 20 where the power supply 254 hooks into port 282 with a standard medical electrical connector.

Electrode Design. The configuration of the electrode may play a role in optimum energy delivery. Certain features of an electrode or heating element that may affect closure (welding) include, element density, geometry, size, current density, surface features (gold plating for radiopacity, coatings, electropolishing of conductive surfaces), location of the power connection, and points of insulation on the element.

For example, a larger electrode, although able to treat a greater area of tissue, requires more power and therefore is less efficient, and may lead to additional conduction in the tissue to areas of the heart that the procedure is not intended to effect. An electrode design that is matched (size, capacity) to provide "localized energy density" to the intended treatment region can function to limit the power required to achieve the intended result, and therefore a more efficient, safer lesion is created.

Figure 46:
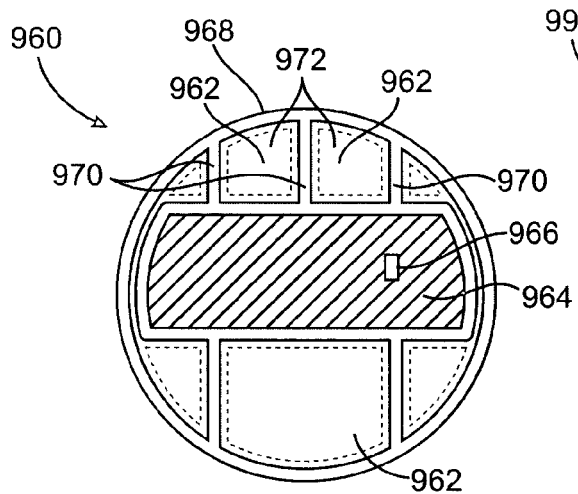
FIGS. 46-49A show various embodiments of electrode configurations.
Figure 48:
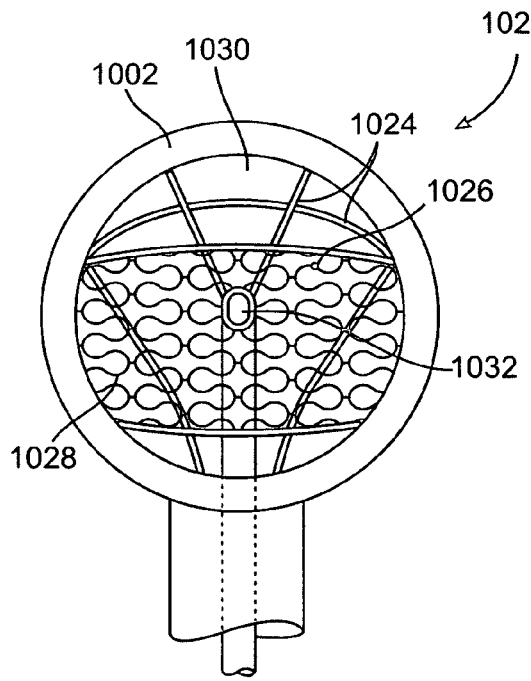

For example, in FIG. 46, a banded electrode 964 may be adapted to concentrate the power delivery at the point over which the defect comes together. This band can either be created by cutting an electrode pattern that is in the desired shape or masking a larger electrode such that only the desired band of active electrode is exposed. In FIG. 46, banded electrode 964 is cut into a rectangular shaped piece with a guidewire exit port 966 running through the electrode 964. Various other portions around the electrode and housing are insulated 962 so that energy is only delivered over the banded electrode 964. Additionally, openings within the electrode 972 allow vacuum to be applied for tissue apposition and struts 970 connect the electrode 964 to the housing 968 and help provide support. FIG. 48 shows an alternative embodiment of the banded electrode 1028 wherein the active electrode band pattern has been cut into the desired shape, here an undulating wave-like pattern. Additional features such as an exit port for a guidewire 1032, vacuum ports 1030, a thermocouple 1026, insulated struts 1024 for support and a housing flange 1022 have previously been discussed.

Figure 47:
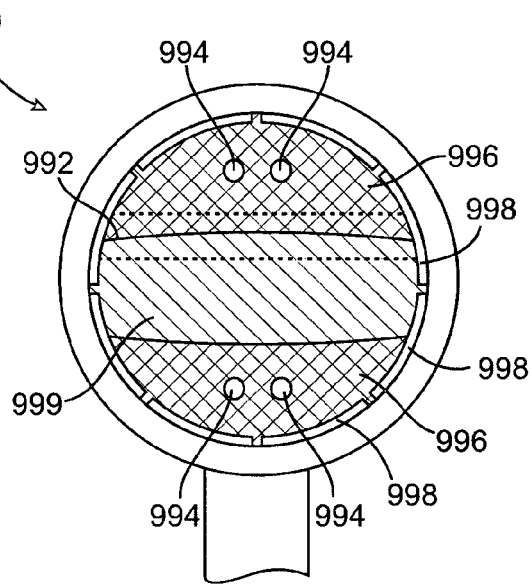
Figure 49:
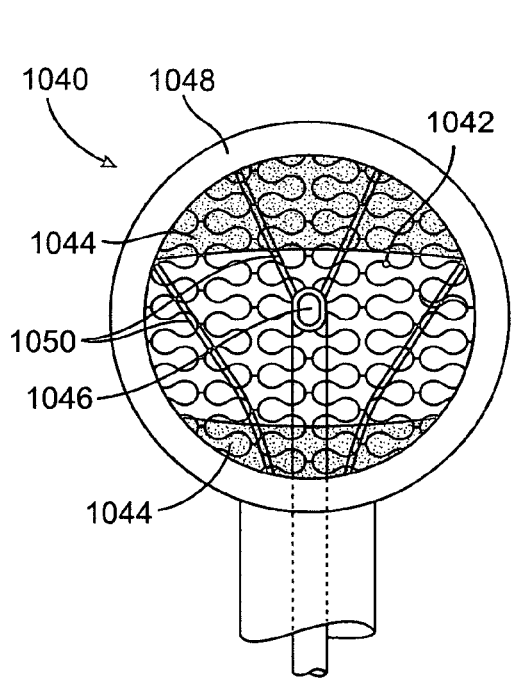
Figure 49A:
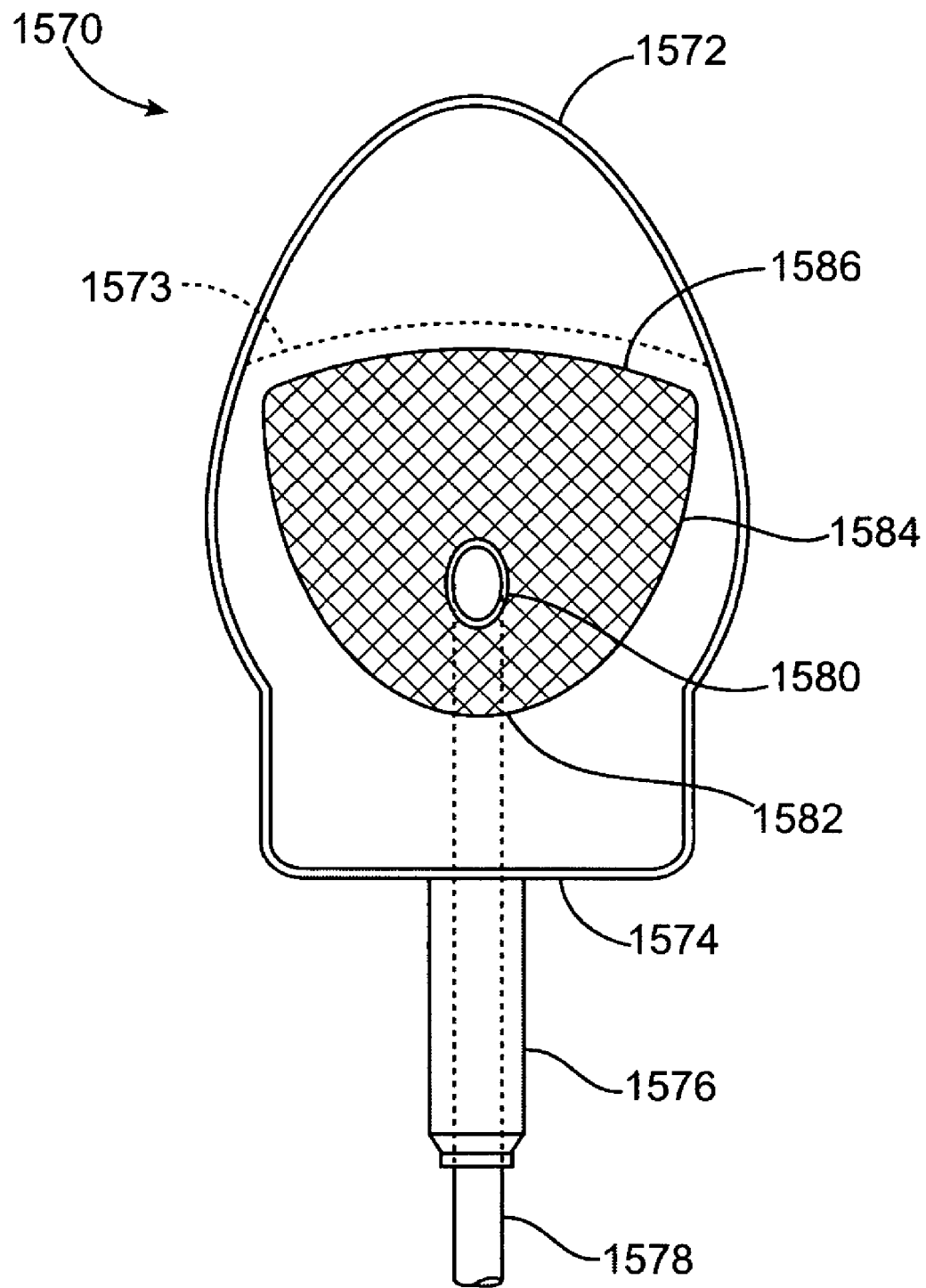

FIGS. 47 and 49 on the other hand employ the masking embodiment. In FIG. 47, portions of the electrode are masked 996 so that energy is only delivered via an active region 999. Other features such as vacuum ports 994, support struts 998 are also utilized. FIG. 49 shows a variation of masking, where portion of the undulating wave-like pattern previously discussed above are masked to control energy delivery. In FIG. 49, masking 1044 controls where the active electrode region is. Typical electrode measurements are in the range of 30 mm wide by 20 mm tall, for example 15 mm wide by 9 mm tall. The total area of the electrode may vary depending on the chosen geometry. Electrodes may be configured in a variety of shapes, including elliptical, circular, rectangular, triangular, or have geometries that are a combination of those approximate shapes in order to best fit the geometry of the tissue to be treated. An alternative electrode embodiment is illustrated in FIG. 49A. In FIG. 49A, a housing 1570 is disposed on distal end of an elongate catheter shaft 1576. The housing 1570 has a nose-like protrusion 1572 and a rectangular shaped rear protrusion 1574. The nose-like protrusion 1573 may also be moved closer to the electrode 1586, as shown by dotted line 1573, in order to better appose the tissue. A partially oval shaped electrode 1586 is disposed in the housing 1570 and a guidewire lumen 1578 port 1580 exits through the electrode 1586. The electrode 1586 is adapted to more accurately match PFO anatomy. In the case of a PFO, the electrode is adapted to treat PFOs ranging in size from 1 mm to 30 mm and more typically in the range from 3 mm to 26 mm.

Figure 50A:
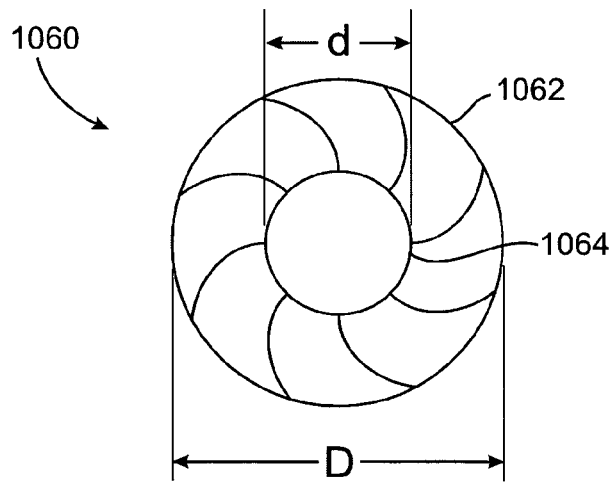
FIGS. 50A-50B show a variable masking means.
Figure 50B:
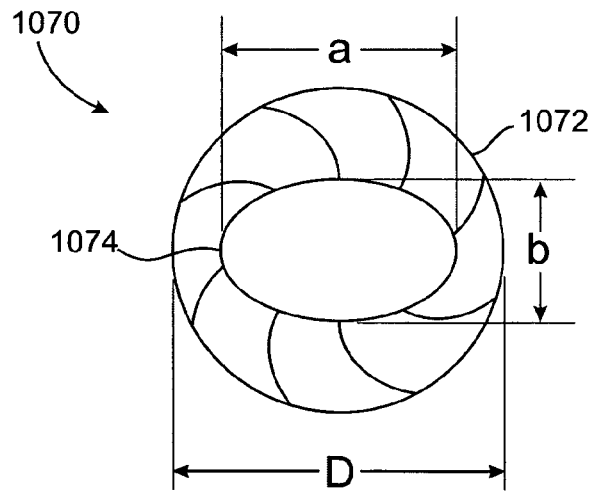

Masking may be applied by spraying or dip coating and typically employs a silicone layer, although other methods and materials are well known in the art. Alternatively, it may be desirable to design the masking element on the distal catheter housing such that it can be variable wherein the mask opening only exposes the desired amount of septal tissue to the chosen form of energy. The opening may be round, oval or other shapes, such as a crescent, to mimic the defect to be treated. Illustrative embodiments of this are shown in FIGS. 50A and 50B. For example, FIG. 50A shows a variable mask wherein the inner diameter 1056 can be controlled, while in FIG. 50B an elliptically shaped aperture 1074 is controllable.

Figure 51:
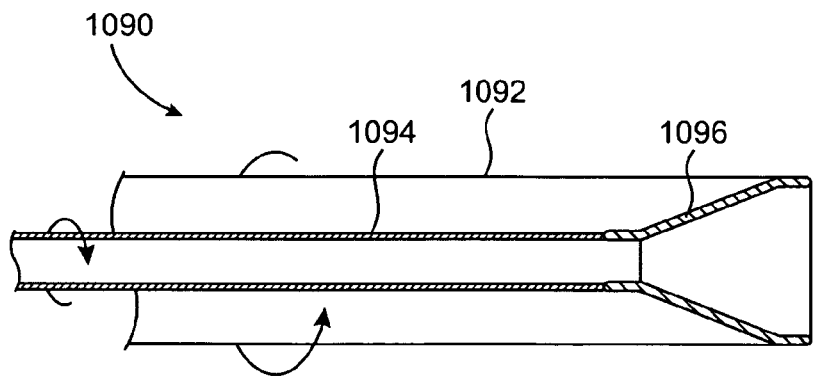
FIG. 51 shows a means for actuating the variable masking of FIGS. 50A-50B.

In operation and illustrated in FIG. 51, a treatment catheter 1090 may be formed by using coaxial shafts 1092, 1094 that allow relative axial rotation to twist an elastomeric tube 1096 or otherwise create a valved effect (similar to an iris valve). Final mask shape is then achieved by rotating one shaft relative to the other until the desired mask shape is reached. The two shafts can then be locked together to prevent the shape of the mask from changing during treatment.

Figure 51A:
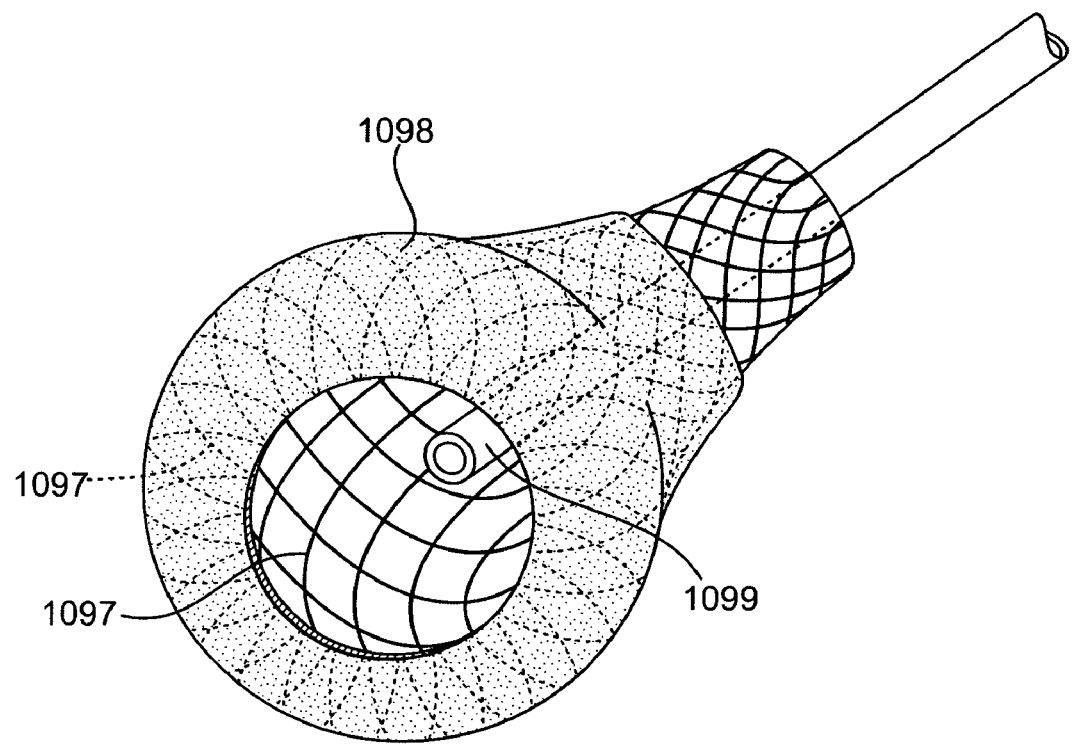
FIG. 51A shows a mesh electrode embodiment.

In a further embodiment, a mesh electrode 1097 is shown in FIG. 51A, and may be employed, having an insulation coating 1098 or sleeve. In use, tissue would be drawn into the cavity created by the electrode and energy delivered. Alternatively, the insulating sleeve may be withdrawn, exposing the desired amount of active electrode.

Figure 52A:
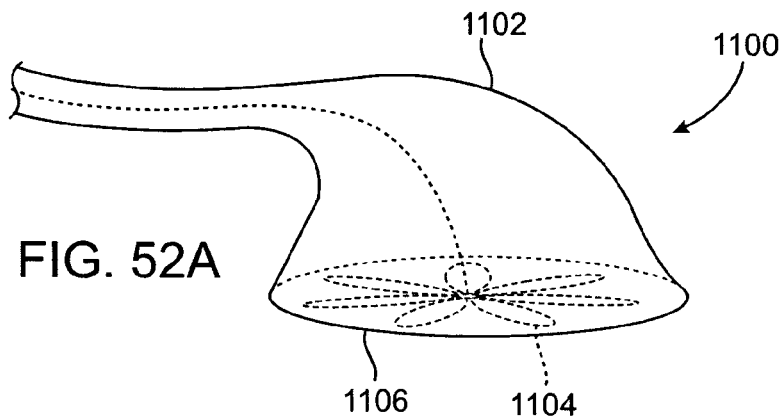
FIG. 52A-52B show a looped or petal electrode configuration.
Figure 52B:
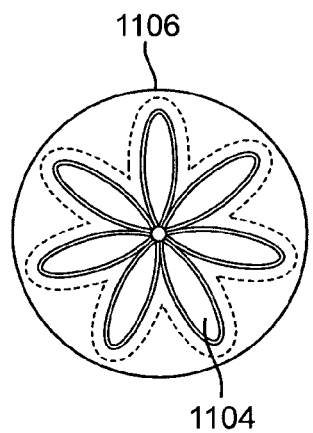

FIG. 52A illustrates a further embodiment of an electrode having lobes or "petals" 1104 which may be employed to the desired size, either by using separate loops, or feeding out a length of preformed nitinol wire to achieve the desired configuration. Because an electrode such as this can be deployed once a seal by the catheter housing 1102 has been obtained, it is possible for the user to apply a certain amount of directional force with the electrode against the tissue, which may be useful in creating optimal tissue apposition with the target, on its own, or in conjunction with other apposition devices and techniques disclosed herein. A bottom view of the housing 1102 emphasizing the petals 1104 is seen in FIG. 52B.

Figure 53:
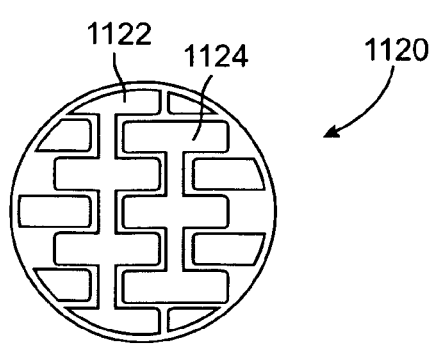
FIGS. 53-54 illustrate various electrode embodiments.
Figure 54:
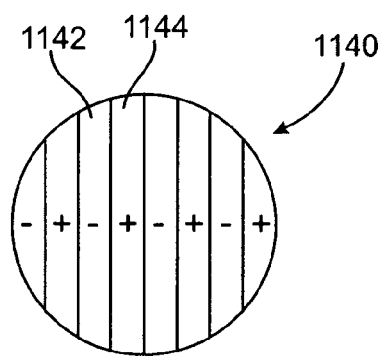

In a further example and with reference to FIG. 53, the active electrode may be an alternating current bipolar electrode (requiring less energy, and in a more localized manner), and configured as either an electrode commensurate with the size of the housing, or less than the size of the housing, by masking, otherwise insulating, or cutting the electrode to a smaller size. Interdigitating active 1122 and return 1124 electrodes can be laid out on a planar electrode substrate. Alternating active 1142 and return 1144 electrodes across a planar electrode substrate may also be employed as seen in FIG. 54.

Figure 55:
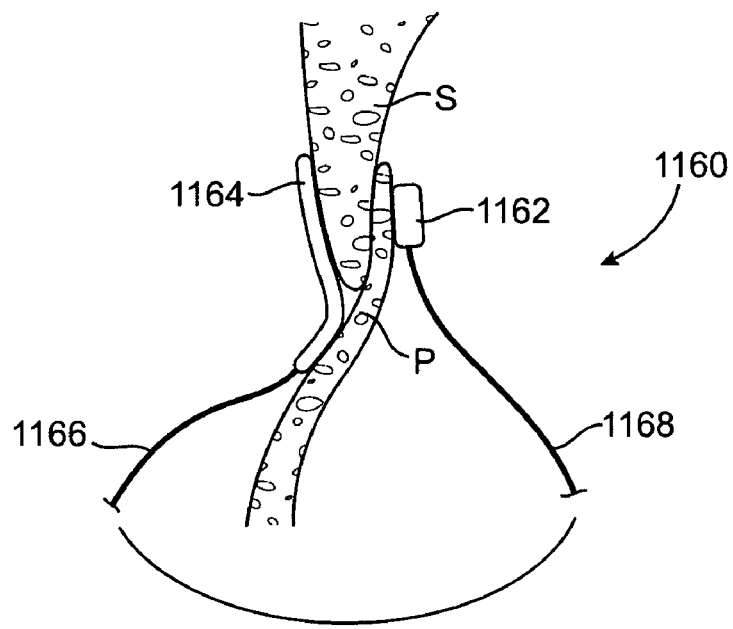
FIG. 55 shows a bipolar configuration.
Figure 56:
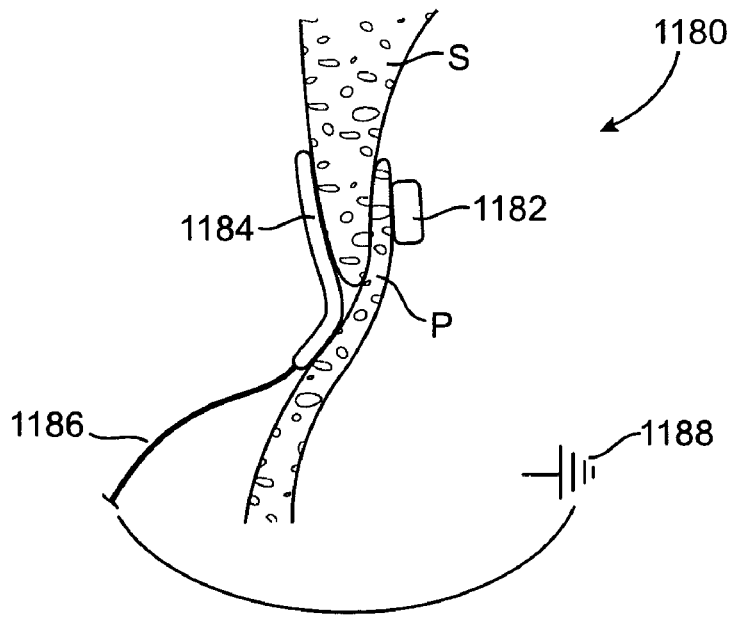
FIG. 56 shows a monopolar configuration.

The use of RF energy to generate a weld of a defect in conjunction with the use of a magnetic coupler to create opposing force could allow the RF system to be either monopolar or bipolar depending on the configuration. For example as depicted in FIG. 55, each half of the magnetic couple 1162, 1164 could be one pole of a bipolar RF circuit. In addition, only one of the portions of the magnetic couple 1184 is used as part of a monopolar RF circuit and this is illustrated in FIG. 56. Further combinations that include either one or more of the components of the magnetic couple in either a monopolar or bipolar RF circuit are also possible. It is within the scope of the present invention to also size, mask or otherwise modify the electrode configurations described in co-pending application Ser. No. 10/952,492, previously incorporated herein by reference.

Figure 57:
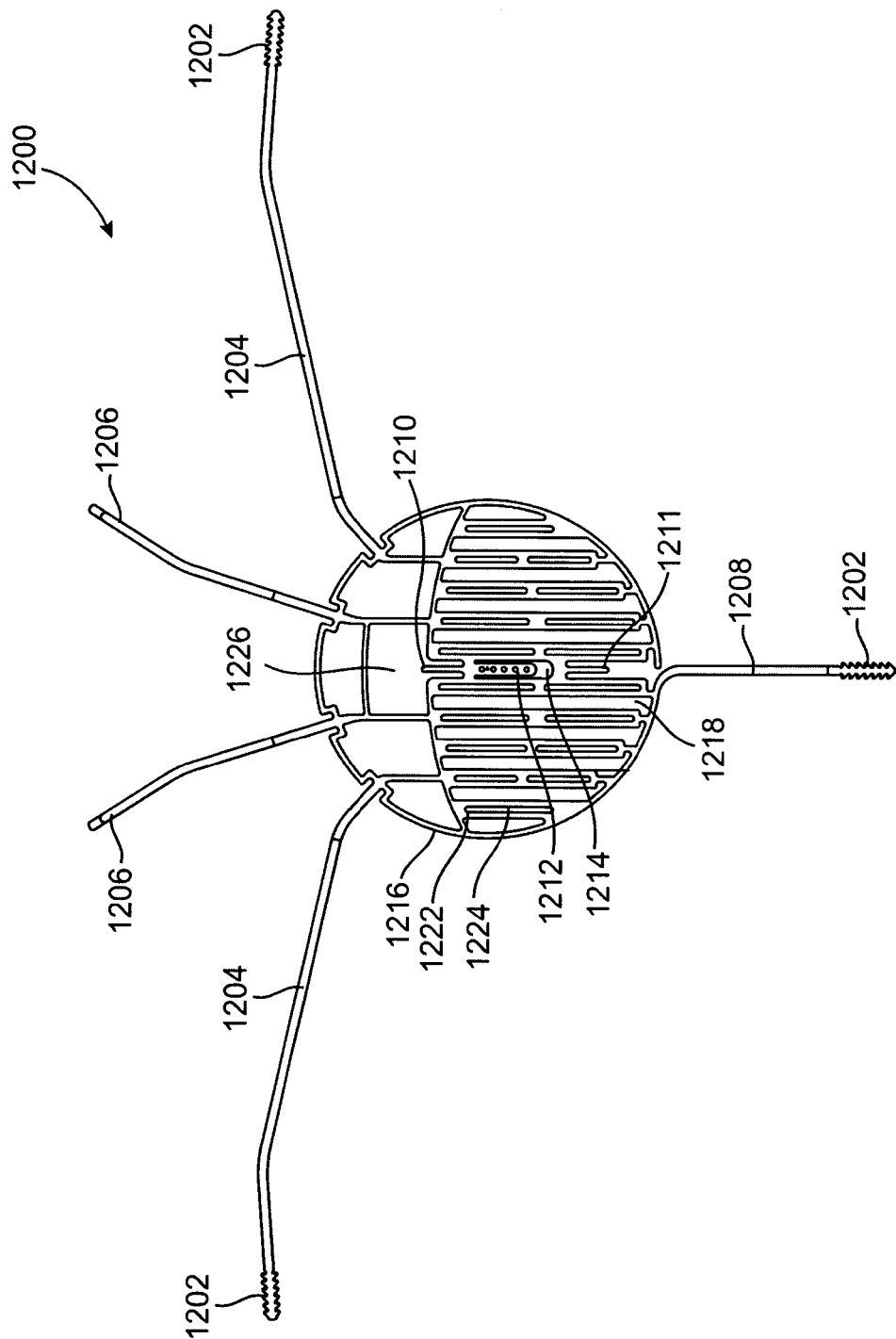
FIG. 57 shows a preferred embodiment of the electrode.

A preferred electrode embodiment is shown in FIG. 57. An electrode 1200 is illustrated prior to attachment with a catheter housing. Here, struts 1204, 1206, 1208 extending from the electrode are designed for attachment to the housing in order to connect the structures with one another. Struts 1204, 1206 and 1208 also serve to provide support for the housing. Barbs 1202 may be employed on the struts 1204 and 1208 to help attach them to the housing. A monopolar electrode is formed from a series of parallel bars 1222 separated by a slit 1224. A set of bars 1222 is separated from an adjacent set of bars by another gap 1218. An outer perimeter is formed by a ring 1216 and apertures 1226 allow vacuum to be applied as well as administration of an irrigation fluid. Tabs 1210, 1211 and 1212 allow a piece of tubing to be attached to the electrode to facilitate guidewire entry and exit from the housing. In a preferred embodiment, not intended to be limiting, the electrode has a thickness of approximately 0.0029 inches and struts 1204, 1206 and 1208 are typically about 0.020 inches wide by 0.004 inches thick. Ring 1216 width is about 0.012 inches, while the bar 1222 width is approximately 0.040 inches and slits 1224 are about 0.012 inches with gaps 1218 being about 0.030 inches wide. The slits in this embodiment allow suction to be applied through the electrode, help to minimize tissue from adhering to the electrode surface and create an edge from which RF energy is delivered to tissue.

Figure 57A:
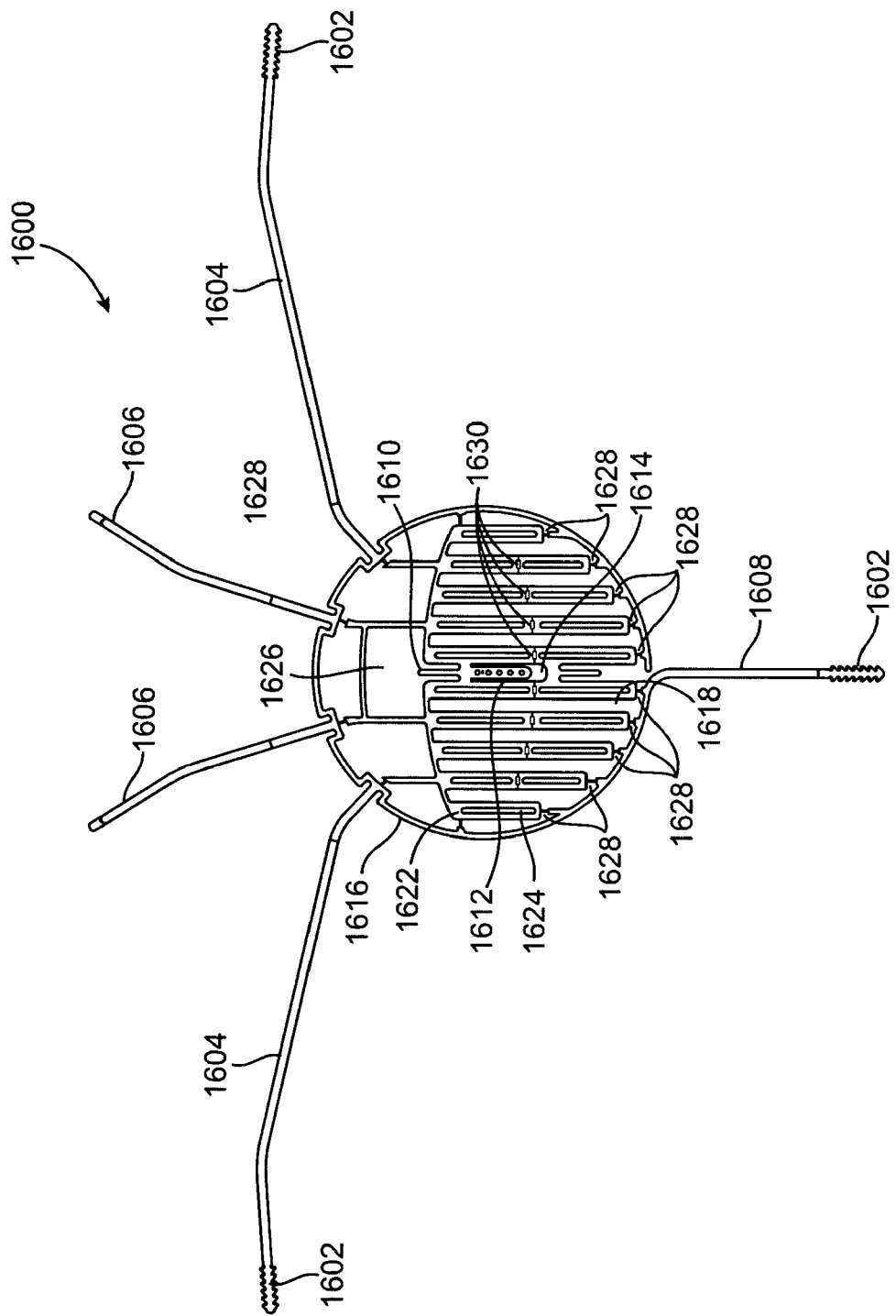
FIG. 57A illustrates a hinged electrode with flexible connections to the housing.

A floating electrode embodiment is illustrated in FIG. 57A. In this figure, an electrode 1600, unattached with a catheter housing is shown. Struts 1604, 1606 and 1608 are connected with the housing and help to provide support to the housing during tissue apposition and/or vacuum application. Barbs 1602 on the struts 1604 and 1608 also help to connect the struts 1604 and 1608 to the catheter housing. A parallel series of bars 1622 is separated by a slit 1624 therebetween, forming a monopolar electrode. Each set of parallel bars 1622 is separated from an adjacent set off bars by another gap 1618 and an outer perimeter is formed by a ring 1616. The electrode bars 1622 connect with the perimeter 1616 via a flexible elastomeric coupling 1628 such as silicone. The flexible couplings 1628 allow the electrode to float and therefore the electrode can adapt to various tissue defect anatomies more effectively by compensating for changes in tissue thickness or height. Additionally, the electrode bars 1622 are hinged 1630, allowing further adjustability of the electrode surface to accommodate are more diverse range of tissue anatomies. Other aspects of this electrode embodiment include apertures 1626 within the electrode which allow vacuum to applied as well as administration of irrigation fluid. Tabs 1610 and 1612 allow tubing to be attached to the electrode to facilitate guidewire entry and exit from the housing. Electrode dimensions generally take the same form as the electrode described in FIG. 57 above.

Figure 58A:
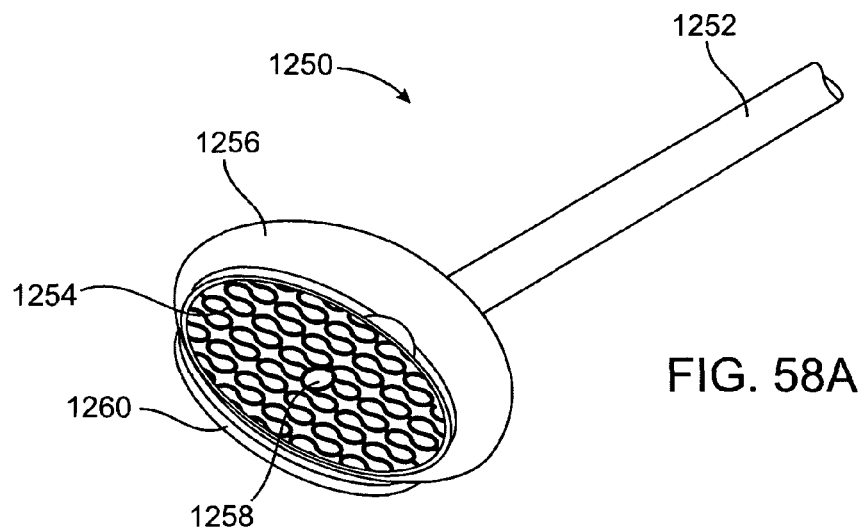
FIG. 58A-58C show the electrode disposed in a housing and a portion of the guidewire lumen exit aperture.
Figure 58B:
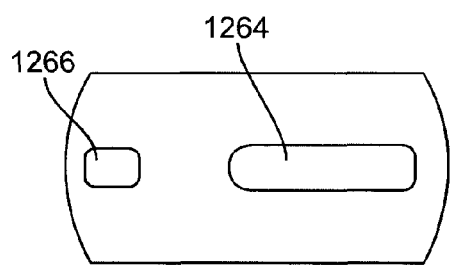
Figure 58C:
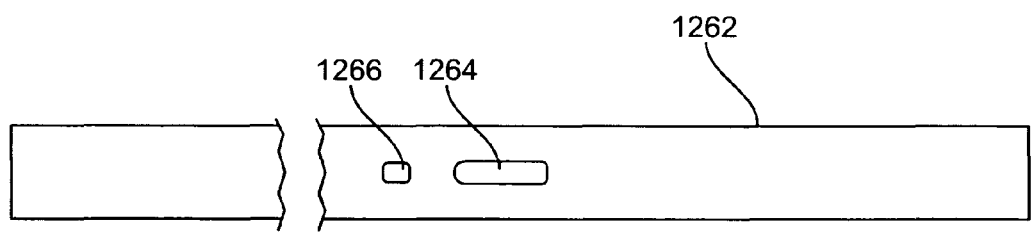

FIG. 58A shows the electrode of FIG. 57 mounted in a catheter housing 1260. The housing 1260 has a flange 1256. Struts are embedded in the housing and therefore, only the electrode 1254 is exposed. An aperture for a guidewire is more clearly visible in FIG. 58A and is represented by 1258. FIG. 58C illustrates a piece of tubing 1262 used to transition from the guidewire aperture 1258 into the guidewire lumen of the catheter shaft 1252 in FIG. 58A. The tubing is a length polymer tube with two apertures adapted to be placed over tabs 1210 and 1212 in FIG. 57 to secure the tubing to the electrode. Tab 1212 may also be bent at an angle to further facilitate guidewire entry and exit from the guidewire aperture 1258. FIG. 58B highlights the two apertures on the tubing. In a preferred embodiment, not intended to be limited, this tubing is approximately 0.044 inch outer diameter×0.039 inch inner diameter polyimide with a length about 39 inches. The long aperture 1264 is approximately 0.687 inches from the distal tip of the tubing and has a width of about 0.033 inches by 0.134 inches long and a radius approximately 0.017 inches. The smaller aperture 1266 is approximately 0.038 inches by 0.028 inches.

In addition to applying energy for closure of a layered tissue defect, the electrodes of such a device can be designed to allow electrophysiology monitoring of the heart. Such mapping would permit a physician to determine if the treatment device is too close to sensitive areas of the heart, such as the AV node. Additionally, monitoring could be used to ensure that during treatment, aberrant conductive pathways were not being created. Mapping also allows power delivery to be controlled so that minimal required power is delivered and also permits the active surface of the electrode to be controlled and minimized so that treatment energy is not applied to an area greater than necessary.

Figure 58D:
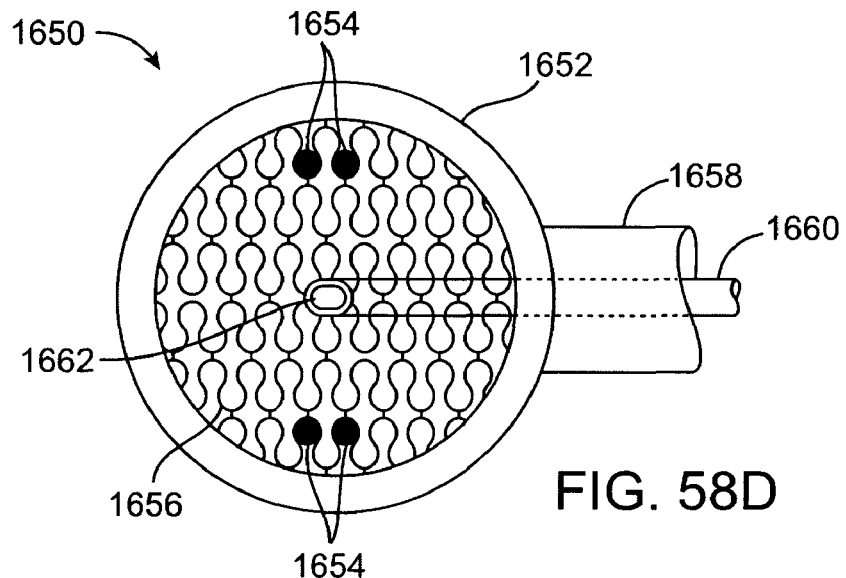
FIGS. 58D-58F illustrate various aspects of an electrophysiological mapping system combined with the closure treatment device.
Figure 58E:
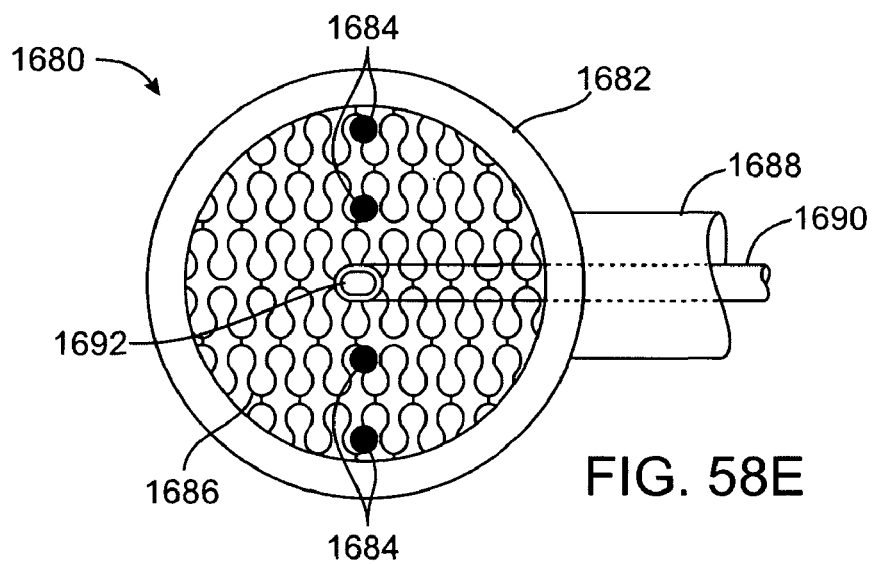
Figure 58F:
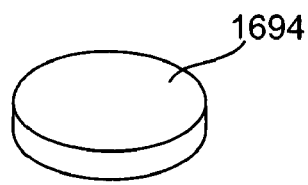

As shown in FIG. 58D, two small circular electrode pairs 1654 may be placed on and insulated from the electrode 1656 or housing 1652 and can serve as bipolar mapping electrodes. The electrodes may take a number of configurations such as two pairs side by side in FIG. 58D or in a linear arrangement 1684 as shown in FIG. 58E. These electrodes 1694 may be 0.5 mm to 2 mm in diameter as shown in FIG. 58F, and can be fabricated from stainless steel although platinum or platinum-iridium are preferable as well as nitinol. Cardiac electrophysiology mapping is well known in the art and is well documented in the medical and scientific literature. Exemplary products are manufactured by Boston Scientific.

Algorithm. In the treatment of a PFO in a human heart, the following welding algorithms may be successfully employed to achieve closure or sealing of the PFO tissues using a range of parameters that utilize feedback to vary the time and power applied to achieve a tissue weld. The following are merely examples and not intended to limit the scope of the present invention. In a preferred embodiment, the algorithm would start at a low power (e.g. 1-10 Watts to 20-50 Watts) and gradually increase over time. This allows the controller to evaluate how the defect is responding to the application of energy. The objective of the algorithm is to deliver the maximum amount of power during a desired duration, while not over-treating the tissue. A software controller system may be employed to ramp the power over the designated time and to respond to the impedance readings or other user or manufacturer designated feedback or settings.

Figure 59:
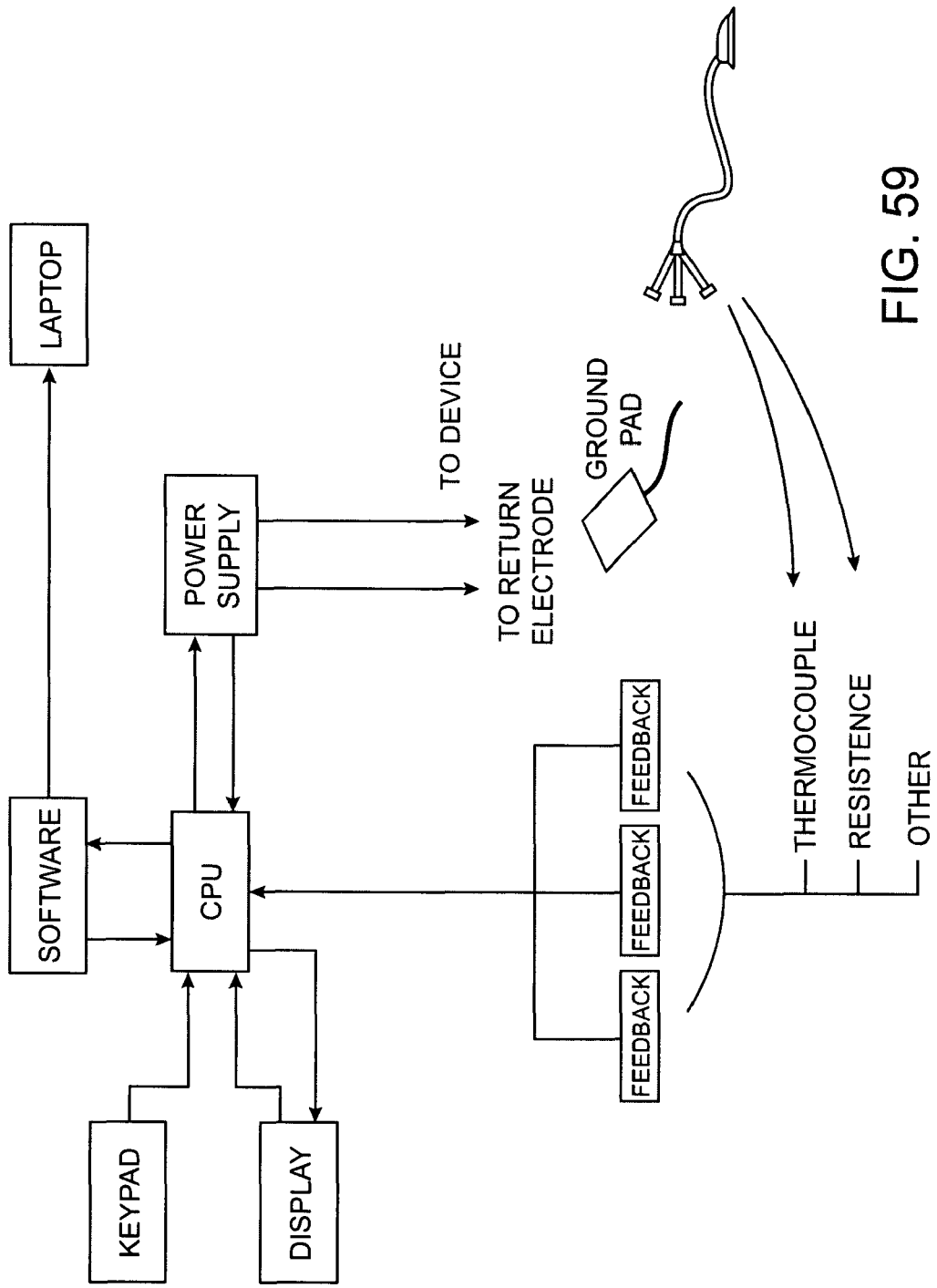
FIG. 59 is a schematic representation of a closure treatment system.

A schematic depiction of the power supply is depicted in FIG. 59. The power supply is connected to the treatment device and a return electrode is connected to the generator. A variety of feedback inputs may also be connected to the power supply or CPU, including thermocouples, electrodes for sensing impedance and the like. A software controller system utilizing a CPU can be employed to adjust the power over the designated time and to respond to the impedance readings (e.g. shut off/restart/restart at lower or higher power as directed by the input algorithm). This system may be further linked to a computer (laptop) or other user interface for purposes of graphical interface and data collection.

Figure 60:
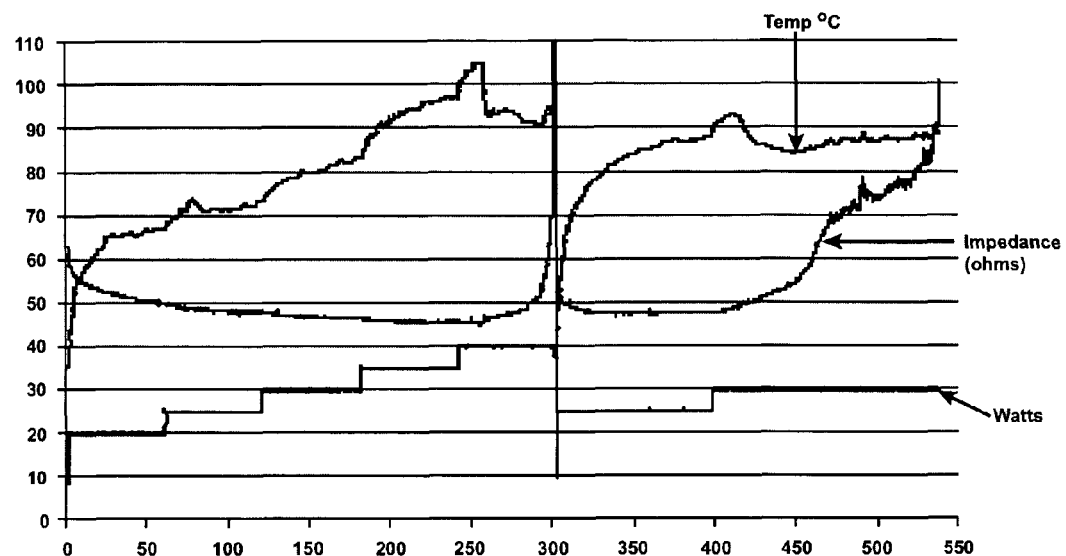
FIGS. 60-67 are graphs illustrating energy algorithms.
Figure 61:
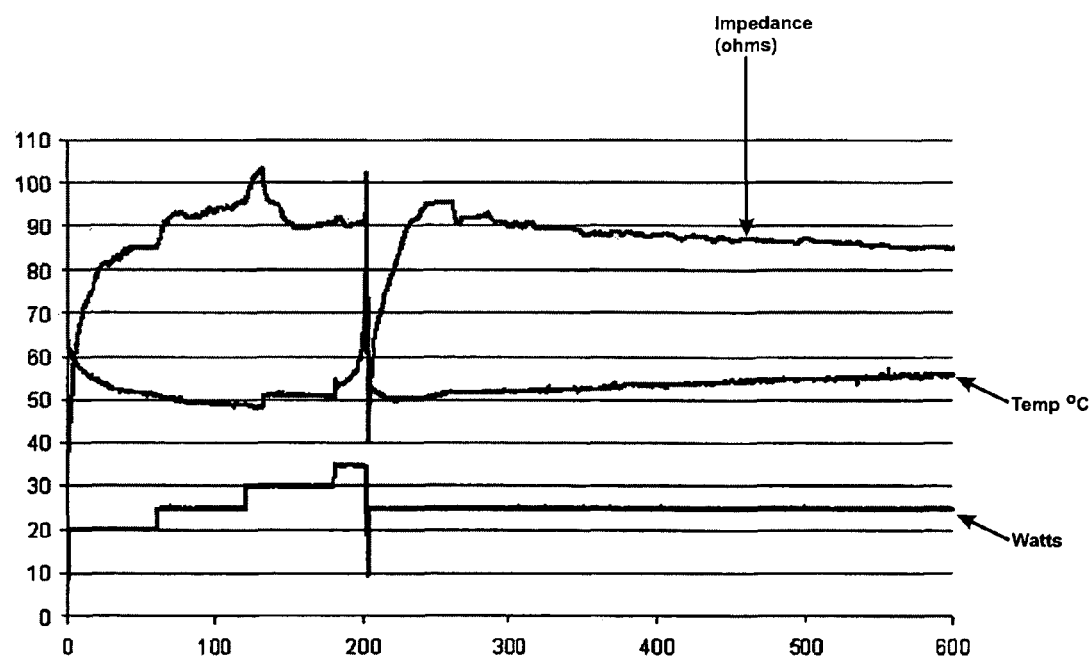

In one example of a tissue welding algorithm for PFO treatment, energy may be applied with an initial power setting of 20 Watts, and the power increased every 30 seconds by 5 Watts until 40 Watts is reached ("power ramp"). Following this initial ramp, energy may be applied until either 1) a total run time of 10 minutes is reached, or 2) an impedance spike occurs. If the total run time reaches 10 minutes the application of power is considered complete for purposes of this example. If an impedance spike is reached, an additional power ramp is reapplied until a total of five spikes have occurred or until a subsequent spike occurs after a cumulative run time of 7 minutes. The power ramp of this or other embodiments may also be incremental, e.g. ramp increased over 30 seconds, up to 5 Watts, until 40 Watts is achieved. Alternatively, the power ramp may begin at 20 Watts, increased to 25 Watts and maintained at 25 Watts until the application is complete (7-10 minutes), as shown in FIG. 60. The application of a similar algorithm in a different tissue sample, may produce results such as those below; the variations may be due to tissue or other anatomical variations, as shown in FIG. 61.

Figure 62:
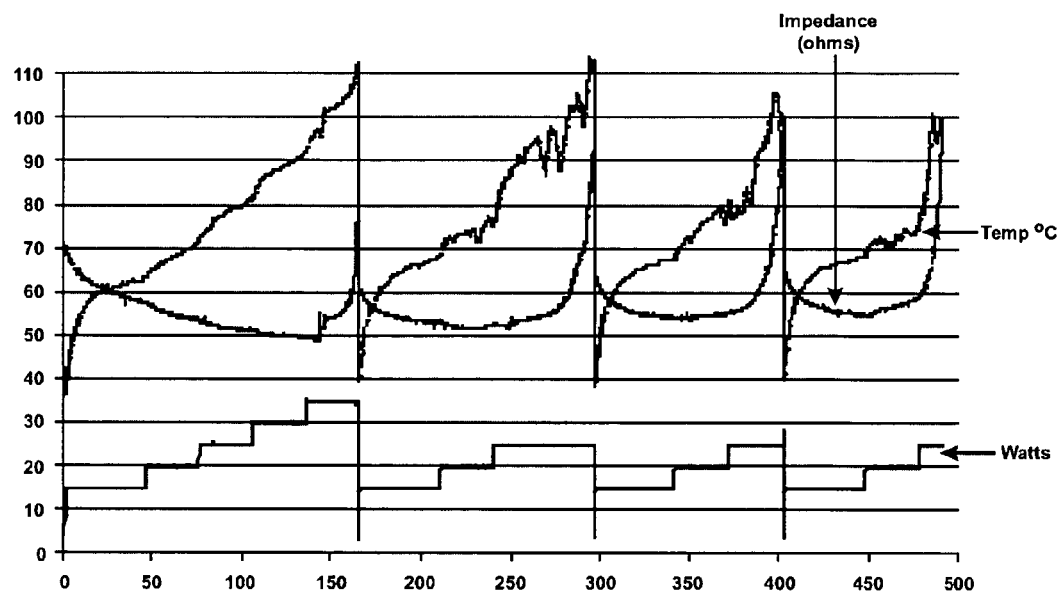

In another example of ramping, the system operates to apply 15 Watts, ramped by 5 Watts every 30 seconds after initial 45 seconds, for 10 minutes or first impedance spike after 7 minutes. The overall number of impedance spikes is limited to 5. The system in this example includes passive fluid infusion. A solution of D5W, or other fluids such as normal saline may be employed for the infusion. An example of this treatment using a banded electrode (see description of banded electrode above), is shown in FIG. 62.

Figure 63:
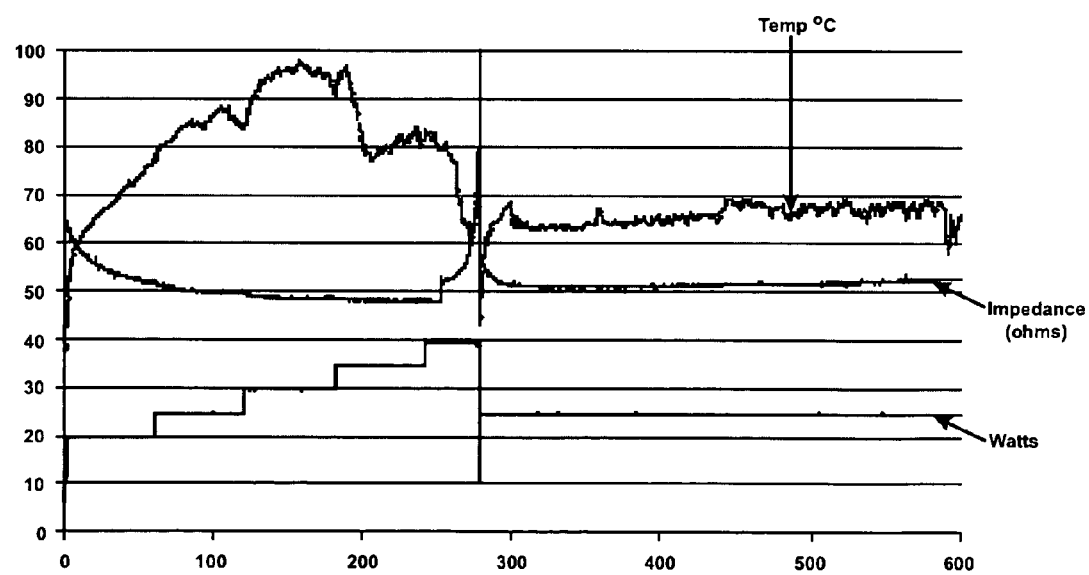
Figure 64:
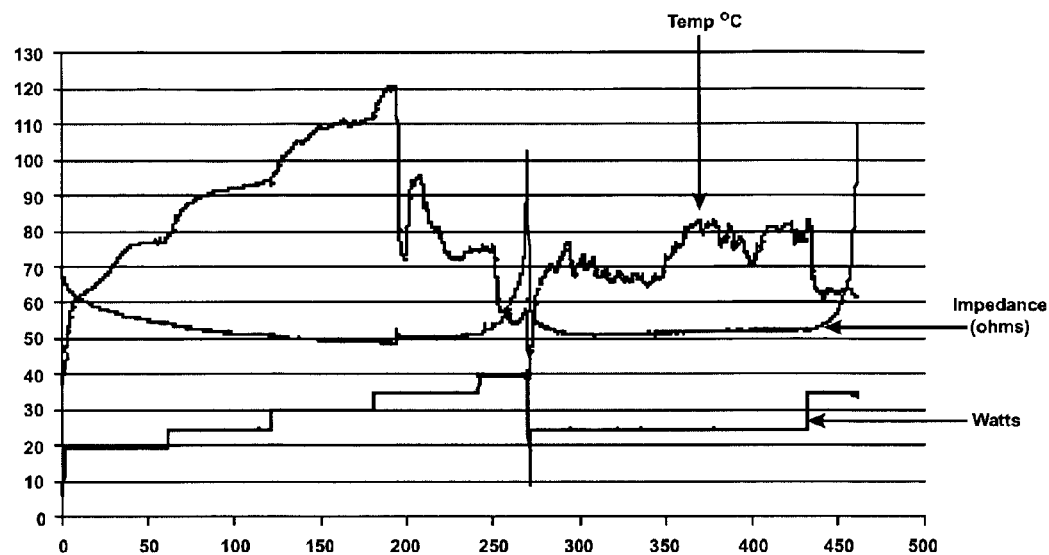

In addition, it may be advantageous to alter the starting power, and time between ramps, for example allowing additional time between step ups in power, for example 60 seconds. In the example below, the initial power is 20 Watts, with a step up in power of 5 Watts every 60 seconds, to a maximum power of 40 Watts for a duration of 10 minutes. If an impedance spike is encountered, then applied power is reduced to 25 Watts for the remaining time up to 10 minutes, as shown in FIG. 63. Following the initial spike, if the impedance reading does not exceed the minimum impedance by 2 Ohms, the power can be ramped up to 35 Watts for the remainder of the procedure time, as shown in FIG. 64.

Figure 65:
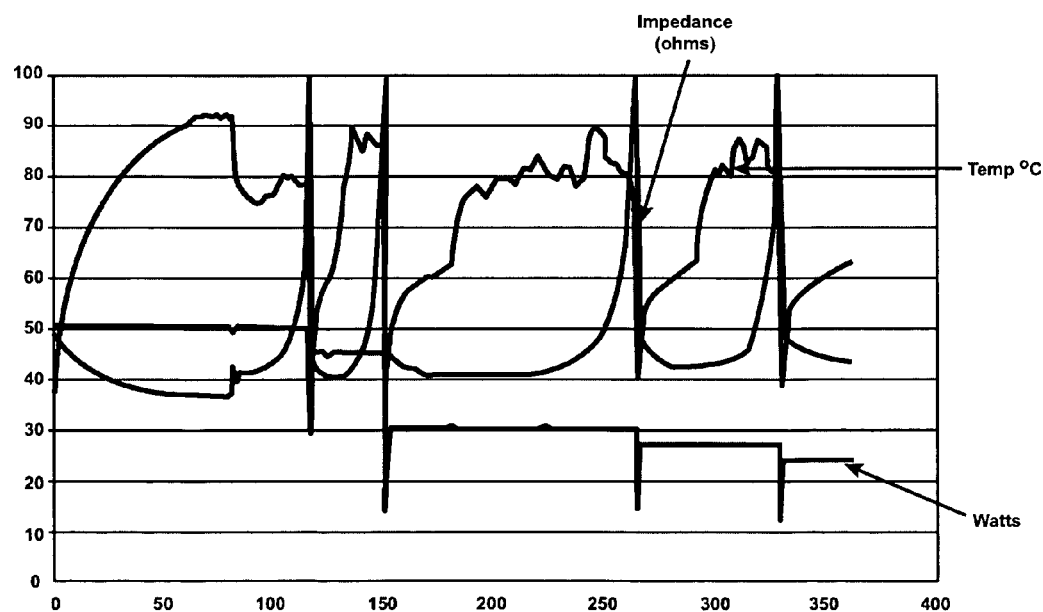

Alternatively, an algorithm where energy delivery is initiated at a higher power (for example 50 Watts) and ramped down in response to impedance spikes or "pops" may be employed as shown in FIG. 65. For example, power may be applied starting at 50 Watts, and a clinically acceptable procedure time followed (e.g. 5-15 minutes).

The power may then be reduced by 7 Watts each time the impedance spikes after fewer than 2 minutes of power application (an impedance "spike" in this example, is characterized by a rise in tissue impedance to about 100Ω). For example, if the power is set to 50 Watts and runs for 1 minute 30 seconds before spiking, energy application is stopped, power is reduced to 43 Watts and energy application is resumed. If the system then runs at 43 Watts for 3 minutes before spiking, the energy application is stopped only briefly before being reapplied at 43 Watts again. If there are spikes during the application of power, this process is repeated until a maximum cumulative run time of between 6 and 12 minutes is reached. If there is a spike after a cumulative run time of 6 minutes, the application of power is considered complete. If there is no spike, the energy application is continued at a power setting of 50 Watts for a maximum of 12 minutes.

Figure 66A:
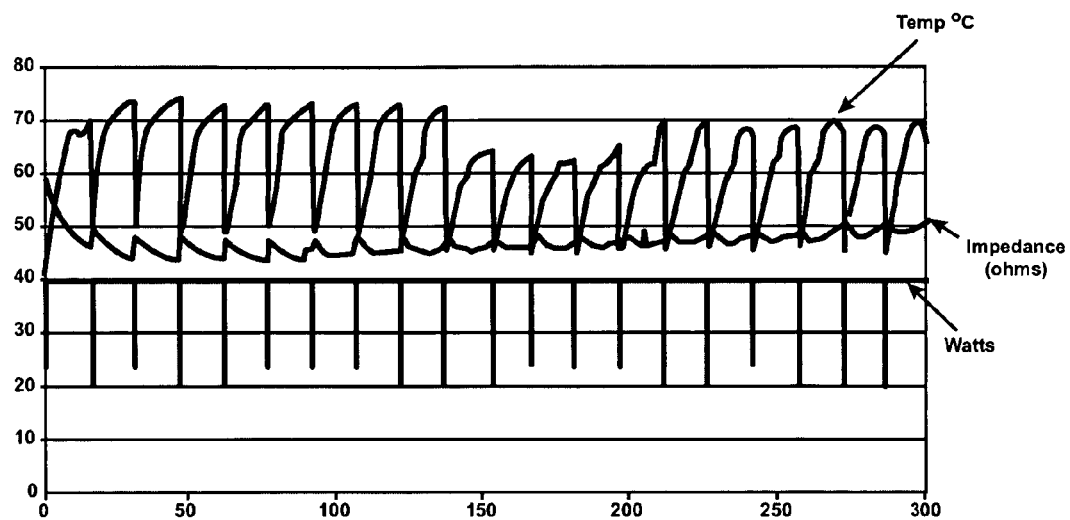
Figure 66B:
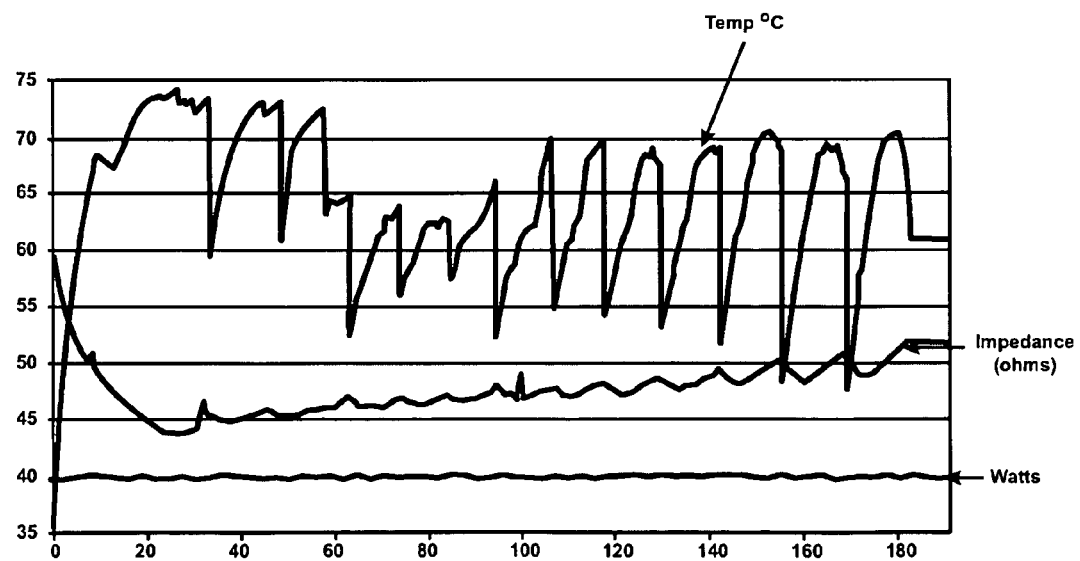

An example of application of pulsed power is depicted in FIG. 66A using a banded electrode. Forty (40) Watts of power was applied in 15 second pulses, and temperature and impedance were monitored and charted. In FIG. 66A each power application consisted of approximately 5 seconds of warm-up where the impedance dropped, after which the impedance resumed where it left off from a previous power application. FIG. 66B depicts the same power application as FIG. 66A however the chart reflects the data with the 5 seconds of warm-up in each application of energy (included in the graph of FIG. 66A) removed.

In a preferred embodiment of the algorithm, power is delivered in multiple power runs or frames. In the first frame, RF power is set to 20 Watts and power is increased by 5 Watts every 60 seconds until a maximum of 40 Watts is obtained. If during this frame, impedance inflects and then returns to at least its initial value or appears to be reaching a spike then power is turned off. If power has been delivered for more than 7 minutes, application of power is terminated and a cool down step is initiated. If power has been delivered for less than 7 minutes, then additional power is applied after a 30 to 120 second pause.

In the second power run or frame, if RF energy was delivered for 180 seconds or less during the first run, the second frame may be started at 15 Watts. If the impedance has not exceeded its minimum from the second frame by 2Ω after 90 seconds, power is increased to 25 Watts. If after another 90 seconds, the impedance has not exceeded its minimum from the second frame, power is again increased to 35 Watts. If the impedance inflects and then returns to at least its initial value (of the current frame) or if impedance appears to be reaching a spike, power is turned off. Similar to the first frame, if power was on for more than a total of 7 minutes, power is turned off and the cool down step is initiated. If power has been run for a total of fewer than 7 minutes, then additional power should be applied in the third power run after waiting 30 to 120 seconds.

If more than 180 seconds of RF was delivered during the first frame then RF power is applied at 25 Watts. If the impedance has not exceeded its minimum from the second frame by 2Ω after 90 seconds, power is increased to 35 Watts. If the impedance inflects and then returns to at least its initial value (of the current frame) or appears to be reaching a spike, power is turned off. If power has been delivered for more than a total of 7 minutes, the power is turned off and the cool down step is initiated. Otherwise, if power has been delivered for fewer than 7 minutes, then additional power should be applied in a third power run, after waiting 30 to 120 seconds.

In the third power frame, RF power is applied at the last setting used in the second frame, e.g. either 15, 25 or 35 Watts. If impedance inflects and then returns to at least its initial value (of the current frame) or appears to be reaching a spike, power delivery is terminated and the cool down step is initiated.

In all power frames, when total power delivery time reaches 10 minutes, power is turned off and cool down is initiated. During cool down, RF power delivery is stopped and tissue temperature is monitored. Tissue is allowed to cool down for at least 30 seconds or until tissue temperature is 40° C. or lower before moving the treatment device.

Figure 67:
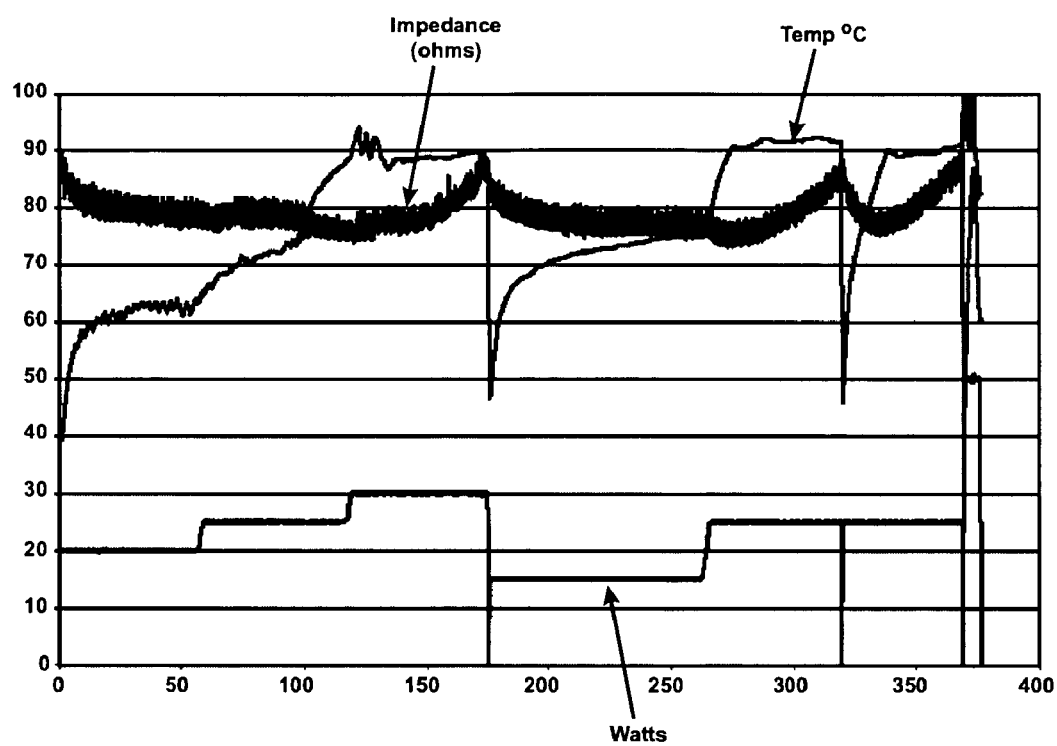

In FIG. 67, the preferred algorithm is utilized. Here, the first application of power was less than 3 minutes therefore the second application was initiated at 15 Watts, instead of 25 Watts. There are still power spikes if the impedance is stagnant, as shown in FIG. 67, where power is increased to 25 Watts because the impedance did not exceed its minimum by 2 Ohms after 90 seconds. If the impedance continued to remain stagnant, then after another 180 seconds, there is potential for another increase in power up to 35 Watts.

In all cases, power is applied at least once, but may be applied additional times, in this example at most, three times, although power may be delivered to help "burn off" and remove the electrode from the tissue. Power may range from 100 Watts down to 10 Watts, for example from 50 Watts down to 25 Watts. The total energy delivered to achieve a weld employing any of the algorithm examples above, or any variations thereof may be in the range of 1,000 joules to 50,000 joules, in the case of a PFO weld, a possible range of 6,000-15,000 joules.

Algorithm—Other Approaches, Adjustments. It is within the scope of the present invention to modify the parameters of the algorithm to achieve the desired tissue weld, to account for a number of variables, such as those described earlier in this disclosure. For example, treating a PFO with a thin primum may require longer application of power, higher power, or a higher ramp of power, given the potential for energy dissipation through the thinner tissue. Treating a different defect such as a ASD or LAA may require bringing tissues together that result in a thicker sample to weld, and therefore the treatment may utilize less total energy or lower applied powers, for example 5-35 Watts, or may include additional applications of power at multiple regions along the defect to be sealed.

In addition, an algorithm utilizing a bipolar treatment device such as those described earlier, may use a ramping algorithm such as that set forth above, but may utilize less power somewhere in the range of 1-25 Watts, for example 5-10 Watts and more particularly 2-3 Watts in some cases. Treatment times for bipolar application can range from 1-20 minutes.

Although the foregoing description is complete and accurate, it has described only exemplary embodiments of the invention. Various changes, additions, deletions and the like may be made to one or more embodiments of the invention without departing from the scope of the invention. Additionally, different elements of the invention could be combined to achieve any of the effects described above. Thus, the description above is provided for exemplary purposes only and should not be interpreted to limit the scope of the invention as set forth in the following claims.

What is claimed is:

1. A method for fusing apposed layered tissue structures, the method comprising:
    applying energy to the apposed layered tissue structure; and
    controlling the applied energy to minimize creation of aberrant conductive paths and enhance fusing of adjacent tissue layers in the layered tissue structure,
    wherein the controlling the applied energy includes:
        applying power at an initial level of $P_0$,
        increasing the power to a higher level of $P_1$ over a time period of $t_1$, and
        terminating the power after a time period $t_2$ if no impedance spike occurs.

2. The method as in claim 1, further comprising:
    reducing or terminating the power if an impedance spike occurs;
    reapplying the power at a lower level $P_2$ over a time period $t_3$; and terminating the reapplied power if an impedance spike occurs.

3. The method as in claim 1, wherein the applied energy is controlled to create a weld lesion having a predetermined size in the range from 2 mm$^2$ to 400 mm$^2$.

4. The method as in claim 1, wherein the applied energy is controlled to create a weld lesion having a predetermined size in the range from 5 mm$^2$ to 90 mm$^2$.

5. The method as in claim 1, further comprising measuring a tissue response parameter and controlling the applied energy in response to the measured tissue response parameter.

6. The method as in claim 5, wherein the measured tissue response parameter is selected from the group consisting of tissue temperature, tissue impedance, and tissue moisture.

7. The method as in claim 1, wherein the controlling further includes varying over time at least one energy parameter selected from the group consisting of power, pulse rate, frequency, rate of increase, rate of decrease, and duration.

8. The method as in claim 7, wherein the energy parameter is varied at least partly in response to an algorithm.

9. The method as in claim 8 wherein the algorithm is dependent upon a tissue response parameter.

* * * * *